United States Patent
Beane-Ebel et al.

(10) Patent No.: US 10,927,417 B2
(45) Date of Patent: Feb. 23, 2021

(54) GENE EXPRESSION-BASED BIOMARKER FOR THE DETECTION AND MONITORING OF BRONCHIAL PREMALIGNANT LESIONS

(71) Applicant: Trustees of Boston University, Boston, MA (US)

(72) Inventors: Jennifer E. Beane-Ebel, Rio Rancho, NM (US); Anna Tassinari, Boston, MA (US); Avrum Spira, Newton, MA (US); Marc E. Lenburg, Berkeley, CA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 15/644,721

(22) Filed: Jul. 7, 2017

(65) Prior Publication Data
US 2018/0010197 A1  Jan. 11, 2018

Related U.S. Application Data

(60) Provisional application No. 62/360,218, filed on Jul. 8, 2016.

(51) Int. Cl.
*C12Q 1/68* (2018.01)
*C12Q 1/6886* (2018.01)

(52) U.S. Cl.
CPC ...... C12Q 1/6886 (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,640,268 A | 2/1972 | Davis |
| 4,641,662 A | 2/1987 | Jaicks |
| 4,800,896 A | 1/1989 | Jalowayski |
| 5,422,273 A | 6/1995 | Garrison |
| 5,440,942 A | 8/1995 | Hubbard |
| 5,477,863 A | 12/1995 | Grant |
| 5,726,060 A | 3/1998 | Bridges |
| 5,795,782 A | 8/1998 | Church et al. |
| 5,876,978 A | 3/1999 | Willey et al. |
| 6,085,907 A | 7/2000 | Hochmeister |
| 6,676,609 B1 | 1/2004 | Rutenberg |
| 6,746,846 B1 | 6/2004 | Wang et al. |
| 2002/0081612 A1 | 6/2002 | Katz et al. |
| 2002/0094547 A1 | 7/2002 | Burstein |
| 2002/0160388 A1 | 10/2002 | Macina et al. |
| 2003/0104499 A1 | 6/2003 | Pressman et al. |
| 2004/0005294 A1 | 1/2004 | Lee |
| 2004/0009489 A1 | 1/2004 | Golub et al. |
| 2004/0063120 A1 | 4/2004 | Beer et al. |
| 2004/0197785 A1 | 10/2004 | Willey et al. |
| 2004/0241725 A1 | 12/2004 | Xiao et al. |
| 2004/0241728 A1 | 12/2004 | Liew |
| 2005/0260586 A1 | 11/2005 | Demuth et al. |
| 2005/0266409 A1 | 12/2005 | Brown et al. |
| 2006/0127928 A1 | 6/2006 | Bacus et al. |
| 2006/0140960 A1 | 6/2006 | Wang et al. |
| 2006/0154278 A1 | 7/2006 | Brody et al. |
| 2006/0183144 A1 | 8/2006 | Willey et al. |
| 2006/0188909 A1 | 8/2006 | Willey et al. |
| 2006/0190192 A1 | 8/2006 | Willey et al. |
| 2006/0194216 A1 | 8/2006 | Willey et al. |
| 2007/0092891 A1 | 4/2007 | Willey et al. |
| 2007/0092892 A1 | 4/2007 | Willey et al. |
| 2007/0092893 A1 | 4/2007 | Willey et al. |
| 2007/0148650 A1 | 6/2007 | Brody et al. |
| 2009/0061454 A1 | 3/2009 | Brody et al. |
| 2009/0186951 A1 | 7/2009 | Brody et al. |
| 2009/0246779 A1 | 10/2009 | Rabinovitch et al. |
| 2009/0311692 A1 | 12/2009 | Brody et al. |
| 2010/0035244 A1 | 2/2010 | Brody et al. |
| 2010/0055689 A1 | 3/2010 | Brody et al. |
| 2011/0053158 A1 | 3/2011 | Mambo et al. |

(Continued)

FOREIGN PATENT DOCUMENTS

DE  10219117 C1 * 10/2003
WO  WO 1999/060160 A1  11/1999

(Continued)

OTHER PUBLICATIONS

Strausberg et al, in Microarrays and Cancer Research, 2002, Warrington et al (eds.), Eaton Publishing, Westborough, MA, pp. xi-xvi.*

Notterman et al, in Microarrays and Cancer Research, 2002, Warrington et al (eds.), Eaton Publishing, Westborough, MA, pp. 81-111.*

Lin et al, Med. J. Chinese People's Liberation Army 6(31): 592 (2006)—Abstract Only.*

Final Office Action dated Aug. 18, 2014 U.S. Appl. No. 11/294,834.*

Abrahamson, et al., "Cystatins," *Biochem. Soc. Symp*, 70:179-199, (2003).

Akita, et al., "Molecular Biology of Lung Cancer," *The Journal of the Japanese Respiratory Society*, 42(5):378-86, (2004).

Ambion, Inc. "GeneAssist Pathway Atlas for P13K Signaling," Accessed from http://www5.appliedbiosystems.com/tools/pathway/pathway_proteins.php?pathway=P13K on May 3, 2011.

Anbazhagan, et al., "Classification of Small Cell Lung Cancer and Pulmonary Carcinoid by Gene Expression Profiles," *Cancer Research*, 59:5119-5122, (Oct. 15, 1999).

Anderson, et al., "Deaths: Leading Causes for 2001," *National Vital Statistics Report*, 52(9):1-88, (Nov. 7, 2003).

(Continued)

*Primary Examiner* — James Martinell
(74) *Attorney, Agent, or Firm* — Morse, Barnes-Brown & Pendleton, P.C.; Lisa M. Warren, Esq.

(57) ABSTRACT

Disclosed herein are assays and methods for the identification of premalignant lesions, as well as methods of determining the likelihood that such premalignant lesions will progress to lung cancer. Also disclosed are methods and assays that are useful for monitoring the progression of premalignant lesions to lung cancer. The assays and methods disclosed herein provide minimally invasive means of accurately detecting and monitoring the presence or absence of premalignant lesions, thus providing novel insights into the earliest stages of lung cancer and facilitating early detection and early intervention.

6 Claims, 9 Drawing Sheets
(8 of 9 Drawing Sheet(s) Filed in Color)

(56) References Cited

U.S. PATENT DOCUMENTS

| | | | |
|---|---|---|---|
| 2011/0190150 | A1 | 8/2011 | Brody et al. |
| 2011/0217717 | A1 | 9/2011 | Brody et al. |
| 2012/0041686 | A1 | 2/2012 | Brody et al. |
| 2012/0190567 | A1 | 7/2012 | Brody et al. |
| 2012/0288860 | A1 | 11/2012 | Van Hoek et al. |
| 2012/0322673 | A1 | 12/2012 | Brody et al. |
| 2013/0023437 | A1 | 1/2013 | Brody et al. |
| 2013/0303826 | A1* | 11/2013 | Jurisica ............ G01N 33/57407 600/1 |
| 2014/0378425 | A1 | 12/2014 | Wilde et al. |
| 2015/0080243 | A1 | 3/2015 | Whitney et al. |
| 2015/0088430 | A1 | 3/2015 | Whitney et al. |
| 2015/0152474 | A1 | 6/2015 | Pawlowski et al. |
| 2015/0232945 | A1 | 8/2015 | Brody et al. |
| 2015/0354008 | A1 | 12/2015 | Brody et al. |
| 2016/0024583 | A1 | 1/2016 | Whitney et al. |
| 2016/0130656 | A1 | 5/2016 | Whitney et al. |
| 2017/0226591 | A1 | 8/2017 | Brody et al. |
| 2017/0247759 | A1 | 8/2017 | Wilde et al. |
| 2017/0328908 | A1 | 11/2017 | Brody et al. |
| 2018/0171418 | A1 | 6/2018 | Brody et al. |

FOREIGN PATENT DOCUMENTS

| | | |
|---|---|---|
| WO | WO 2000/006780 | 2/2000 |
| WO | WO 2001/028428 | 4/2001 |
| WO | WO 2002/006791 | 1/2002 |
| WO | WO 02/44331 | 6/2002 |
| WO | WO 02/086443 A2 | 10/2002 |
| WO | WO 2003/015613 | 2/2003 |
| WO | WO 03/040325 A2 | 5/2003 |
| WO | WO 2004/005891 A2 | 1/2004 |
| WO | WO 2004/029055 | 4/2004 |
| WO | WO 2004/091511 A2 | 10/2004 |
| WO | WO 2004/111197 A2 | 12/2004 |
| WO | WO 2005/000098 A2 | 1/2005 |
| WO | WO 2005/047451 A2 | 5/2005 |
| WO | WO 2006/056080 | 6/2006 |
| WO | WO 2006/113467 A3 | 10/2006 |
| WO | WO 2007/103541 A2 | 9/2007 |
| WO | WO 2009/039457 A2 | 3/2009 |
| WO | WO 2003/029273 A2 | 4/2009 |
| WO | WO 2009/121070 A1 | 10/2009 |
| WO | WO 2010/054233 | 5/2010 |
| WO | WO 2002/072866 | 9/2012 |
| WO | WO 2013/033640 | 3/2013 |
| WO | WO 2013/049152 | 4/2013 |
| WO | WO 2013/163568 | 10/2013 |
| WO | WO 2013/177060 A2 | 11/2013 |
| WO | WO 2014/144564 | 9/2014 |
| WO | WO 2014/186036 | 11/2014 |
| WO | WO 2016/011068 | 1/2016 |
| WO | WO 2017/197335 | 11/2017 |
| WO | WO 2018/009915 | 1/2018 |
| WO | WO 2018/048960 | 3/2018 |

OTHER PUBLICATIONS

Anthonisen, et al., "Effects of Smoking Intervention and the Use of an Inhaled Anticholinergic Bronchodilator on the Rate of Decline of FEV1," *JAMA*, 272(19):1497-1505, (Nov. 16, 1994).

Arimura, et al. "Elevated Serum β-Defensins Concentrations in Patients with Lung Cancer," *Anticancer Research*, 24:4051-4058, (2004).

Baker, "The Central Role of Receiver Operating Characteristic (ROC) Curves in Evaluating Tests for the Early Detection of Cancer," *Journal of the National Cancer Institute*, 95(7):511-515, (2003).

Beane, et al., "A Prediction Model for Lung Cancer Diagnosis that Integrates Genomic and Clinical Features," *Cancer Prev. Res.*, 1:56-64, (2008).

Beane, et al., "Reversible and Permanent Effects of Tobacco Smoke Exposure on Airway Epithelial Gene Expression," *Genome Biology*, 8:R201, (Sep. 25, 2007).

Beer, et al., "Gene-Expression Profiles Predict Survival of Patients with Lung Adenocarcinoma," *Nature Medicine*, 8:816-827 (2002).

Belinsky, et al., "Aberrant Promoter Methylation in Bronchial Epithelium and Sputum from Current and Former Smokers." *Cancer Res.*, 62(8):2370-7, (2002).

Benner, et al., "Evolution, Language and Analogy in Functional Genomics," *Trends in Genetics*, 17:414-418, (2001).

Berman Abstract Immunopathology of the Nasal Mucosa in Sarcoidosis National Institutes of Health Grant No. 1 R21 HL077498-01 Sep. 15, 2014.

Beum, et al., "Epidermal Growth Factor Downregulates Core 2 Enzymes in a Human Airway Adenocarcinoma Cell Line," *Am. J. Respir. Cell Mol. Biol.*, 29:48-56, (2003).

Bhattacharjee, et al., "Classification of Human Lung Carcinoma by mRNA Expression Profiling Reveals Distinct Adenocarcinoma Subclasses," *Proc. Natl. Acad. Sci. USA*, 98(24):13790-5, (Nov. 20, 2001).

Bild, et al., "Oncogenic Pathway Signatures in Human Cancers as a Guide to Targeted Therapies," *Nature*, 439:353-357, (2006).

Bohula, et al., "The Efficacy of Small Interfering RNAs Targeted to the Type 1 Insulin-like Growth Factor Receptor (IGF1R) Is Influenced by Secondary Structure in the IGF1R Transcript," *The Journal of Biological Chemistry*, 278(18):15991-15997, (2003).

Braakhuis, et al. "A Genetic Explanation of Slaughter's Concept of Field Cancerization: Evidence and Clinical Implications," *Cancer Research*, 63:1727-1730, (2003).

Brambilla, et al., "p53 Mutant Immunophenotype and Deregulation of p53 Transcription Pathway (Bcl2, Bax and Waf1) in Precursor Bronchial Lesions of Lunch Cancer," *Clinical Cancer Research*, 4:1609-1618, (1998).

Brody, Abstract "Airway epithelial gene expression in COPD" National Institutes of Health Grant No. 1 R01 HL071771-01 (Funding Start Date Sep. 30, 2002).

Chan, et al., "Intefrating Trasnscriptomics and Protemoics," *Genomics & Proteomics Magazine*, 6(3), text of article reprinted and accessed from www.dddmag.com on May 27, 2005.

Chari, et al., Effect of Active Smoking on the Human Bronchial Epithelium Transcriptome, *BMC Genomics*, 8:297, (Aug. 29, 2007).

Chen, et al., "Up-regulations of Tumor Interleukin-8 Expression by Infiltrating Macrophages: Its Correlation with Tumor Angiogenesis and Patient Survival in Non-Small Cell Lung Cancer," *Clinical Cancer Research*:pp. 729-737, (Feb. 1, 2003).

Chen, et al. "Discordant Protein and mRNA Expression in Lung Adenocarcinomas," *Molecular and Cellular Proteomics*, 1:304-313, (2001).

Cheng, et al., "Reduced Expression levels of Nucleotide Excision Repair Genes in Lung Cancer: A Case-Control Analysis," *Carincogenesis,*, 21:1527-1530, (2000).

Cheung, et al., "Natural Variation in Human Gene Expression Assessed in Lymphoblastoid Cells," *Nature Genetics*, 33:422-425, (2003).

Clark, et al., "Altered Protein Kinase C (PKC) Isoforms in Non-Small Cell Lung Cancer Cells: PKCdelta Promotes Cellular Survival and Chemotherapeutic Resistance," *Cancer Research*, 63(4):780-786, (2003).

Crawford, et al., "Normal Bronchial Epithelial Cell Expression of Glutathione Transferase P1, Glutathione Transferase M3, and Glutathione Peroxidase is Low in Subjects with Bronchogenic Carcinoma," *Cancer Research*, 60:1609-1618, (Mar. 15, 2000).

Cummings, et al., "Estimating the Probability of Malignancy in Solitary Pulmonary Nodules. A Bayesian Approach," *Am. Rev. Respir. Dis.*, 134:449-52, (1986).

Danel, et al., "Quantitative Assessment of the Epithelial and Inflammatory Cell Populations in Large Airways of Normals and Individuals with Cystic Fibrosis," *Am. Journal of Resp. and Critical Care Medicine*, 153:362-368, (1996).

Dauletbaev, et al. "Expression of Human Beta Defensin (HBD-1 and HBD-2) mRNA in Nasal Epithelia of Adult Cystic Fibrosis Patients, Healthy Individuals, and Individuals with Acute Cold," *Respiration*, 69:46-51, (2002).

(56) References Cited

OTHER PUBLICATIONS

Demeo, et al., "The SERPINE2 Gene Is Associated With Chronic Obstructive Pulmonary Disease," *Am. J. Hum. Genet.*, 78(2):253-264, (Feb. 2006).
Demoly, et al., "c-fos Proto-oncogene Expression in Bronchial Biopsies of Asthmatics," *American Journal of Respiratory Cell and Molecular Biology*, 7:128-133, (1992).
Dempsey, et al., "Lung Disease and PKCs," *Pharmacological Research* 55(6):545-59, (2007).
DeMuth, et al., "The Gene Expression of Index c-myc X E2F-1/p21 Is Highly Predictive of Malignant Phenotype in Human Bronchial Epithelial Cells," *Am. J. Cell Mol. Bio.*, 19:18-24, (1998).
Denis, et al., "RING3 Kinase Transactivates Promoters of Cell Cycle Regulatory Genes through E2F1 Cell," *Growth Differ*, 11:417-424, (Aug. 2000).
Details for HG-U112A:823_AT (http://www.affymetrix.com/analysis/netaffx/fullrecord.affx?pk=HG-U133A:823_AT, downloaded Dec. 10, 2012).
Details for HG-U133A:202831_AT (https://www.affymetrix.com/analysis/netaffx/fullrecord.affx?pk=HG-U133A:202831_AT, downloaded Dec. 10, 2012).
Details for HG-U133A:210519_S_AT (https://www.affymetrix.com/analysis/netaffx/fullrecord.affx?pk=HG-U133A:210519_S_AT downloaded Dec. 10, 2012).
Details for HG-U133A:217291 _AT (CEACAM5) (https://www.affymetrix.com/analysis/netaffx/fullrecord.affx?pk=HG-U133A:217291 _AT, downloaded Apr. 22, 2016).
Details for HG-U133a-207469_S_AT (https://www.affymetrix.com/analysis/netaffx/fullrecord.affx?pk=HG-U133A:207469_S_AT, downloaded Dec. 10, 2012).
Doll, et al., "Mortality in Relation to Smoking: 40 Years' Observations on Male British Doctors," *BMJ*, 309:901-911, (Oct. 8, 1994).
Ebbert, et al., "Lung Cancer Risk Reduction After Smoking Cessation: Observations From a Prospective Cohort of Women," *J Clin Oncol*; 21(5):921-926, (Mar. 1, 2003).
Enard, et al., "Intra- and Interspecific Variation in Primate Gene Expression Patters," *Science*, 296:340-343, (2002).
Fahy, "Remodeling of the Airway Epithelium in Asthma," *Am. J. Respir. Crit. Care Med.*, 164:S46-S51, (2001).
Fielding, et al., "Heterogeneous Nuclear Ribonucleoprotein A2/B1 Up-Regulations in Bronchial Lavage Specimens: A Clinical Marker of Early Lung Cancer Detection," *Clin. Cancer Res.*, 5:4048-4052, (1999).
Franklin, et al., "Widely Dispersed p53 Mutation in Respiratory Epithelium," *The Journal of Clinical Investigation*, 100(8):2133-2137, (1997).
Freeman, et al., "DNA from Buccal Swabs Recruited by Mail: Evaluation of Storage Effects on Long-term Stability and Suitability for Multiplex Polymerase Chain Reaction Genotyping," *Behavior Genetics*, 33:67, (2003).
Fritz, et al., "Nasal Mucosal Gene Expression in Pateitns Wth Allergic Rhinitis With and Without Nasal Polyps," *Journal of Allergy Clin. Immunol.*, 112(6):1057-1063, (2003).
Fukumoto, et al., "Overexpression of the Aldo-Keto Reductase Family Protein AKR1B10 is Highly Correlated with Smokers' Non-Small Cell Lung Carcinomas," *Clinical Cancer Research* 11:1776-1786, (2005).
Garber, et al., "Diversity of Gene Expression in Adenocarcinoma of the Lung," *PNAS*, 98(24):13784-13789, (Nov. 20, 2001).
Garcia-Closas, "Collection of Genomic DNA from Adults in Epidemiological Studies by Buccal Cytobrush and Mouthwash," *Cancer Epidemiology, Biomarkers and Prevention*, 10:687-696, (2001).
Gebel, et al., "Gene Expression Profiling in Respiratory Tissues From Rats Exposed to Mainstream Cigarette Smoke." *Carcinogenesis*, 25(2):169-178, (2004).
Golub, et al., "Molecular Classification of Cancer: Class Discovery and Class Prediction by Gene Expression Monitoring," *Science, American Association for the Advancement of Science*, 286:5439, (Oct. 15, 1999).

Greenlee, et al., "Cancer Statistics, 2001," *A Cancer Journal for Clinicians*, 51(1):15-36 (Jan./Feb. 2001).
Grepmeier, et al., "Deletions At Chromosome 2q and 12p Are Early Frequent Molecular Alterations in Bronchial Epithelium and NSCLC of Long-Term Smokers," *Int. J. Oncol.*, 27(2):481-8, (2005).
Guajardo, et al., "Altered Gene Expression Profiles in Nasal Respiratory Epithelium Reflect Stable Versus Actue Childhood Asthma," *J. Allergy Clin. Immunol.*, 115(2): 243-251, (2005).
Gurney, "Determining the Likelihood of Malignancy in Solitary Pulmonary Nodules With Bayesian Analysis, Part 1, Theory," *Radiology*, 186:405-13, (2005).
Gustafson, et al., "Airway P13K Pathway Activation Is an Early and Reversible Event in Lung Cancer Development," www.ScienceTranslationalMedicine.org 2(26), (2010).
Hackett, et al., "Variability of Antioxidant-Related Gene Expression in the Airway Epithelium of Cigarette Smokers," *American Journal of Respiratory Cell and Molecular Biology*, 29:331-343, (2003).
Hamilton, et al., "Diagnosis of Lung Cancer in Primary Care: A Structured Review," *Family Practice*, 21(6):605-611, (2004).
Hecht, SS., "Tobacco Carcinogens, Their Biomarkers and Tobacco-Induced Cancer," *Nature Review Cancer*, 3:733-744, (Oct. 2003).
Hellmann, et al. "Gene Profiling of Cultured Human Bronchia Epithelial and Lung Cacinoma Cells," *Toxicological Sciences*, 61:154-163, (2001).
Hennessy, et al., "Exploiting the PI3K/AKT Pathway for Cancer Drug Discovery," *Nature*,4:988-1004, (2005).
Hirsch, et al., "Early Detection of Lung Cancer: Clinical Perspectives of Recent Advances in Biology and Radiology," *Clinical Cancer Research*, 7:5-22, (2001).
Hoshikawa, et al., "Hypoxia Induces Different Genes in the Lungs of Rats Compared With Mice," *Physiol. Genomics*, 12:209-219, (2003).
Ikeda, et al. "Malignancy associated changes in bronchial epithelial cells and clinical application as a biomarker," *Lung Cancer*, 19(3):161-166, (1998).
Jang, et al., "Activation of Melanoma Antigen Tumor Antigens Occurs Early in Lung Carcinogenesis," *Cancer Research*, 61:7959-7963, (Nov. 1, 2001).
Kanner, et al., "Effects of Randomized Assignment to a Smoking Cessation Intervention and Changes in Smoking Habits on Respiratory Symptoms in Smokers With Early Chronic Obstructive Pulmonary Disease: The Lung Health Study," *American Journal of Medicine*, 106:410-416, (1999).
Kao, et al., "Tumor-Associated Antigen L6 and the Invasion of Human Lung Cancer Cells," *Clin. Cancer Res.*, 9:2807-2816, (Jul. 2003).
Katz, et al., "Automated Detection of Genetic Abnormalities Combined With Cytology in Sputum Is a Sensitive Predictor of Lung Cancer," *Modern Pathology*, 21:950-960, (2008).
Kazemi-Noureini, et al., "Differential Gene Expression Between Squamous Cell Carcinoma of Esophageus and Its Normal Epithelium; Altered Pattern of Mal, Akr1c2, and Rab11a Expression," *World J. Gastroenterol*, 10(12):1716-1721, (2004).
Khan, et al., "Classification and Diagnostic Prediction of Cancers Using Gene Expression Profiling and Artificial Neural Networks," *Nature Medicine*, 7(6):673-679, (Jun. 2001).
Kiss, et al., "Anatomisk Atlas Over Manniskokroppen, Band II," Natur och Kultur Stockholm, Stockholm, Sweden ISBN: 91-27-67278-6.
Kitahara, et al. "Alternations of Gene Expression during Colorectal Carcinogenesis Revealed by cDNA Microarrays after Laser-Captuer Microdissection of Tumor Tissues and Normal Epithelia," *Cancer Research*, 61:3544-3549, (May 1, 2011).
Kraft, et al. "Expression of Epithelial Markers in Nocturnal Asthma," *Journal of Allergy and Clinical Immunology*, 102(3): 376-381 (1998).
Lacroix, et al., "Sensitive Detection of Rare Cancer Cell in Sputum and Peripheral Blood Samples of Patients with Lunch Cancer by Preprogrp-Specific TR-PCR," *Int. J. Cancer*,92:1-8, (2001).
Lam, et al., "A Phase I Study of myo-Inositol for Lung Cancer Chemoprevention", *Cancer Epidemiology, Biomarkers & Prevention* 15(8):1526-1531, (2006).

(56) References Cited

OTHER PUBLICATIONS

Lander, et al., "Initial Sequencing and Analysis of the Human Genome," *Nature*, 409:860-921, (Feb. 15, 2001).
Langford, et al., "Is the Property of Being Positively Correlated Transitive," *The American Statistician*, 55(4):322-325, (2001).
Li, "Survival Prediction of Diffuse Large-B-Cell Lymphoma Based on Both Clinical and Gene Expression Information," *Bioinformatics*, 22:466-71, (2006).
Liao, et al., "Expression and Significance of PTEN/PI3K Signal Transduction-Related Proteins in Nonsmall Cell Lung Cancer," *Ai Zheng*, 25(10):1238-42, Abstract, (2006).
Liu et al., "Effects of Physiological Versus Pharmacological β-Carotene Supplementation on Cell Proliferation and Histopathological Changes in the Lungs of Cigarette Smoke-Exposed Ferrets," *Carcinogenesis*, 21:2245-2253, (2000).
Liu, et al. "Quantitative Proteome Analysis Reveals Annexin A3 as a Novel Biomarker in Lung Adenocarcinoma," *Journal of Pathology*, 217:54-64, (2009).
MacKay, et al., "Targeting the Protein Kinase C Family: Are We There Yet?" *Nature Reviews Cancer*, 7(7):554-62, (2007).
Mannino, et al., "Low Lung Function and Incident Lung Cancer in the United States: Data From the First National Health and Nutrition Examination Survey Follow-Up," *Arch. Intern. Med.*, 163(12)1475-80, (2003).
Marinov, et al., "Targeting mTOR Signaling in Lung Cancer," *Critical Reviews in Oncology/Hematology*, 63:172-182, (2007).
May, "How Many Species Are There on Earth?" *Science*, 241:1141-1449, (1988).
Medical News: Targeted, Oral Agent Enzastaurin Shows Favorable Results in Late-Stage Lung Cancer. (Jun. 11, 2007), Retrieved from the Internet <URL: http://www.medicalnewstoday.com/articles/73761.php>.
Merriam-Webster.com (http://www.merriam-webster.com/dictionary/questionnaire, downloaded Oct. 26, 2013.
Michalczyk, et al., "Fresh and Cultured Buccal Cells as a Source of Mrna and Protein for Molecular Analysis," *Biotechniques*, 37(2):262-4-266-9, (2004).
Miklos, et al., "Microarray Reality Checks in the Context of a Complex Disease," *Nature Biotechnology*, 22:5, (May 2005).
Miura, et al., "Laser Capture Microdissection and Microarray Expression Analysis of Lung Adenocarcinoma Reveals Tobacco Smoking- and Prognosis-Related Molecular Profiles," *Cancer Res.*, 62(11):3244-50, (Jun. 1, 2002).
Modrek, et al., "Genome-Wide Detection of Alternative Splicing in Expressed Sequences of Human Genes," *Nucleic Acids Research*, 29(13):2850-2859, (2001).
Moller, et al., "Altered ratio of endothelin ETA- and ETB receptor mRNA in bronchial biopsies from patients with asthma and chronic airway obstruction," Eur. Journal of Pharmacology, 365:R1-R3, (1999).
Mollerup, et al., "Sex Differences in Lung CYP1A1 Expression and DNA Adduct Levels among Lung Cancer Patients," *Cancer Research*, 59:3317-3320, (1999).
Mongiat, et al., "Fibroblast Growth Factor-binding Protein Is a Novel Partner for Perlecan Protein Core," *The Journal of Biological Chemistry*, 276(13):10263-10271, (Mar. 30, 2001).
Neubauer, et al., "Cure of Helicobacter pylori Infection and Duration of Remission of Low-Grade Gastric Mucosa-Associated Lymphoid Tissue Lymphoma," *J. Natl. Cancer Inst.*, 89(18):1350-1378, (Sep. 17, 1997).
Newton, et al., "On Differential Variability of Expression Ratios: Improving Statistical Inference about Gene Expression Changes from Microarray Data," *Journal of Computational Biology*, 8:37-52, (2001).
Ohtsuka, et al., "ADAM28 is Overexpressed in Human Non-Small Cell Lung Carcinomas and Correlates With Cell Proliferation and Lymph Node Metastasis," *International Journal of Cancer*, 118(2):263-273, (2006).
Okudela, et al., "K-ras Gene Mutation Enhances Motility of Immortalized Airway Cells and Lung Adenocarcinoma Cells Via Akt Activation: Possible Contribution to Non-Invasive Expansion of Lung Adenocarcinoma," *The American Journal of Pathology*, 164(1):91-100, (2004).
Peluso, et al., "Comparison of DNA Adduct Levels in Nasal Mucosa, Lymphocytes and Bronchial Mucosa of Cigarette Smokers and Interaction With Metabolic Gene Polymorphisms," *Carcinogenesis*, 25(12):2459-2465, (2004).
Pittman, et al., "Integrated Modeling of Clinical and Gene Expression Information for Personalized Prediction of Disease Outcomes," *Proc. Natl. Acad. Sci. USA*, 101:8431-6, (2004).
Potti, et al., "A Genomic Strategy to Refine Prognosis in Early-Stage Non Small-Cell Lung Cancer," *The New England Journal of Medicine*, 335(6):570-580, (2006).
Potti, et al., "Genomic Signatures to Guide the Use of Chemotherapeutics," *Nature Medicine*, 12(11):1294-1300, (2006). (Retracted in Jan. 2011.).
Powell, et al., "Gene Expression in Lung Adenocarcinomas of Smokers and Nonsmokers," *American Journal of Respiratory Cell and Molecular Biology*, 29:157-162, (Aug. 2003).
Powell, et al., "Patterns of Allelic Loss Differ in Lung Adenocarcinomas of Smokers, and Nonsmokers," *Lung Cancer*, 39(1):23-29, (2003).
Printout from database NCBI GEO accession No. GSE4115 [Online] NCB, dated Feb. 27, 2006.
Proctor, "Tobacco and the Global Lung Cancer Epidemic," *Nature Reviews Cancer*, 1:82-86, (Oct. 2001).
Reynolds, et al. "Pre-Protachykinin-A Mrna Is Increased in the Airway Epithelium of Smokers With Chronic Bronchitis," *Respiratory*, 6:187-197, (2001).
Riise, et al. "Bronchial Brush Biopsies for Studies of Epithelial Inflammation in Stable Asthma and Nonobstructive Chronic Bronchitis," *European Respiratory Journal*, 9: 1665-1671, (1996).
Rusznak, et al., "Effect of Cigarette Smoke on the Permeability and IL-1 B and sICAM-1 Release from Cultured Human Bronchial Epithelial Cells of Never-Smokers, Smokers, and Patients with Chronic Obstructive Pulmonary Disease," *Am. J. Respir. Cell Mol. Biol.*, 23:530-536, (2000).
Saal, et al., "Poor Prognosis in Carcinoma is Associated with a Gene Expression Signature of Aberrant PTEN Tumor Suppressor Pathway Activitiy," *PNAS*, 104(18): 7564-7569, (2007).
Saheki, et al., "Pathogenesis and pathophysiology of citrin (a mitochondrial aspartate glutamate carrier) deficiency." Metabolic Brain Disease; 17(4):335-346 (Dec. 2002).
Saito-Hisaminato, "Genome-Wide Profiling of Gene Expression in 29 Normal Human Tissues with a cNDA Microarray," *DNA Research*, 9:35-45, (2002).
Schembri, et al., "MicroRNAs As Modulators of Smoking-Induced Gene Expression Changes in Human Airway Epithelium," *Proc. Natl. Acad. Sci. USA*, 106(7):2319-24, (Feb. 2009).
Shah et al., "SIEGE: Smoking Induced Epithelial Gene Expression Database," *Nucleic Acids Research*, 33:D573-D579, (2005).
Shields, "Molecular Epidemiology of Lung Cancer," *Annals of Oncology*, 10(5):S7-S11, (1999).
Shriver, et al., "Sex-Specific Expression of Gastrin-Releasing Peptide Receptor: Relationship to Smoking History and Risk of Lung Cancer," *J. Natl. Cancer Inst.*, 92: 24-33, (2000).
Singhal, et al., "Alterations in Cell Cycle Genes in Early Stage Lung Adenocarcinoma Identified by Expression Profiling," *Cancer Biology & Therapy* 2(3):291-299, (2003).
Slonim, "From Patterns to Pathways: Gene Expression Data Analysis Comes of Age," *Nature Genetics Supplement*, 32:502-508, (2002).
Sotos, et al., "The Transitivity Misconception of Pearson's Correlation Coefficient," *Statistics Education Research Journal*, 8(2):33-55, (2009).
Spira, Abstract Airway gene expression in smokers: an early diagnostic biomarker for lung cancer National Institutes of Health Grant No. 1 R01 CA124640-01 (Funding Start Date May 1, 2007).
Spira, Abstract the airway transcriptome as a biomarker for lung cancer National Institutes of Health Grant No. 1 R21 CA106506-01 (Funding Start Date Aug. 9, 2005).
Spira, et al., "Airway Epithelial Gene Expression in the Diagnostic Evaluation of Smokers With Suspect Lung Cancer," *Nature Medicine*, 13:361-366, (2007).

(56) References Cited

OTHER PUBLICATIONS

Spira, et al., "Effects of Cigarette Smoke on the Human Airway Epithelial Cell Transcriptome," *PNAS*, 101(27):10143-10148, (Jul. 6, 2004).
Spira, et al., "Gene Expression Profiling of Human Lung Tissue from Smokers with Severe Emphysema," *Am. J. Respir. Cell Mol. Biol.*, 31(6):601-10, (2004).
Spira, et al., "Impact of Cigarette Smoke on the Normal Airway Transcriptome," *Chest*, 125(5 Suppl):115S, (May 2004).
Spira, et al., "Noninvasive Method for Obtaining RNA From Buccal Mucosa Epithelial Cells for Gene Expression Profiling," *Biotechniques*, 36(3):484-7, (2004).
Spivack, et al., "Gene-Environment Interaction Signatures by Quantitative Mrna Profiling in Exfoliated Buccal Mucosal Cells," *Cancer Research*, 64(18):6805-6813, (2004).
Sridhar, et al. "Smoking-Induced Gene Expression Changes in the Bronchial Airway Are Reflected in Nasal and Buccal Epithelium," *BMC Genomics*, 9:259, (May 2008).
St. Croix, et al. "Genes Expressed in Human Tumor Endothelium," *Science*, 289:1197-1202, (Aug. 18, 2000).
Stephenson, et al., "Integration of Gene Expression Profiling and Clinical Variables to Predict Prostate Carcinoma Recurrence After Radical Prostatectomy," *Cancer*, 104:290-8, (2005).
Stewart, "Lung Carcinoma in African Americans, a Review of the Current Literature," *Cancer*, 91(12):2476-2482, (Jun. 15, 2001).
Swensen, et al., "Solitary pulmonary nodules: clinical prediction model versus physicians," *Mayo Clinic. Proc.*, 74:319-29, Abstract (1999).
Swensen, et al., "The Probability of Malignancy in Solitary Pulmonary Nodules. Application to Small Radiologically Indeterminate Nodules," *Arch. Intern. Med.*, 157:849-55, (1997).
Takizawa, et al. "Increased Expression of Transforming Growth Factor-Beta1 in Small Airway Epithelium From Tobacco Smokers and Patients With Chronic Obstructive Pulmonary Disease (COPD)," *American Journal of Respiratory and Critical Care Medicine*, 163:1476-1483, (2001).
Tarca, et al., "Analysis of Microarray Experiments of Gene Expression Profiling", *Am J, Obstet, Gynecol,*, 195(2):373-388, (2006).
Theocharis, et al., "Metallothionein: A Multifunctional Protein From Toxicity to Cancer," *Int. Biol. Markers*, 18(3):162-169, (2003).
Thisted, "What is a P-value," Departments of Statistics and Health Studies, The University of Chicago, May 25, 1998.
Thurston, et al., "Modeling Lung Cancer Risk in Case-Control Studies Using a New Dose Metric of Smoking," *Cancer Epidemiol Biomarkers Prev.*, 14(10):2296-302, (2005).
Tichelaar, et al., "Increased Staining for Phospho-Akt, p65/RELA and cIAP-2 in Pre-neoplastic Human Bronchial Biopsies," *BMC Cancer*, 5(155):1-13, (2005).
Trunk, et al., "The Management and Evaluation of the Solitary Pulmonary Nodule," *Chest*, 66:236-9, (1974).
Tsao, et al, "Increased Phospho-AKT (Ser$^{473}$) Expression in Bronchial Dysplasia: Implications for Lunch Cancer Prevention Studies," *Cancer, Epidemiology, Biomarkers & Prevention*, 12:660-664, (2003).
Ung, et al., "Fluorodeoxyglucose Positron Emission Tomography in the Diagnosis and Staging of Lung Cancer: A Systematic Review," *J. Nat'l. Cancer Institute*, 99(23):1753-67, (2007).
Volm, et al., "Prognostic Significance of the Expression of C-Fos, C-Jun and C-Erbb-1 Oncogene Products in Human Squamous Cell Lung Carcinomas," *J, Cancer Res. Clin. Oncol.*, 119:507-510, (1993).
Voynow, et al., "Mucin Gene Expression (MUC1, MUC2, and MUC5/5AC) in Nasal Epithelial Cells of Cystic Fibrosis, Allergic Rhinitis, and Normal Individuals," *Lung*, 176:345-354, (1998).
Wahidi, et al., "Evidence for the Treatment of Patients With Pulmonary Nodules: When Is It Lung Cancer? ACCP Evidence-Based Clinical Practice Guidelines 2$^{nd}$ Edition," *Chest*, 132:94-107S, (2007).
Wardlaw, et al., "Effect of Cigarette Smoke on CYP1A1, CYP1A2 and CYP2B1/2 of Nasal Mucosae in F344 Rats," *Carcinogenesis*, 19(4):655-662, (1998).
Watters, et al. "Developing Gene Expression Signatures of Pathway Deregulation in Tumors," *Molecular Cancer Therapeutics*, 5:2444-2449, (2006).
West, et al, "Rapid Akt Activation by Nicotine and Tobacco Carcinogen Modulates the Phenotype of Normal Human Airway Epithelial Cells," *The Journal of Clinical Investigation*, 111(1):81-90, (2003).
West, et al., "Embracing the Complexity of Genomic Data for Personalized Medicine," *Genome Res.*, 16:559-66, (2006).
Whitehead, et al., "Variation in Tissue-Specific Gene Expression Among Natural Populations," *Genome Biology*, 6(2):R13.1-R13.14, (2005).
Willey, et al., "Quantitative RT-PCR Measurement of Cytochromes p450 1A1, 1B1, and 2B7, Microsomal Epoxide Hydrolase, and NADPH Oxidoreductase Expression in Lung Cells of Smokers and Nonsmokers," *Am. J. Respir. Cell Mol. Biol.*, 17:114-124, (1997).
Wistuba, et al., "High Resolution Chromosome 3p Allelotyping of Human Lung Cancer and Preneoplastic/Preinvasive Bronchial Epithelium Reveals Multiple, Discontinuous Sites of 3p Allele Loss and Three Regions of Frequent Breakpoints." *Cancer Res.*, 60(7):1949-60, (Apr. 1, 2000).
Wistuba, et al., "Molecular Damage in the Bronchial Epithelium of Current and Former Smokers," *J. Natl. Cancer Inst.*, 89(18):1366-73, (Sep. 17, 1997).
Woenckhaus, et al., "Expression Profiling of Non-Small Cell Lung Cancers and Bronchi of Smokers and Non Smokers," *Study Group: Molecular Pathology/Pathology—Research and Practice*, 200:p. 255, (2004).
Woenckhaus, et al., "Smoking and Cancer-Related Gene Expression in Bronchial Epithelium and Non-Small-Cell Lung Cancers," *Journal of Pathology*, 210:192-204, (2006).
Wojnarowski et al., "Cytokine Expression in Bronchial Biopsies of Cystic Fibrosis Patients With and Without Acute Exacerbation," *Eur. Respir. J.*, 14:1136-1144, (1999).
Wu, "Analysing Gene Expression Data From DNA Microarrays to Identify Candidate Genes," *Journal of Pathology*, 195:53-65, (2001).
Yoneda, et al., "Development of High-Density DNA Microarray Membrane for Prfiling Smoke-and Hydrogen Peroxide-Induced Genes in a Human Bronchial Epithelial Cell Line," American Journal of Respiratory and Critical Care Medicine, 164:S86-S89, (2001).
Yu-Rong, et al., "Tumor Associated Antigen L6 and the Invasion of Human Lung Cancer Cells," *Clinical Cancer Research* 9(7):2807-16, (2003).
Zeeberg, et al.. "Gominer: A Resource for Biological Interpretation of Genomic and Proteomic Data," *Genome Biology*, 4(4):R28.1-R28.8, (2003).
Zhang, et al., "Comparison of Smoking-Induced Gene Expression on Affymetrix Exon and 3'-Based Expression Arrays," *Genome Inform.*, 18:247-57, (2007).
Beane-Ebel, "Single-Cell RNA Sequenceing of the Bronchial Epithelium in Smokers With Lung Cancer," U.S. Army Medical Research and Material Command. Jul. 1, 2016 [retrieved on Sep. 19, 2017]. Retrieved from the Internet at http://www.dtic.mil/dtic/tr/fulltext/u2/a624219.pdf.
Durham, et al., "The Relationship Between COPD and Lung Cancer," *Lung Cancer*, 90:121-127, (2015).
Kocarnik, et al., "Replication of Associations Between GWAS SNPs and Melanoma Risk in the Population Architecture Using Genomics and Epidemiology (PAGE) Study," *Journal of Investigative Dermatology*, 134:2049-2052, (Feb. 27, 2014).
Ooi, et al., "Molecular Profiling of Premalignant Lesions in Lung Squamous Cell Carcinomas Identifies Mechanisms Involved in Stepwise Carcinogenesis," *Cancer Prevention Research*, 7(5):487-495, (Mar. 11, 2014).
European Search Report for Application EP08832403, dated Oct. 22, 2010.
European Search Report for Application EP09724548, dated Jun. 16, 2011.
European Search Report for Application EP10195816, dated Oct. 13, 2011.
Chinese Search Report for Application CN2008801147951, dated Aug. 24, 2012.

(56) References Cited

OTHER PUBLICATIONS

European Search Report for Application EP10195822, dated Jun. 20, 2011.
European Search Report for Application EP10195803, dated Jun. 20, 2011.
European Search Report for Application EP10184732, dated Mar. 21, 2011.
European Search Report for Application EP10184813, dated Mar. 21, 2011.
European Search Report for Application EP10184888, dated Mar. 21, 2011.
European Search Report for Application EP04810818, dated Oct. 28, 2010.
European Search Report for Application EP12170635, dated Apr. 22, 2013.
Extended European Search Report from EP 16186152.1, dated May 31, 2017.
International Search Report for PCT/US2017/032517, dated Oct. 2, 2017.
International Search Report for PCT/US2017/041267, dated Dec. 15, 2017.
Non-Final Office Action for U.S. Appl. No. 12/234,588, dated Jun. 27, 2011.
Non-Final Office Action for U.S. Appl. No. 10/579,376, dated Jul. 9, 2008.
Non-Final Office Action for U.S. Appl. No. 12/884,714, dated Sep. 23, 2011.
Final Office Action for U.S. Appl. No. 12/234,588, dated Nov. 4, 2011.
Non-Final Office Action for U.S. Appl. No. 12/414,555, dated Nov. 30, 2011.
Final Office Action for U.S. Appl. No. 12/414,555, dated Mar. 15, 2012.
Non-Final Office Action for U.S. Appl. No. 13/346,444, dated Dec. 12, 2012.
Non-Final Office Action for U.S. Appl. No. 12/234,588, dated Mar. 28, 2014.
Final Office Action for U.S. Appl. No. 13/346,444, dated Nov. 27, 2013.
Non-Final Office Action for U.S. Appl. No. 11/294,834, dated Jan. 29, 2014.
Non-Final Office Action for U.S. Appl. No. 14/584,960, dated Apr. 27, 2016.
Final Office Action for U.S. Appl. No. 13/524,749, dated Apr. 3, 2014.
Final Office Action for U.S. Appl. No. 13/323,655, dated Jul. 17, 2014.
Final Office Action for U.S. Appl. No. 11/294,834, dated Aug. 22, 2016.
Non-Final Office Action for U.S. Appl. No. 11/294,834, dated Dec. 15, 2015.
Non-Final Office Action for U.S. Appl. No. 11/294,834, dated Jun. 24, 2008.
Non-Final Office Action for U.S. Appl. No. 13/323,655, dated Apr. 9, 2013.
Non-Final Office Action for U.S. Appl. No. 13/524,749, dated Sep. 9, 2013.
Final Office Action for U.S. Appl. No. 11/294,834, dated Aug. 18, 2014.
Non-Final Office Action for U.S. Appl. No. 13/323,655, dated Nov. 7, 2013.
Non-Final Office Action for U.S. Appl. No. 14/613,210, dated Dec. 6, 2016.
Final Office Action for U.S. Appl. No. 14/500,475, dated Feb. 28, 2017.
Final Office Action for U.S. Appl. No. 14/613,210, dated Apr. 3, 2017.
Final Office Action for U.S. Appl. No. 14/500,475, dated Aug. 2, 2017.
Notice of Allowance for U.S. Appl. No. 14/613,210, dated Oct. 31, 2017.
Chan, "Integrating Transcriptomics and Proteomics," *Drug Discovery & Development*, pp. 1-4, dated Apr. 1, 2006.
Coleman, "Of Mouse and Man—What is the Value of the Mouse in Predicting Gene Expression in Humans?" *Drug Discovery Today*, 8(6):233-235, (Mar. 2003).
Cooper, "Gene Expression Studies in Lung Cancer," *The Molecular Genetics of Lung Cancer*, pp. 167-186, (2005).
Deng, et al., "Ubiquitous Induction of Resistance to Platinum Drugs in Human Ovarian, Cervical, Germ-Cell and Lung Carcinoma Tumor Cells Overexpressing Isoforms 1 and 2 of Dihydrodiol Dehydrogenase," *Cancer Chemother. Pharmacol.*, 54:301-307, (2004).
Schulz, et al., "Activation of Bronchial Epithelial Cells in Smokers Without Airway Obstruction and Patients with COPD," *Chest*, 125(5):1706-1713, (May 2004).
Su, et al., "Molecular Classification of Human Carcinomas by Use of Gene Expression Signatures," *Cancer Research*, 61:7388-7393, (Oct. 15, 2001).
Yang, et al., "Reduction of Dihydrodiol Dehydrogenase Expression in Resected Hepatocellular Carcinoma," *Oncol. Rep.*, 10(2):271-276, Abstract pp. 1-2 (2003).
Non-Final Office Action for U.S. Appl. No. 14/500,475, dated Mar. 26, 2018.
Non-Final Office Action for U.S. Appl. No. 14/690,182, dated Apr. 20, 2018.
Non-Final Office Action for U.S. Appl. No. 15/336,469, dated Apr. 10, 2018.
Non-Final Office Action for U.S. Appl. No. 15/888,831, dated Mar. 27, 2018.
Zochbauer-Muller, et al., "5' CpG Island Methylation of the FHIT Gene is Correlated with Loss of Gene Expression in Lung and Breast," *Cancer Research*, 61:3581-3585, (May 2, 2001).
European Search Report for European Application No. EP 17185133.0, dated Feb. 21, 2018.
Final Office Action for U.S. Appl. No. 15/439,891, dated Feb. 14, 2018.
Kuriakose, et al., "Selection and Validation of Differentially Expressed Genes in Head and Neck Cancer," *CMLS*, 61:1372-1383, (2004).
Sugita, et al., "Combined Use of Oligonucleotide and Tissue Microarrays Identifies Cancer/Testis Antigens as Biomarkers in Lung Carcinoma," *Cancer Research*, 62:3971-3979, (Jul. 15, 2002).
Vartiainen, et al., "Validation of Self Reported Smoking by Serum Cotinine Measurement in a Community-Based Study," *J. Epidemiol Community Health*, 56:167-170, (2002).
Zhang, et al., "Similarities and Differences Between Smoking-Related Gene Expression in Nasal and Bronchial Epithelium," *Physiol. Genomics*, 41:1-8, (2010).
Final Office Action for U.S. Appl. No. 15/336,469, dated Oct. 9, 2018.
Final Office Action for U.S. Appl. No. 14/690,182, dated Oct. 9, 2018.
Final Office Action for U.S. Appl. No. 15/888,831, dated Jul. 24, 2018.
Elisabeth Brambilla, et al., "p53 Mutant Immunophenotype and Deregulation of p53 Transcription Pathway (Bc12, Bax, and Waf1) in Precursor Bronchial Lesions of Lung Cancer", Clinical Cancer Research, vol. 4, Jul. 1, 1998 (Jul. 1, 1998), pp. 1609-1618.
Anonymous: "Bronchogenic carcinoma is a malignant neoplasm of the lung arising from the epithelium of the bronchus or bronchiole", Apr. 22, 2003 (Apr. 22, 2003), retrieved from the internet: URL:http://www.meddean.luc.edu/lumen/meded/medicine/pulmonar/pathms/path19.htm [retrieved on Feb. 13, 2019].
Brenner, Sydney, et al. "Gene expression analysis by massively parallel signature sequencing (MPSS) on microbead arrays" Nature biotechnology 18 (2000), pp. 630-634.
Anonymous: "Bronchogenic carcinoma / definition of bronchogenic carcinoma by Medical dictionary," Feb. 13, 2019 (Feb. 13, 2019), retrieved from the internet: URL:https://medical-dictionary.thefreedictionary.com/bronchogenic+carcinoma [retrieved on Feb. 13, 2019].
Non-Final Office Action for U.S. Appl. No. 14/690,182, dated Mar. 22, 2019.

(56) References Cited

OTHER PUBLICATIONS

Non-Final Office Action for U.S. Appl. No. 15/888,831, dated Mar. 27, 2019.
Final Office Action for U.S. Appl. No. 14/500,475, dated May 14, 2019.
Final Office Action for U.S. Appl. No. 15/439,891, dated Jun. 18, 2019.
Perez-Rogers et al "/Poster Discussion Session/ Sunday, May 18 / 2:00-4:30 PM / Room 30 A-B (Upper Level) San A107 The Lung's Silver Lining: Airway and Alevolar Epithelial Biology Leveraging Gene Expression in the Bronchial Airway to Deelop a Nasal Biomarker for Early Detection of Lung Cancer," retrieved from the Internet: URL:https://www.atsjournals.org/doi/pdf/10.1164/ajrccm-conference.2014.189.1_MeetingAbstract.A2362 (2014).
Chen, et al., "Expression of dihydrodiol dehydrogenase in the resected state I non-small cell lung cancer," Oncology Reports, vol. 9, No. 3, May 1, 2002, pp. 515-519.
Hsu, et al., "Overexpression of dihydrodiol dehydrogenase as a prognostic maker of non-small cell lung cancer," Cancer Research vol. 6, No. 6, Mar. 15, 2001, pp. 2727-2731.
Shibuya, Kiyoshi, et al. "Increased telomerase activity and elevated hTERT mRNA expression during multistage carcinogenesis of squamous cell carcinoma of the lung." Cancer 92.4 (2001): 849-855.
Tockman, Melvyn S., et al. "Considerations in bringing a cancer biomarker to clinical application." Cancer Research 52.9 Supplement (1992): 2711s-2718s.
Spira, et al., Translating Airway Gene Expression into Biomarkers for Tobacco Smoke Exposure and Lung Cancer Detection Smoking and the Airway "filed of Injury" as a Paradigm. Retrieved from the internet: URL: https://www.epa.gov/sites/production/files/2014-07/documents/spiraavrum_epa_dec_2012.pdf.
Supplementary European Search Report for European Application No. EP 17 79 6983, dated Feb. 3, 2020.
Final Office Action for U.S. Appl. No. 15/888,831, dated Oct. 10, 2019.
Notice of Allowance for U.S. Appl. No. 14/500,475, dated Oct. 15, 2019.
Non-final office action for U.S. Appl. No. 15/336,469 dated Dec. 4, 2019.
Non-Final Office Action for U.S. Appl. No. 16/510,584 dated Jan. 16, 2020.
Notice of Allowance issued in U.S. Appl. No. 15/888,831, dated Feb. 20, 2020.
Final Office Action for U.S. Appl. No. 16/510,584, dated Apr. 23, 2020.
Notice of Allowance Issued in U.S. Appl. No. 15/888,831, dated Jun. 1, 2020.
Final Office Action issued in U.S. Appl. No. 15/336,469, dated Jul. 10, 2020.
Non Final Office Action issued in U.S. Appl. No. 16/810,827, dated Aug. 10, 2020.
Non Final Office Action issued in U.S. Appl. No. 16/510,584, dated Sep. 30, 2020.
Non-Final Office Action Issued in U.S. Appl. No. 16/300,947, dated Oct. 22, 2020.

\* cited by examiner

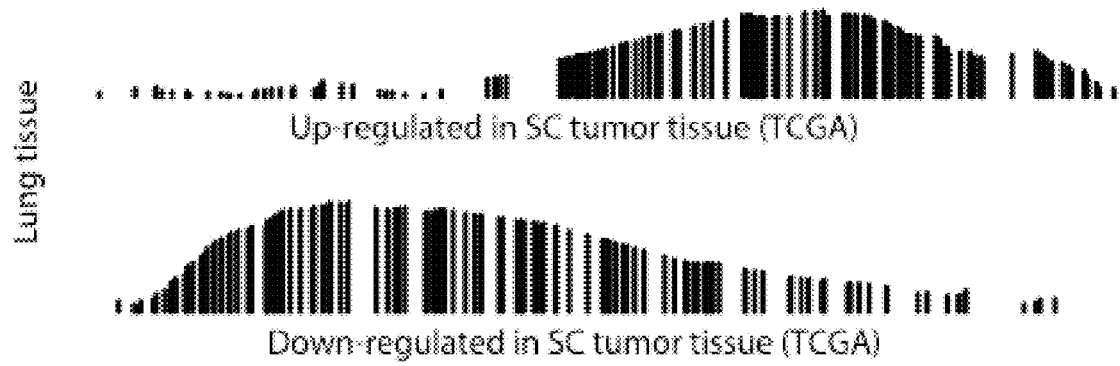
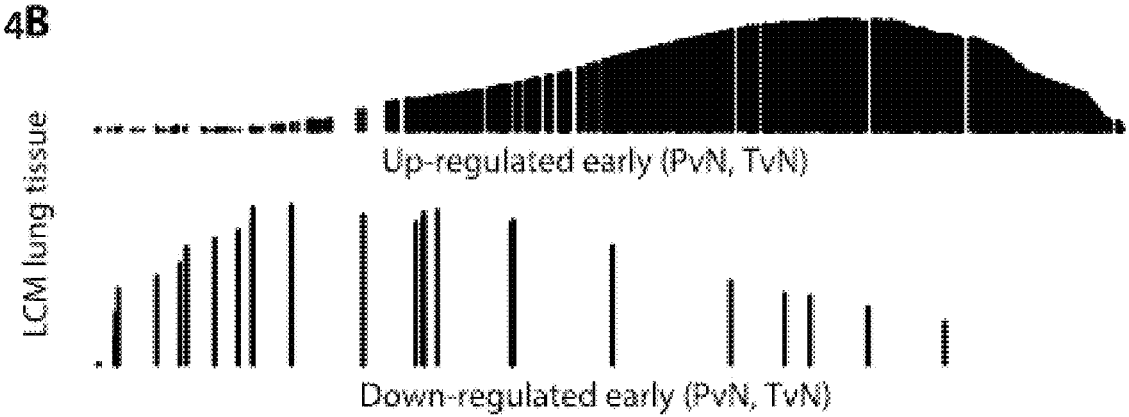
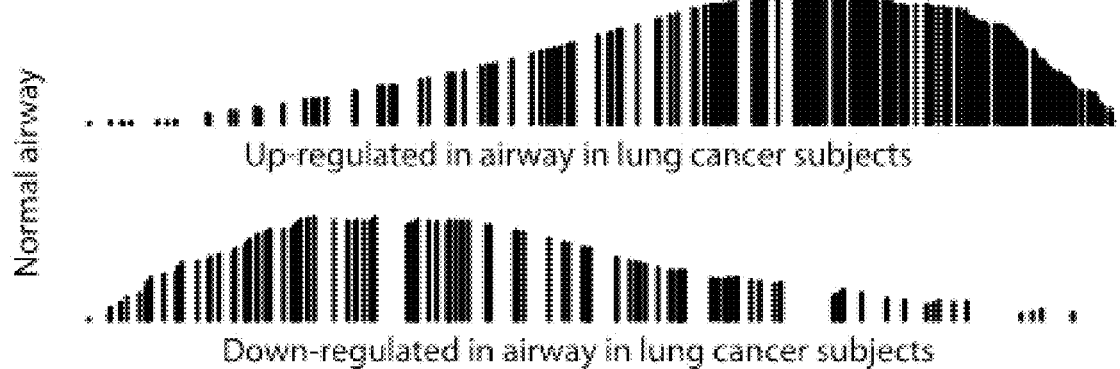
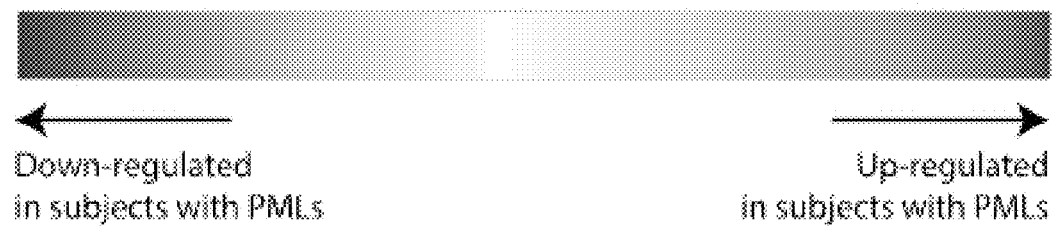
FIGS. 4A-4C

GENE EXPRESSION-BASED BIOMARKER FOR THE DETECTION AND MONITORING OF BRONCHIAL PREMALIGNANT LESIONS

CROSS-REFERENCE TO RELATED APPLICATIONS

This application claims the benefit of U.S. Provisional Application No. 62/360,218, filed on Jul. 8, 2016, the contents of which are hereby incorporated by reference in its entirety.

BACKGROUND OF THE INVENTION

Lung cancer (LC) is the leading cause of cancer death in the United States. The molecular events preceding the onset of LC and the progression of premalignant lesions (PMLs) to lung cancer are poorly understood. This is due in part to the lack of reliable biomarkers which complicates the study of such lesions. Currently there are no molecular tests to identify PMLs or describe their changes over time. The only technology that is able to visualize and sample premalignant lesions is auto-fluorescent bronchoscopy, which is limited in sensitivity and is not in widespread clinical use.

Needed are novel biomarkers, methods and assays that are capable of facilitating the evaluation of PMLs. Suspicious lesions on chest computed tomography (CT) scans typically prompt bronchoscopic evaluation, which is also limited by varying diagnostic yields. Moreover, negative bronchoscopies prove a clinical dilemma, whereby the need to provide a diagnostic answer is countered by the invasiveness of follow-up studies.

A previously reported biomarker, PERCEPTA® (Veracyte Inc.), has demonstrated the potential benefit of employing a bronchial gene expression-based classifier on a sub-set of patients with non-diagnostic bronchoscopies, through modifying risk stratification of patients. However, this biomarker has demonstrated greatest benefit amongst those with a moderate pre-test probability with modest overall sensitivities. The employment of a novel pre-malignancy marker would complement the PERCEPTA® biomarker in this sub-set of patients, facilitating the identification of those patients that would be at high risk for PML progression.

Also needed are new biomarkers, methods and assays for use in lung cancer screening assays and the early detection of PMLs. A recent large randomized controlled trial has led to the recent endorsement of annual lung cancer screening with low dose CT for asymptomatic patients that are at higher lung cancer risk. This has created a large volume of chest CTs, whose performance is marred by the high rate of false positive results. It is anticipated that this will lead to a large need for invasive procedures for benign disease. A pre-malignancy biomarker could complement the diagnostic work up of lesions identified through screening, which are typically more complicated since such lesions identified on screening are usually smaller and more complex. Additionally, patient screening eligibility is based solely on epidemiological and demographic considerations, which still vary between different proposed guidelines. This leads to varying referral patterns and missed opportunities to screen a large proportion of those patients with high risk that do not meet dictated criteria. The availability of biomarkers, methods and assays for the detection of PMLs would overcome this challenge by facilitating the identification of pre-malignancy-associated changes and risk of progression, would provide a first step to identifying molecular risk factors for lung cancer, and would identify those patients who would benefit from CT screening. Such biomarkers would also be useful for patent risk stratification, which would assist in the identification of those patients that may benefit from additional screening of those patients harboring premalignant molecular alterations, which could in turn inform future decision making.

The limited understanding of the mechanisms involved in transforming PMLs into LC has restricted the ability to intervene in these processes, making the identification of chemoprevention agents difficult in view of the challenges involved in discerning premalignant phenotypes through currently available means. Furthermore, clinical trials in this space are exceedingly difficult given the long duration required to detect significant outcome benefits. Accordingly, biomarkers, assays and methods that are reflective of pre-malignancy would facilitate "smart" patient enrollment for trials and would allow accounting for molecular heterogeneity involved in random patient recruitment in such trials.

SUMMARY OF THE INVENTION

The present inventions provide insight into the mechanisms that are involved in the transformation or progression of premalignant bronchial lesions into lung cancer. Provided herein are novel biomarkers, methods and assays that are useful in lung cancer screening and the early detection of premalignant lesions (PMLs). The biomarkers, methods and assays of the present invention also facilitate the monitoring of PMLs and their progression or regression over time. Advantageously, the assays and methods disclosed herein may be rapidly performed in a non-invasive or minimally-invasive manner, providing objective results, contributing to the identification and monitoring of subjects that are suspected of having PMLs, facilitating the clinical decision making of the treatment of such subjects and informing clinical trial recruitment efforts.

In certain aspects, the biomarkers, methods and assays disclosed herein may be assessed or performed on a biological sample that is obtained from a subject at a site that is distal to the suspected site of the premalignant bronchial lesion. For example, in certain embodiments, the assays and methods of determining the presence of PMLs or cancer in the lungs may be performed by determining the expression of one or more genes in nasal or buccal epithelial cells and/or tissues. Similarly, such assays and methods may be performed by determining the expression of one or more genes in the subject's peripheral blood cells. In certain aspects, the biomarkers, methods and assays disclosed herein may be assessed or performed on, or additionally include, a biological sample that is obtained from a subject with a positive result in an imaging study (e.g., chest X-ray, CT scan, etc.). In some aspects, the methods and assays disclosed herein can comprise a step of performing an imaging study. In certain aspects, the biomarkers, methods and assays disclosed herein may be assessed or performed on, or additionally include, a biological sample that is obtained from a subject with a positive result in an imaging study (e.g., chest X-ray, CT scan, etc.) to confirm or rule out the positive result. In some aspects, the methods or assays disclosed herein are used to determine whether a positive result in an imaging study warrants a further invasive procedure (e.g., bronchoscopy), chemoprophylaxis, and/or chemotherapy.

In some embodiments, methods and assays disclosed herein may be assessed or performed on a biological sample that is obtained from a subject at a suspected site of a PML (e.g., premalignant bronchial lesion). In some embodiments, the suspected site is identified as having abnormal fluorescent during auto-fluorescence bronchoscopy, although the method of identifying the suspected site is not limited. In some embodiments, the methods and assays disclosed herein may be performed on a biopsy of a suspected PML as an alternative to, or in addition to, a histological examination of the biopsy.

In certain aspects, disclosed herein are methods of determining the presence or absence of a premalignant lesion in a subject. Such methods comprise the steps of: (a) measuring a biological sample comprising airway epithelial cells of the subject for expression of one or more genes; and (b) comparing the expression of the one or more genes to a control sample of those genes from individuals without premalignant lesions; wherein the one or more genes are selected from the group consisting of genes in Table 3, and wherein differential expression of the subject's one or more genes relative to the control sample is indicative of the presence of a premalignant lesion in the subject. Similarly, in certain embodiments, non-differential expression of the subject's one or more genes relative to the control sample is indicative of the absence of a premalignant lesion in the subject.

Also disclosed herein are methods of determining the likelihood that a premalignant lesion in a subject will progress to lung cancer. In certain aspects, such methods comprise the steps of: (a) measuring a biological sample comprising airway epithelial cells of the subject for expression of one or more genes; and (b) comparing the expression of the one or more genes to a control sample of those genes from individuals with lung cancer; wherein the one or more genes are selected from the group consisting of genes in Table 3, and wherein differential expression of the subject's one or more genes relative to the control sample is indicative of a low likelihood of the premalignant lesion progressing to lung cancer. In some embodiments, non-differential expression of the subject's one or more genes relative to the control sample is indicative of a high likelihood of the premalignant lesion progressing to lung cancer.

In certain embodiments, also disclosed herein are methods of monitoring whether a premalignant lesion will progress to lung cancer in a subject. Such methods comprise subjecting a biological sample comprising airway epithelial cells of the subject to a gene expression analysis, wherein the gene expression analysis comprises comparing gene expression levels of one or more genes selected from the group of genes in Table 3 to the expression levels of a control sample of those genes from individuals with cancer, and wherein differential expression of the subject's one or more genes relative to the control sample is indicative of a lack of progression of the premalignant lesion to lung cancer. Similarly, in certain aspects non-differential expression of the subject's one or more genes relative to the control sample is indicative of progression of the premalignant lesion to lung cancer.

In yet other embodiments, also disclosed herein are methods of determining the presence of a premalignant lesion in a subject comprising the steps of: (a) measuring a biological sample comprising airway epithelial cells of the subject for expression of one or more genes; and (b) comparing the expression of the one or more genes to a control sample of those genes obtained from individuals without premalignant lesions; wherein the one or more genes are selected from the group of genes in at least one pathway in Dataset 2, and wherein differential expression of the subject's one or more genes relative to the control sample is indicative of the presence of a premalignant lesion in the subject. In some embodiments, non-differential expression of the subject's one or more genes relative to the control sample is indicative of the absence of a premalignant lesion in the subject.

In certain aspects of any of the foregoing methods, at least two genes, at least five genes, at least ten genes, at least twenty genes, at least thirty genes, at least forty genes, at least fifty genes, at least one hundred genes, at least two hundred genes or at least two hundred and eighty genes are measured. In some embodiments of the foregoing methods, the one or more genes comprise those genes associated with a pathway identified in Dataset 2.

In some embodiments of any of the foregoing methods the airway epithelial cells comprise bronchial epithelial cells. In certain aspects, such bronchial epithelial cells are obtained by brushing the bronchi walls of the subject. In certain aspects of any of the foregoing methods, the airway epithelial cells comprise nasal epithelial cells. In certain aspects of any of the foregoing methods, the airway epithelial cells comprise buccal epithelial cells. In still other embodiments of the present inventions, the airway epithelial cells do not comprise bronchial epithelial cells. In some embodiments, the airway epithelial cells are obtained from a suspected PML site (e.g., abnormal fluorescing areas during auto-fluorescence bronchoscopy).

In certain aspects, the methods disclosed herein are performed with, or further comprise assessing or determining one or more of the subject's secondary factors that affect the subject's risk for having or developing lung cancer. For example, in some embodiments, one or more secondary factors are selected from the group consisting of advanced age, smoking status, the presence of a lung nodule greater than 3 cm on CT scan and time since quitting smoking. In certain embodiments of the foregoing methods, expression of the one or more genes is determined using a quantitative reverse transcription polymerase chain reaction, a bead-based nucleic acid detection assay or an oligonucleotide array assay.

The foregoing methods are useful for predicting or monitoring the progression of PMLs to lung cancer. For example, a lung cancer selected from the group consisting of adenocarcinoma, squamous cell carcinoma, small cell cancer or non-small cell cancer.

In some embodiments, the one or more genes comprise mRNA and/or microRNA. In some embodiments, the differential expression is determined by reverse transcribing one or more RNAs of the one or more genes into cDNA in vitro. In some aspects, the one or more genes comprise cDNA. In yet other embodiments, the one or more genes are labeled prior to the measuring.

The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3A shows the mean baseline OCR/ECAR ratio measured in human bronchial biopsies cultures from PMLs (pink, n=6) was 2.5 fold higher than the biopsies of normal airway epithelium (gray n=6) (p=0.035). Error bars represent standard error of the mean. FIG. 3B shows bioenergetic studies testing mitochondrial function demonstrate PMLs (pink) have a significantly (~1.5 fold) higher maximal respiration (p=0.022). Error bars represent standard error of the mean. FIG. 3C and FIG. 3D show mitochondrial enumeration by FACS analysis of MitoTraker GFP suggests increased OCR is not reliant on increase mitochondria as the difference in GFP per cell was not significant (p=0.150). FIG. 3E shows representative images of TOMM22 and COX IV staining in which expression of both proteins is increased in low and moderate dysplastic lesions in both human and NTCU-mouse PMLs. (Magnification 400x).

FIGS. 4A-4C shows that PML-associated gene expression alterations in the field are concordant with SCC-related datasets. The genes up-regulated in the field of subjects with PMLs are red and genes down regulated in blue. GSEA identified the significant enrichment of the lung cancer-related gene expression signatures shown in this ranked list. The black vertical lines represent the position of the genes in the gene set in the ranked list and the height corresponds to the magnitude of the running enrichment score from GSEA. FIG. 4A shows top differentially expressed genes from analysis of TCGA RNA-Seq data comparing lung SCC and matched adjacent normal tumor tissue. FIG. 4B shows Ooi et al. gene sets for early gene expression changes defined by genes altered between premalignant and normal tissue and between tumor and normal tissue (p<0.05) using laser capture microdissected (LCM) epithelium from the margins of resected SCC tumors. FIG. 4C shows top differentially expressed genes from analysis of cytologically normal bronchial epithelial cells from smokers with and without lung cancer (GSE4115).

FIG. 5A is a ROC curve (AUC=0.92) showing biomarker performance based on predictions of the presence of PMLs in the validation samples (n=17), red line. Shuffling of class labels (n=100 permutations) produced an average ROC curve (black line) with a significantly lower AUC (p<<0.001). FIG. 5B is a ROC curve (AUC=0.75) showing biomarker performance based on changes in biomarker score over time in detecting PML regression or stable/progression.

FIG. 7A shows GSVA scores were calculated based on genes in KEGG OXPHOS pathway and KEGG, Biocarta, and Reactome Glycolysis pathways in the CCLE cell lines highlighting the H1229 (green) (high OXPHOS and moderate glycolysis), SW900 (red) (moderate OXPHOS and low glycolysis) and H2805 (blue) ((low OXPHOS and moderate glycolysis). FIG. 7B shows baseline OCR/ECAR ratio values for the cancer cells lines demonstrating the relationship between elevated OXPHOS GSVA scores and oxygen consumption. FIG. 7C shows elevation of respiratory capacity associated with high OXPHOS gene score in response to mitochondrial perturbation. FIG. 7D shows elevated ECAR response in the H1299 and H205 is associated with the moderate glycolysis GSVA score, however, although the SW900 glycolysis GSVA scores agree with baseline ECAR, in the state of repressed OXPHOS, glycolysis is activated. FIG. 7E shows enumeration of mitochondria within each cancer cell suggests that increased GSVA scores for OXPHOS or glycolysis did not correlate with mitochondrial number. H2085 cells had the lowest OXPHOS GSVA score, the lowest basal OCR, and the lowest respiratory capacity, but their mitochondrial content was significantly greater that H1299 and SW900 (p=0.03). FIG. 7F shows cell area (FSC-A) is correlated with mitochondrial number (fluorescence of MitoTracker Green FM). FIG. 7G shows GSVA scores were calculated based on genes in KEGG OXPHOS pathway. The GSVA scores for OXPHOS activity were significantly elevated in the airway field of subjects with PMLs compared to subjects without PMLs (p<0.01). FIG. 7H shows GSVA scores were calculated based on genes in the KEGG, Biocarta, and Reactome Glycolysis pathways. The mean GSVA scores were moderately elevated in the airway field of subjects with PMLs compared to subjects without PMLs.

Figure 9:
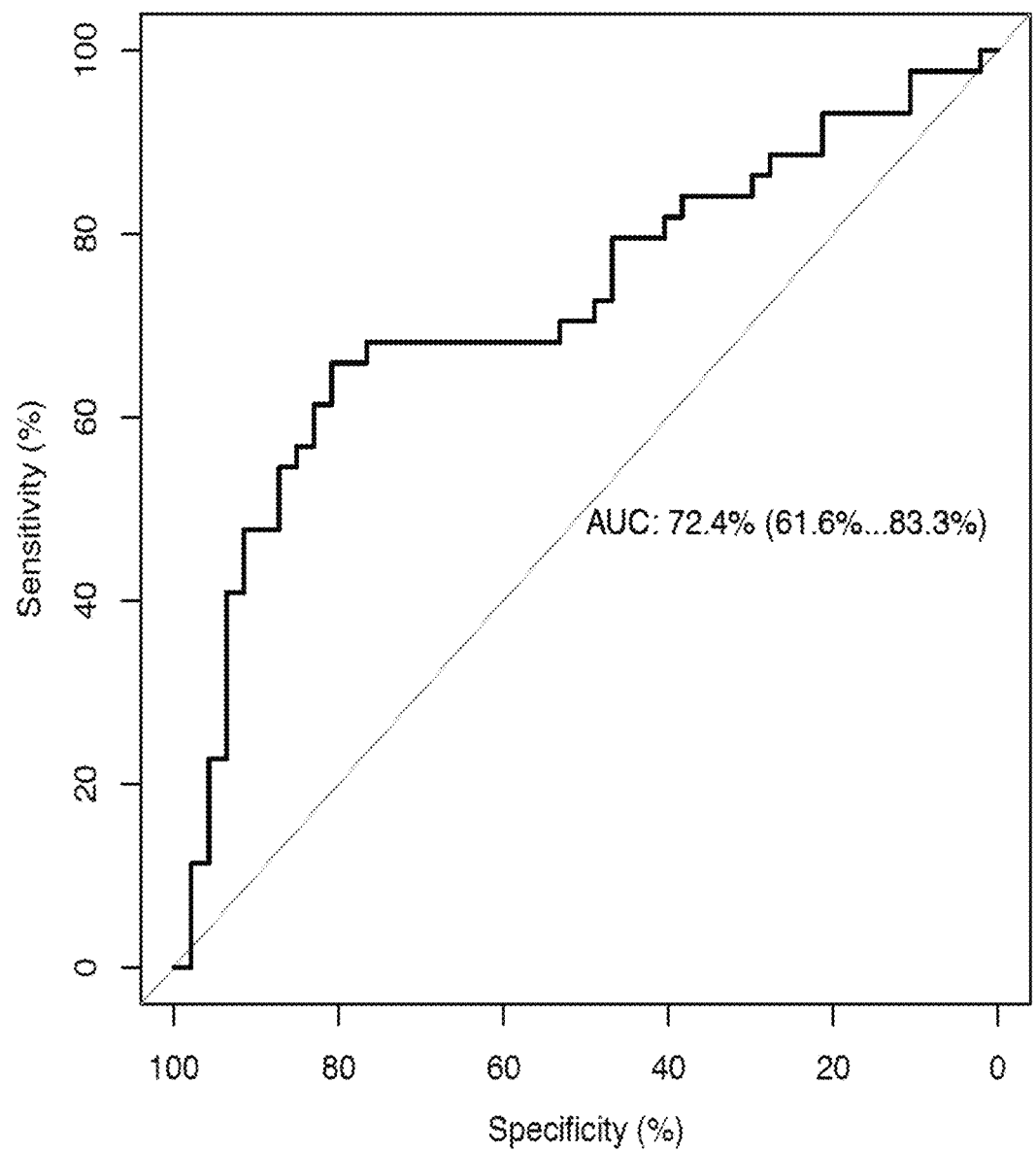

FIG. 9 shows that biomarker predicts dysplasia status in bronchial biopsies. ROC curve demonstrates the performance of the biomarker in distinguishing between premalignant lesion biopsies (severe=8, moderate=25, and mild dysplasia=14) and biopsies with normal histology (normal=24 and hyperplasia=20). Biomarker achieved AUC of 72% (with a 62%-83% confidence interval), sensitivity of 81% (38 of 47 dysplastic biopsies predicted correctly), and specificity of 66% (29 of 44 normal biopsies predicted correctly).

DETAILED DESCRIPTION OF THE INVENTION

Lung cancer develops in a sequenced manner. Patches of lung cells gain the ability to multiply faster than their neighboring normal cells by acquiring mutations and these patches of cells are called "premalignant lesions" or "PMLs." Some of these PMLs may progress to lung cancer. The inventions disclosed herein are based upon a biomarker that is capable of identifying and distinguishing epithelial cells from a person with lung cancer from normal epithelial cells. In particular, the inventions disclosed herein are based on the findings that exposure to carcinogens such as cigarette smoke induces smoking-related mRNA and microRNA expression alterations in the cytologically normal epithelium that lines the respiratory tract, creating an airway field of injury (1-8). Such gene expression alterations that were observed in the airway field of injury were used to develop a diagnostic test to facilitate early lung cancer lung cancer detection (9-12). Examination of gene signatures for p63 and the phosphatidylinositol 3-kinase (PI3K) pathway, revealed increased PI3K activation in the airway field of smokers with lung cancer or bronchial premalignant lesions (PMLs) (13). These results suggest the airway field of injury reflects processes associated with a precancerous disease state; however, the molecular changes have not been adequately characterized.

This is an important shortcoming because bronchial PMLs are precursors of squamous cell lung carcinoma, yet effective tools to identify smokers with PMLs at highest risk of progression to invasive cancer are lacking. Several studies report loss of heterozygosity, chromosomal aneusomy, and aberrant methylation and protein expression in bronchial PMLs (14-23). These molecular events can give rise to histological changes that can be reproducibly graded by a pathologist prior to the development of invasive carcinoma. Autofluorescence bronchoscopy can be used to detect and sample PMLs, which have a prevalence of approximately 9% for moderate dysplasia and 0.8% for carcinoma in situ (CIS) (24-26). The presence of high grade PMLs (severe dysplasia or CIS) is a marker of increased lung cancer risk in both the central and peripheral airways indicating the presence of changes throughout the airway field (27, 28).

The molecular characterization of the airway field of injury in smokers with PMLs disclosed herein provides novel insights into the earliest stages of lung carcinogenesis and identifies relatively accessible biomarkers to guide early lung cancer detection and early intervention. Accordingly, disclosed herein are novel biomarkers and gene expression signatures and related assays and methods that are able to provide information about the precancerous disease state and if this pre-cancerous disease state is progressing and/or regressing. Such biomarkers and the related assays and methods are useful for monitoring the progression of pre-malignant or pre-cancerous conditions in a subject by obtaining (e.g., non-invasively obtaining) a biological sample of epithelial cells from the respiratory tract of the subject (e.g., bronchial or nasal epithelial cells). In certain aspects, alterations in gene expression observed in epithelial cells that are distal to the lung tissues (e.g., nasal or buccal epithelial cells) are concordant with changes in the bronchial epithelium.

The present inventions represent a significant advance in the detection and monitoring of individuals with premalignant lesions (PMLs), particularly in comparison to the standard of care auto-fluorescence bronchoscopy techniques which are less sensitive. In addition to detecting and monitoring of PMLs, the present inventions provide means of advancing the identification of chemoprevention agents, which historically has been bounded by the difficulty of discerning premalignant phenotypes through currently available means. The present inventions further provide means of using gene expression profiling as a surrogate end point that complements both histological and marker end points used today, such as Ki67.

The biomarkers and related methods and assays disclosed herein are based in part upon the finding of a strong correlation between PMLs and the alterations in gene expression in tissues that are physically distant from the site of disease (e.g., the nasal epithelium). It has further been found that these biomarkers strongly predict whether a suspected PML is pre-malignant. The biomarkers, assays and methods disclosed herein are characterized by the accuracy with which they can detect and monitor lung cancer and their non-invasive or minimally-invasive nature. In some aspects, the assays and methods disclosed herein are based on detecting differential expression of one or more genes in airway epithelial cells and such assays and methods are based on the discovery that such differential expression in airway epithelial cells are useful for identifying and monitoring PMLs in the distant lung tissue. Accordingly, the inventions disclosed herein provide a substantially less invasive method for diagnosis, prognosis and monitoring of lung cancer using gene expression analysis of biological samples comprising airway epithelial cells.

In contrast to conventional invasive methods, such as auto-fluorescence bronchoscopy, the assays and methods disclosed herein rely on expression of certain genes in a biological sample obtained from a subject. As the phrase is used herein, "biological sample" means any sample taken or derived from a subject comprising one or more airway epithelial cells. As used herein, the phrase "obtaining a biological sample" refers to any process for directly or indirectly acquiring a biological sample from a subject. For example, a biological sample may be obtained (e.g., at a point-of-care facility, a physician's office, a hospital) by procuring a tissue or fluid sample from a subject. Alternatively, a biological sample may be obtained by receiving the sample (e.g., at a laboratory facility) from one or more persons who procured the sample directly from the subject.

Such biological samples comprising airway epithelial cells may be obtained from a subject (e.g., a subject suspected of having one or more PMLs or that is otherwise at risk for developing lung cancer) using a brush or a swab. The biological sample comprising airway epithelial cells may be collected by any means known to one skilled in the art and, in certain embodiments, is obtained in a non-invasive or minimally-invasive manner. For example, in certain embodiments, a biological sample comprising airway epithelial cells (e.g., nasal epithelial cells) may be collected from a subject by nasal brushing. Similarly, nasal epithelial cells may be collected by brushing the inferior turbinate and/or the adjacent lateral nasal wall. For example, following local anesthesia with 2% lidocaine solution, a CYROBRUSH® (MedScand Medical, Maimδ, Sweden) or a similar device, is inserted into the nare of the subject, for example the right nare, and under the inferior turbinate using a nasal speculum for visualization. The brush is turned (e.g., turned 1, 2, 3, 4, 5 times or more) to collect the nasal epithelial cells, which may then be subjected to analysis in accordance with the assays and methods disclosed herein.

In some embodiments, methods and assays disclosed herein may be assessed or performed on a biological sample that is obtained from a subject at a suspected site of a PML (e.g., premalignant bronchial lesion). In some embodiments, the suspected site is identified as having abnormal fluorescent during auto-fluorescence bronchoscopy, although the method of identifying the suspected site is not limited. In some embodiments, the methods and assays disclosed herein may be performed on a biopsy of a suspected PML as an alternative to, or in addition to, a histological examination of the biopsy.

In certain embodiments, the biological sample does not include or comprise bronchial airway epithelial cells. For example, in certain embodiments, the biological sample does not include epithelial cells from the mainstem bronchus. In certain aspects, the biological sample does not include cells or tissue collected from bronchoscopy. In some embodiments, the biological sample does not include cells or tissue isolated from a pulmonary lesion. In some embodiments, the biological sample does not include cells or tissue isolated from a PML.

To isolate nucleic acids from the biological sample, the airway epithelial cells can be placed immediately into a solution that prevents nucleic acids from degradation. For example, if the nasal epithelial cells are collected using the CYTOBRUSH, and one wishes to isolate RNA, the brush is placed immediately into an RNA stabilizer solution, such as RNALATER®, AMBION®, Inc. One can also isolate DNA. After brushing, the device can be placed in a buffer, such as phosphate buffered saline (PBS) for DNA isolation.

The nucleic acids (e.g., mRNA) are then subjected to gene expression analysis. Preferably, the nucleic acids are isolated and purified. However, if techniques such as microfluidic devices are used, cells may be placed into such device as whole cells without substantial purification. In one embodiment, airway epithelial cell gene expression is analyzed using gene/transcript groups and methods of using the expression profile of these gene/transcript groups in diagnosis and prognosis of lung diseases. In some embodiments, differential expression of the one or more genes determined with reference to the one or more of the 280 genes set forth in Table 3.

As used herein, the term "differential expression" refers to any qualitative or quantitative differences in the expression of the gene or differences in the expressed gene product (e.g., mRNA or microRNA) in the airway epithelial cells of the subject. A differentially expressed gene may qualitatively have its expression altered, including an activation or inactivation, in, for example, the presence of absence of cancer and, by comparing such expression in airway epithelial cell to the expression in a control sample in accordance with the methods and assays disclosed herein, and the presence or absence of PMLs may be determined and their progression or regression monitored.

In certain embodiments, the methods and assays disclosed herein are characterized as being much less invasive relative to, for example, bronchoscopy. The methods provided herein not only significantly increase the sensitivity or diagnostic accuracy of detecting and monitoring PMLs, but in certain aspects also make the analysis faster, much less invasive and thus much easier for the clinician to perform. In some embodiments, the likelihood that the subject has a PML or the likelihood that such a PML will progress to lung cancer is also determined based on the presence or absence of one or more secondary factors or diagnostic indicia of lung cancer, such as the subject's smoking history or status, or the results of previously performed imaging studies (e.g., chest CT scans). When the biomarkers, assays and methods of the present invention are combined with, for example, one or more relevant secondary factors (e.g., a subject's smoking history), the sensitivity and accuracy of detecting PMLs or their progression to lung cancer may be dramatically enhanced, enabling the detection of PMLs or their progression to lung cancer at an earlier stage, and by providing far fewer false negatives and/or false positives. As used herein, the phrase "secondary factors" refers broadly to any diagnostic indicia that would be relevant for determining a subject's risk of having or developing lung cancer. Exemplary secondary factors that may be used in combination with the methods or assays disclosed herein include, for example, imaging studies (e.g., chest X-ray, CT scan, etc.), the subject's smoking status or smoking history, the subject's family history and/or the subject's age. In certain aspects, when such secondary factors are combined with the methods and assays disclosed herein, the sensitivity, accuracy and/or predictive power of such methods and assays may be further enhanced. In some aspects, the methods and assays described herein are performed on a patient with a positive result in an imaging study (e.g., chest X-ray, CT scan, etc.). In some aspects, the methods or assays disclosed herein are used to confirm or rule out a positive result in an imaging study (e.g., chest X-ray, CT scan, etc.). In some aspects, the methods or assays disclosed herein are used to determine whether a positive result in an imaging study warrants a further invasive procedure (e.g., bronchoscopy), chemoprophylaxis, and/or chemotherapy.

The present inventors have discovered that PMLs and normal lung cells use different pathways to produce energy and survive and have harnessed this difference to develop the biomarker and related assays and methods disclosed herein. In some embodiments, the biological sample comprising the subject's airway epithelial cells (e.g., nasal or buccal epithelial cells) are analyzed for the expression of certain genes or gene transcripts corresponding to such metabolic pathways, either individually or in groups or subsets. In one embodiment, the inventions disclosed herein provide a group of genes corresponding to one or more pathways (e.g., metabolic pathways) that are significantly enriched in genes that are up- or down-regulated in the presence of PMLs (e.g., one or more pathways identified in Dataset 2) and that may be analyzed to determine the presence or absence of PMLs and/or their progression to lung cancer (e.g., adenocarcinoma, squamous cell carcinoma, small cell cancer and/or non-small cell cancer) from a biological sample comprising the subject's airway epithelial cells. For example, in certain aspects the biological sample may be analyzed to determine the differential expression of one or more genes from pathways involved in oxidative phosphorylation (OXPHOS), the electron transport chain (ETC), and mitochondrial protein transport to determine whether the subject has PMLs or is at risk of developing lung cancer. Other up-regulated pathways included DNA repair and the HIF1A pathway. Down-regulated pathways included the STAT3 pathway, the JAK/STAT pathway, IL-4 signaling, RAC1 regulatory pathway, NCAM1 interactions, collagen formation, and extracellular matrix organization.

In certain embodiments, the airway epithelial cells are analyzed using at least one and no more than 280 of the genes listed in Table 3. For example, about 1, about 2, about 3, about 4, about 5, about 6, about 7, about 8, about 9, about 10, about 10-15, about 15-20, about 20-30, about 30-40, about 40-50, at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, 210, 220, 230, 240, 250, 260, 270 or 275 or a maximum of the 280 genes as listed on Table 3.

Examples of the gene transcript groups useful in the diagnostic and prognostic assays and methods of the invention are set forth in Table 3. The present inventors have determined that taking any group that has at least about 5, 10, 15, 20, 25, 30, 40, 50, 60, 70, 80, 90, 100, 125, 150, 175, 200, 225, 250, 275 or more of the Table 3 genes provides a much greater PML detection sensitivity than chance alone. Preferably one would analyze the airway epithelial cells using more than about 20 of these genes, for example about 20-280 and any combination between, for example, 21, 22, 23, 24, 25, 26, 27, 28, 29, 30, and so on. In some instances, the present inventors have determined that one can enhance the sensitivity or diagnostic accuracy of the methods and assays disclosed herein by adding additional genes to any of these specific groups. For example, in certain aspects, the accuracy of such methods may approach about 70%, about 75%, about 80%, about 82.5%, about 85%, about 87.5%, about 88%, about 90%, about 92.5%, about 95%, about 97.5%, about 98%, about 99% or more by evaluating the differential expression of more genes from the set (e.g., the set of genes set forth in Table 3).

In some embodiments, the presence of PMLs or their progression/regression is made by comparing the expression of the genes or groups of genes set forth in, for example Table 3, by the subject's airway epithelial cells to a control subject or a control group (e.g., a positive control with confirmed PMLs or a confirmed diagnosis of lung cancer). In certain embodiments, an appropriate control is an expression level (or range of expression levels) of a particular gene that is indicative of the known presence of PMLs or a known lung cancer status. An appropriate reference can be determined experimentally by a practitioner of the methods disclosed herein or may be a pre-existing expression value or range of values. When an appropriate control is indicative of lung cancer, a lack of a detectable difference (e.g., lack of a statistically significant difference) between an expression level determined from a subject in need of characterization or diagnosis of lung cancer and the appropriate control may be indicative of lung cancer in the subject. When an appropriate control is indicative of the presence of PMLs or lung cancer, a difference between an expression level determined from a subject in need of characterization or determination of PMLs or diagnosis of lung cancer and the appropriate reference may be indicative of the subject being free of PMLs or lung cancer.

Alternatively, an appropriate control may be an expression level (or range of expression levels) of one or more genes that is indicative of a subject being free of PMLs or lung cancer. For example, an appropriate control may be representative of the expression level of a particular set of genes in a reference (control) biological sample obtained from a subject who is known to be free of PMLs or lung cancer. When an appropriate control is indicative of a subject being free of PMLs or lung cancer, a difference between an expression level determined from a subject in need of detection of PMLs or the diagnosis of lung cancer and the appropriate reference may be indicative of the presence of PMLs and/or lung cancer in the subject. Alternatively, when an appropriate reference is indicative of the subject being free of PMLs or lung cancer, a lack of a detectable difference (e.g., lack of a statistically significant difference) between an expression level determined from a subject in need of detection of PMLs or diagnosis of lung cancer and the appropriate reference level may be indicative of the subject being free of PMLs and/or lung cancer.

The control groups can be or comprise one or more subjects with a confirmed presence of PMLs, positive lung cancer diagnosis, a confirmed absence of PMLs or a negative lung cancer diagnosis. Preferably, the genes or their expression products in the airway epithelial cell sample of the subject are compared relative to a similar group, except that the members of the control groups may not have PMLs and/or lung cancer. For example, such a comparison may be performed in the airway epithelial cell sample from a smoker relative to a control group of smokers who do not have PMLs or lung cancer. The transcripts or expression products are then compared against the control to determine whether increased expression or decreased expression can be observed, which depends upon the particular gene or groups of genes being analyzed, as set forth, for example, in Table 3. In certain embodiments, at least 50% of the gene or groups of genes subjected to expression analysis must provide the described pattern. Greater reliability is obtained as the percent approaches 100%. Thus, in one embodiment, at least about 55%, 60%, 65%, 70%, 75%, 80%, 85%, 90%, 95%, 98%, 99% of the one or more genes subjected to expression analysis demonstrate an altered expression pattern that is indicative of the presence or absence of PMLs or lung cancer, as set forth in, for example, Table 3. Similarly, in one embodiment, at least about 55%, 60%, 65%, 70%, 75%, 80%, 85%, 90%, 95%, 98%, 99% of the one or more genes involved in a pathways set forth in Dataset 2 are subjected to expression analysis and demonstrate an altered expression pattern that is indicative of the subject's cancer status.

Any combination of the genes and/or transcripts of Table 3 can be used in connection with the assays and methods disclosed herein. In one embodiment, any combination of at least 5-10, 10-20, 20-30, 30-40, 40-50, 50-60, 60-70, 70-80, 80, 80-90, 90-100, 100-120, 120-140, 140-150, 150-160, 160-170, 170-180, 180-190, 190-200, 200-210, 210-220, 220-230, 230-240, 240-250, 250-260, 260-270 or 270-280 genes selected from the group consisting of genes or transcripts as shown in the Table 3.

The analysis of the gene expression of one or more genes may be performed using any gene expression methods known to one skilled in the art. Such methods include, but are not limited to expression analysis using nucleic acid chips (e.g. Affymetrix chips) and quantitative RT-PCR based methods using, for example real-time detection of the transcripts. Analysis of transcript levels according to the present invention can be made using total or messenger RNA or proteins encoded by the genes identified in the diagnostic gene groups of the present invention as a starting material. In certain aspects, analysis of transcript levels according to the present invention can be made using micronRNA. In the preferred embodiment the analysis is an immunohistochemical analysis with an antibody directed against proteins comprising at least about 10-20, 20-30, preferably at least 36, at least 36-50, 50, about 50-60, 60-70, 70-80, 80-90, 96, 100-180, 180-200, 200-250 or 250-280 of the proteins encoded by the genes and/or transcripts as shown in Table 3.

The methods of analyzing expression and/or determining an expression profile of the one or more genes include, for example, Northern-blot hybridization, ribonuclease protection assay, and reverse transcriptase polymerase chain reaction (RT-PCR) based methods. In certain aspects, the different RT-PCR based techniques are a suitable quantification method for diagnostic purposes of the present invention, because they are very sensitive and thus require only a small sample size which is desirable for a diagnostic test. A number of quantitative RT-PCR based methods have been described and are useful in measuring the amount of transcripts according to the present invention. These methods include RNA quantification using PCR and complementary DNA (cDNA) arrays (Shalon, et al., Genome Research 6(7):639-45, 1996; Bernard, et al., Nucleic Acids Research 24(8): 1435-42, 1996), real competitive PCR using a MALDI-TOF Mass spectrometry based approach (Ding, et al., PNAS, 100: 3059-64, 2003), solid-phase mini-sequencing technique, which is based upon a primer extension reaction (U.S. Pat. No. 6,013,431, Suomalainen, et al., Mol. Biotechnol. June; 15(2): 123-31, 2000), ion-pair high-performance liquid chromatography (Doris, et al., J. Chromatogr. A May 8; 806(1):47-60, 1998), and 5' nuclease assay or real-time RT-PCR (Holland, et al., Proc Natl Acad Sci USA 88: 7276-7280, 1991).

The presently described gene expression profile can also be used to screen for subjects with confirmed PMLs to determine whether such subject are susceptible to or otherwise at risk for developing lung cancer. For example, a current smoker of advanced age (e.g., 70 years old) with PMLs may be at an increased risk for developing lung cancer and may represent an ideal candidate for the assays and methods disclosed herein. Moreover, the early detection of lung cancer in such a subject may improve the subject's overall survival. Accordingly, in certain aspects, the assays and methods disclosed herein are performed or otherwise comprise an analysis of the subject's secondary risk factors for developing cancer. For example, one or more secondary factors selected from the group consisting of advanced age (e.g., age greater than about 40 years, 50 years, 55 years, 60 years, 65 years, 70 years, 75 years, 80 years, 85 years, 90 years or more), smoking status, the presence of a lung nodule greater than 3 cm on CT scan and the time since the subject quit smoking. In certain embodiments, the assays and methods disclosed herein further comprise a step of considering the presence of any such secondary factors to inform the determination of whether the subject has PMLs or whether such PMLs are likely to progress to lung cancer.

As used herein, a "subject" means a human or animal. Usually the animal is a vertebrate such as a primate, rodent, domestic animal or game animal. In certain embodiments, the subject is a mammal (e.g., a primate or a human). The subject may be an infant, a toddler, a child, a young adult, an adult or a geriatric. The subject may be a smoker, a former smoker or a non-smoker. The subject may have a personal or family history of cancer. The subject may have a cancer-free personal or family history. The subject may exhibit one or more symptoms of lung cancer or other lung disorder (e.g., emphysema, COPD). For example, the subject may have a new or persistent cough, worsening of an existing chronic cough, blood in the sputum, persistent bronchitis or repeated respiratory infections, chest pain, unexplained weight loss and/or fatigue, or breathing difficulties such as shortness of breath or wheezing. The subject may have a lesion, which may be observable by computer-aided tomography or chest X-ray. The subject may be an individual who has undergone a bronchoscopy or who has been identified as a candidate for bronchoscopy (e.g., because of the presence of a detectable lesion or suspicious imaging result). The terms, "patient" and "subject" are used interchangeably herein. In some embodiments, the subject is at risk for developing lung cancer. In some embodiments, the subject has PMLs or lung cancer and the assays and methods disclosed herein may be used to monitor the progression of the subject's disease or to monitor the efficacy of one or more treatment regimens.

In some embodiments, the methods and assays disclosed herein are useful for identifying subjects that are candidates for enrollment in a clinical trial to assess the efficacy of one or more chemotherapeutic agents. In certain aspects, the methods and assays disclosed herein are useful for determining a treatment course for a subject. For example, such methods and assays may involve determining the expression levels of one or more genes (e.g., one or more of the genes set forth in Table 3) in a biological sample obtained from the subject, and determining a treatment course for the subject based on the expression profile of such one or more genes. In some embodiments, the treatment course is determined based on a risk-score derived from the expression levels of the one or more genes analyzed. The subject may be identified as a candidate for a particular intervention or treatment based on an expression profile that indicates the subject's likelihood of having PMLs that will progress lung cancer. Similarly, the subject may be identified as a candidate for an invasive lung procedure (e.g., transthoracic needle aspiration, mediastinoscopy, lobectomy, or thoracotomy) based on an expression profile that indicates the subject has a relatively high likelihood of having PMLs or a high likelihood that such PMLs will progress to lung cancer (e.g., greater than 60%, greater than 70%, greater than 80%, greater than 90%). Conversely, the subject may be identified as not being a candidate for interventional therapy or an invasive lung procedure based on an expression profile that indicates the subject has a relatively low likelihood (e.g., less than 50%, less than 40%, less than 30%, less than 20%) of having PMLs or a low likelihood that such PMLs will progress to lung cancer. In some embodiments, a health care provider may elect to monitor the subject using the assays and methods disclosed herein and/or repeat the assays or methods at one or more later points in time, or undertake further diagnostics procedures to rule out PMLs or lung cancer. Also contemplated herein is the inclusion of one or more of the genes and/or transcripts presented in, for example, Table 3 into a composition or a system for detecting lung cancer in a subject. For example, any one or more genes and or gene transcripts from Table 3 may be added as a PML marker or lung cancer marker for a gene expression analysis. In some aspects, the present inventions relate to compositions that may be used to determine the expression profile of one or more genes from a subject's biological sample comprising airway epithelial cells. For example, compositions are provided that consist essentially of nucleic acid probes that specifically hybridize with one or more genes set forth in Table 3. These compositions may also include probes that specifically hybridize with one or more control genes and may further comprise appropriate buffers, salts or detection reagents. In certain embodiments, such probes may be fixed directly or indirectly to a solid support (e.g., a glass, plastic or silicon chip) or a bead (e.g., a magnetic bead).

The compositions described herein may be assembled into diagnostic or research kits to facilitate their use in one or more diagnostic or research applications. In some embodiments, such kits and diagnostic compositions are provided that comprise one or more probes capable of specifically hybridizing to up to 5, up to 10, up to 25, up to 50, up to 100, up to 200, up to 225, up to 250 or up to 280 genes set forth in Table 3 or their expression products (e.g., mRNA or microRNA). In some embodiments, each of the nucleic acid probes specifically hybridizes with one or more genes selected from those genes set forth in Table 3, or with a nucleic acid having a sequence complementary to such genes. A kit may include one or more containers housing one or more of the components provided in this disclosure and instructions for use. Specifically, such kits may include one or more compositions described herein, along with instructions describing the intended application and the proper use and/or disposition of these compositions. Kits may contain the components in appropriate concentrations or quantities for running various experiments.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

Patient Population

Bronchial airway brushings were obtained during autofluorescence bronchoscopy procedures between June 2000 and March 2011 from subjects in the British Columbia Lung Health Study at the British Columbia Cancer Agency (BCCA) (Vancouver, BC) (29) and between December 2009 and March 2013 from subjects in the High-Risk Lung Cancer-Screening Program at Roswell Park Cancer Institute (RPCI) (Buffalo, N.Y.) (detailed cohort information in the Methods section below). Premalignant Lesions were sampled (if present) using endobronchial biopsy, graded by a team of pathologists at BCCA or RPCI, and the worst histology observed was recorded. Bronchial brushes of normal-appearing epithelium from 84 BCCA subjects (1 brush per subject) with and without PMLs were selected to undergo mRNA-Seq while ensuring balanced clinical covariates. Fifty-one bronchial brushes of normal-appearing epithelium from 23 RPCI subjects were also profiled by mRNA-Seq (18 subjects had 2 procedures, and 5 subjects had 3 procedures). The RPCI samples were utilized in biomarker validation to calculate changes in the biomarker score between sequential procedures. Sets of samples were classified as stable/progressive if the worst histological grade at the second time point for a given patient remained the same or worsened, and regressive if the worst histological grade at the second time point improved. The Institutional Review Boards (IRBs) of all participating institutions approved the study and all subjects provided written informed consent.

RNA-Seq Library Preparation, Sequencing and Data Processing

Total RNA was extracted from bronchial brushings using miRNeasy Mini Kit (Qiagen). Sequencing libraries were prepared from total RNA samples using Illumina® TruSeq® RNA Kit v2 and multiplexed in groups of four using Illumina® TruSeq® Paired-End Cluster Kit. Each sample was sequenced on the Illumina® HiSeq® 2500 to generate paired-end 100 nucleotide reads. Demultiplexing and creation of FASTQ files were performed using Illumina CASAVA v1.8.2. For the BCCA samples, reads were aligned to hg19 using TopHat v2.0.4. The insert size mean and standard deviation were determined using the alignments and MISO (32). Reads were realigned using TopHat and the insert size parameters. Alignment and quality metrics were calculated using RSeQC v2.3.3. Gene count estimates were derived using HTSeq-count v0.5.4 (33) and the Ensembl v64 GTF file. Gene filtering was conducted on normalized counts per million (cpm) calculated using R v3.0.0 and edgeR v3.4.2 using a modified version of the mixture model in the SCAN. UPC Bioconductor package (34). A gene was included in downstream analyses if the mixture model classified it as "on" (i.e. "signal") in at least 15% of the samples. For the RPCI samples, gene counts were computed using RSEM (v1.2.1) (30) and Bowtie (v1.0.0) (31) with Ensembl 74 annotation. The data is available from NCBI's Gene Expression Omnibus (GEO) using the accession ID GSE79315.

Data Analysis for the BCCA Samples

Figure 6:
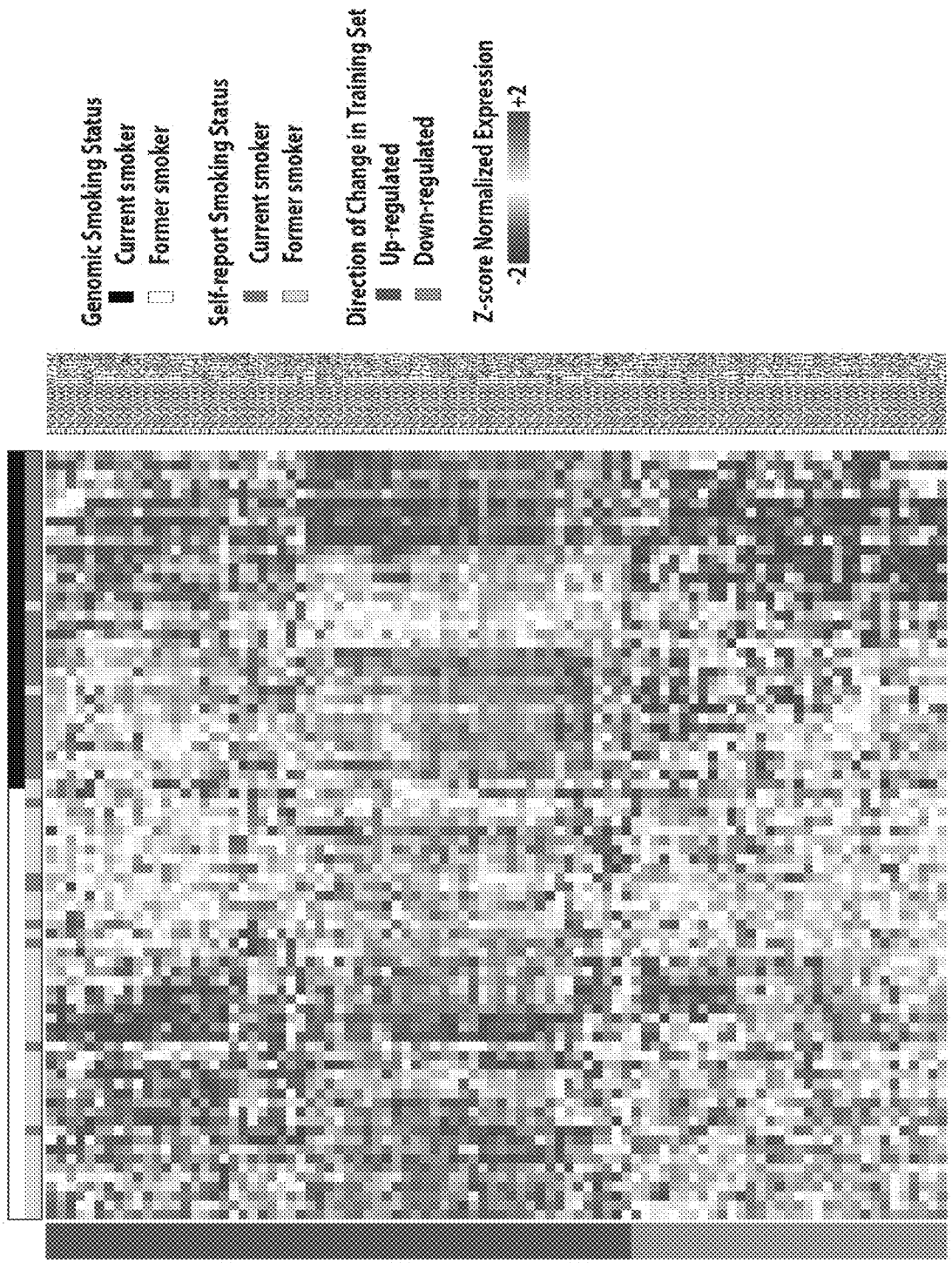
FIG. 6 shows unsupervised hierarchal clustering of genes associated with smoking status. The weighted voting algorithm was trained on z-score normalized microarray data (GSE7895) across 94 genes differentially expressed between current and never smokers and used to predict smoking status in log 2-transformed counts per million (cpm) that were z-score normalized from the 82 mRNA-Seq samples. The heatmap shows the results of unsupervised Ward hierarchal clustering across the 82 mRNA-Seq samples and the 94 genes. The row color label indicates if genes were up-regulated (red) or down-regulated (green) in current smokers compared to never smokers in GSE7895. The lower column color labels indicate the smoking status in the clinical annotation (self-report) with light gray indicating former smokers and dark gray indicating current smokers. The upper column color labels indicate the predicted class of the samples based on the 94 genes with white indicating former smokers and black indicating current smokers. Log 2-cpm mRNA-Seq data was z-score normalized prior to clustering.
Figures 7A, 7B, 7C, 7D, 7E, 7F, 7G, 7H:
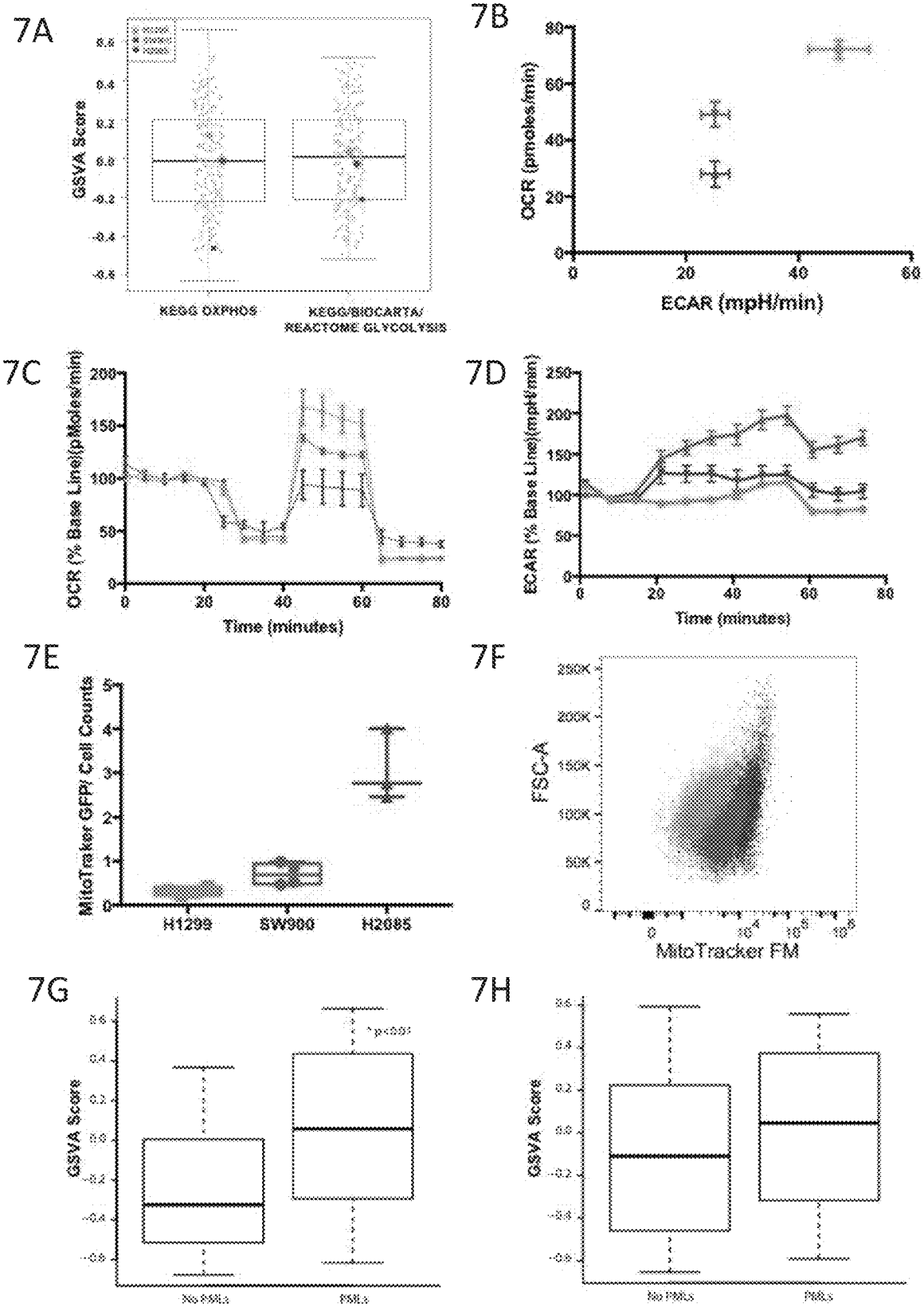
FIGS. 7A-7H show cellular metabolism in cancer cell lines and in the airway field associated with premalignant lesions

Sample and gene filtering yielded 13,870 out of 51,979 genes and 82 samples (n=2 excluded due to quality or sex annotation mismatches) for analysis. Data from Beane et al. (3) was used to predict the smoking status of the 82 samples (Dataset 1, FIG. 6 and Methods) used in all further analysis. Airway brushings were dichotomized into two groups: samples with no evidence of PMLs (samples with no abnormal fluorescing areas or biopsies having normal or hyperplasia histology, n=25); and samples with evidence of PMLs (biopsies having mild, moderate, or severe dysplasia, n=50). Brushes with a worst histology of metaplasia (n=7) were excluded from the dichotomized groups. The limma (35), edgeR (36) and sva packages (37) were used to identify differentially expressed genes associated with presence of PMLs using normalized voom-tranformed (38) data and surrogate variable analysis using the first 7 surrogate variables (Table S1). Gene set enrichment analyses were conducted using ROAST (39) and GSEA (40), and GSVA (41). The Molecular Signatures Database (MSigDb) v4 Entrez ID Gene Sets were converted to Ensembl IDs using BioMart. Additional gene sets were created from CEL files or RNA-Seq counts from The Cancer Cell Line Compendium (CCLE), SCC tumor and adjacent normal tissue from TCGA, GSE19188, GSE18842, and GSE4115 (Supplemental Methods).

Cell Culture

The human bronchial epithelial biopsy cell cultures (Table S2) were obtained from the Colorado Lung SPORE Tissue Bank and cultured in Bronchial Epithelial Growth Media (BEGM). Human non-small cell lung cancer (NSCLC) cell lines were purchased from ATCC and short tandem repeat (STR) profiles were verified at the time of use by the Promega Gene Print® 10 system at the Dana Faber Cancer Institute. H1299, H2085 and SW900 cells were cultured in RPMI supplemented with 10% fetal bovine serum and 1% penicillin/streptomycin, and H2085 cells were cultured in ALC-4 media. All cells were grown in a 37° C. humidified incubator with 5% $CO_2$.

Bioenergetics Studies

Oxygen consumption rates (OCR) and extracellular acidification rates (ECAR) were measured using the XF96 Extracellular Flux Analyzer instrument (Seahorse Bioscience Inc). Briefly, approximately 30,000 cancer cells/well or approximately 40,000 bronchial epithelial biopsy cells/well (higher numbers due to slow growth rate) were seeded on XF96 cell culture plates and grown overnight. Prior to running the assay, media was replaced with Seahorse base media (2 mM (milimole/L) L-glutamine) and placed at 37° C. and 0% $CO_2$ for approximately 30 minutes. The XF Cell Mito Stress Test kit and protocol were utilized to examine mitochondrial function. Measurements were taken every 5 minutes over 80 minutes. To modulate mitochondrial respiration, 5 µM oligomycin, 1 µM FCCP and 5 µM antimycin A were used. Prism software v6 was used to calculate t-statistics for baseline OCR comparisons and a 2-way ANOVA was conducted to compare OCR and ECAR measurements.

Mitochondrial Enumeration Using Flow Cytometry

Using an established protocol (40), cell cultures ($5 \times 10^5$ cells/10 cc dish of bronchial biopsy cultures and cancer cell cultures) were grown overnight and exposed to 120 uM MitoTracker Green FM in media free of FBS for 30 min at 37° C. humidified incubator with 5% $CO_2$. Cells were subsequently collected, washed in PBS and resuspended in 0.5 mL PBS-EDTA and 1 uL of propidium iodide (PI) was added to distinguish live/dead cells. MitoTracker FM and PI were measured using a BD LSRII flow cytometer and BD FACS Diva software (6.2.1). Data was analyzed using FlowJo (10.2), gating out doublets and dead cells, and normalizing mean fluorescence to the number of cell counts.

Immunohistochemistry

Formalin-fixed, paraffin-embedded (FFPE) sections of human PMLs sampled from high-risk subjects undergoing screening for lung cancer were provided by RPCI as part of an IRB-approved study detailed below (Table S3). Dr. Candace Johnson at RPCI provided the FFPE lung sections from the N-nitroso-tris-chloroethylurea (NTCU) mouse model of lung SCC, from mice treated with 25 ml of 40 mmol/L NTCU for 25 weeks in accordance with the Institutional Animal Care and Use Committee approved protocol (42). Antibody dilutions and immunohistochemistry methods were detailed in the Supplemental Methods. Briefly, slides were de-paraffinized and rehydrated. For antigen retrieval, slides were heated in citrate buffer. Slides were subsequently incubated in primary antibody (Translocase of the Outer Mitochondrial Membrane 22 (TOMM22): mouse tissue 1:300 and human 1:1,200 (Abcam), and Cytochrome C Oxidase subunit IV (COX4I1): mouse tissue 1:500 and human 1:5,000 (Abcam)) diluted in 1% Bovine Serum Albumin (BSA). Signal was amplified using an ABC kit (Vector Labs). To reveal endogenous peroxidase activity, slides were incubated in a 3,3'-Diaminobenzidine (DAB) solution. Slides were rinsed, counterstained with hematoxylin, dehydrated in graded alcohol followed by xylene and cover slipped.

Biomarker Development and Validation

A gene expression biomarker discovery pipeline was developed to test thousands of parameter combinations (6,160 predictive models) to identify a biomarker capable of distinguishing between samples from subjects with and without PMLs. Samples were first assigned by batch (sequencing lane) to either a discovery set (n=58) or a validation set (n=17), and the validation set was excluded from biomarker development (FIG. S2 and Supplemental Methods). The biomarker was developed using subsets of the discovery set established by randomly splitting the samples into training (80%, n=46) and test (20%, n=12) sets 500 times. Model performance was assessed using standard metrics for both the training and test sets (Supplemental Methods). The biomarker pipeline was also used to develop biomarkers for sex and smoking status as well as randomized class labels for all phenotypes (serving as positive and negative controls, respectively). A final model (biomarker) was selected (Supplemental Methods) and its ability to distinguish between samples with and without PMLs was tested in a validation set (n=17). In addition, using the bronchial brushings collected longitudinally from subjects at RPCI, we tested whether or not differences in biomarker scores over time were reflective of progression of PMLs (n=28 matched time point pairs) (Supplemental Methods).

Example 2

Results

Subject Population

Figure 1:
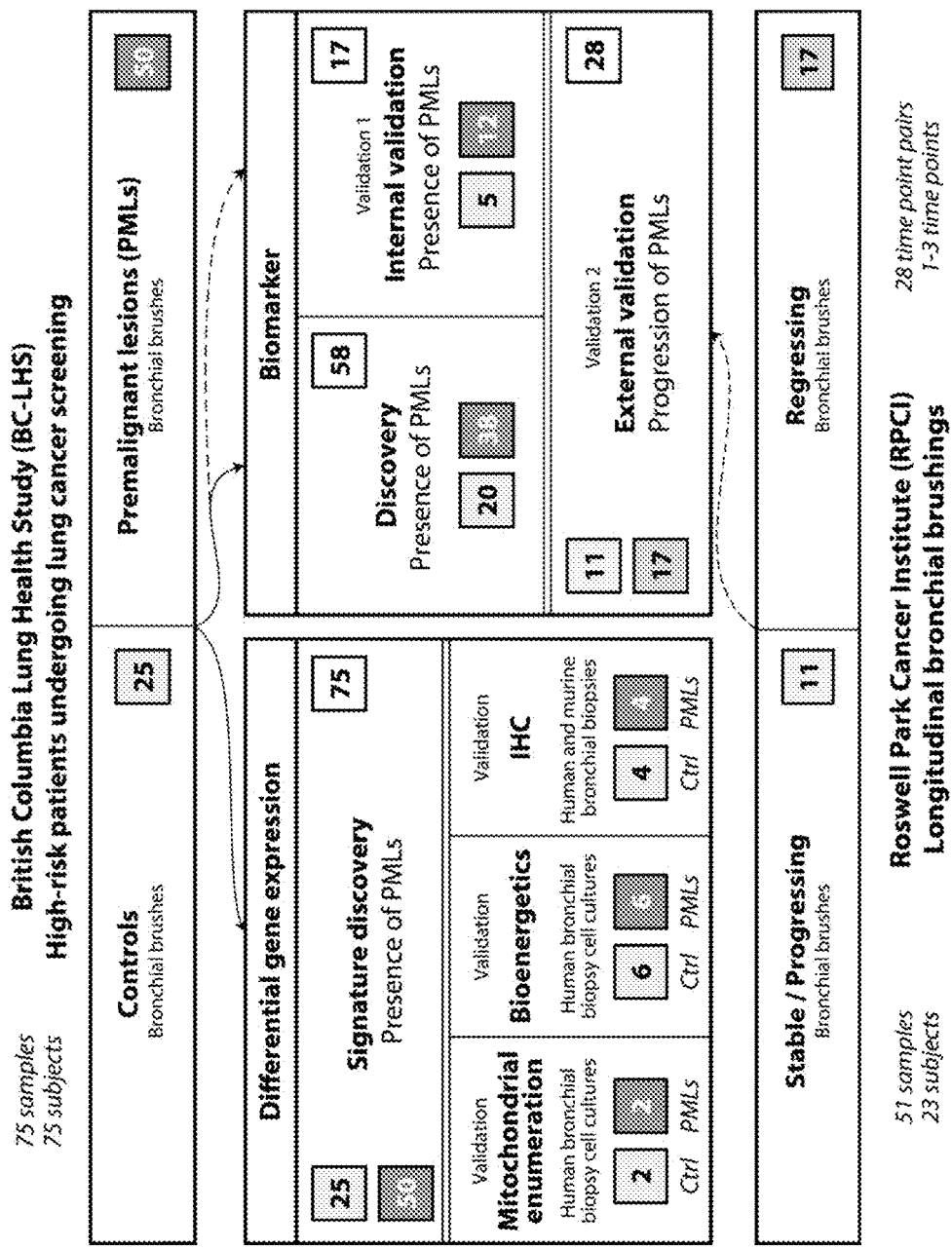
FIG. 1 represents a flow diagram depicting the design of the study used in the Examples. Depicted is the use of bronchial brushings collected from subjects with (red, n=50) and without (gray, n=25) PMLs from the BCCA as part of the BC-LHS for differential gene expression/pathway analysis and for biomarker development. Independent human and mouse bronchial biopsies and biopsy cell cultures were used to validate these findings via mitochondrial enumeration, bioenergetics, and immunohistochemistry (left panel). Biomarker development was conducted by splitting samples from the BC-LHS into a discovery (n=58) and a validation set (Validation 1, n=17) (right panel). The discovery set was used to create the gene expression-based biomarker to detect the presence of PMLs in the airway field of injury. The biomarker was tested on the BC-LHS validation set and an external validation set (bottom) from RPCI (Validation 2, n=28 matched time point pairs, stable/progressing pairs in yellow and regressing pairs in blue).

The study design used 126 bronchial brushings obtained via autofluorescence bronchoscopy at the BCCA and RPCI for differential gene expression and pathway analysis, as well as for biomarker development and validation (FIG. 1). A dataset consisting of samples collected from BCCA subjects with (n=50) and without (n=25) PMLs (n=25) was used to derive a gene expression signature associated with the presence of dysplastic PMLs. Important clinical covariates such as COPD and reported smoking history as well as alignment statistics from the mRNA-Seq data were not significantly different between the two groups (Table 1 and Table 2). For biomarker development, the 75 BCCA samples were split by batch and used in biomarker discovery (n=58) and validation (n=17) (Tables S4 and S5). The change in biomarker score as a predictor of progression of PMLs was then tested in the 51 RPCI samples (Tables S5 and S6).

Figure 2:
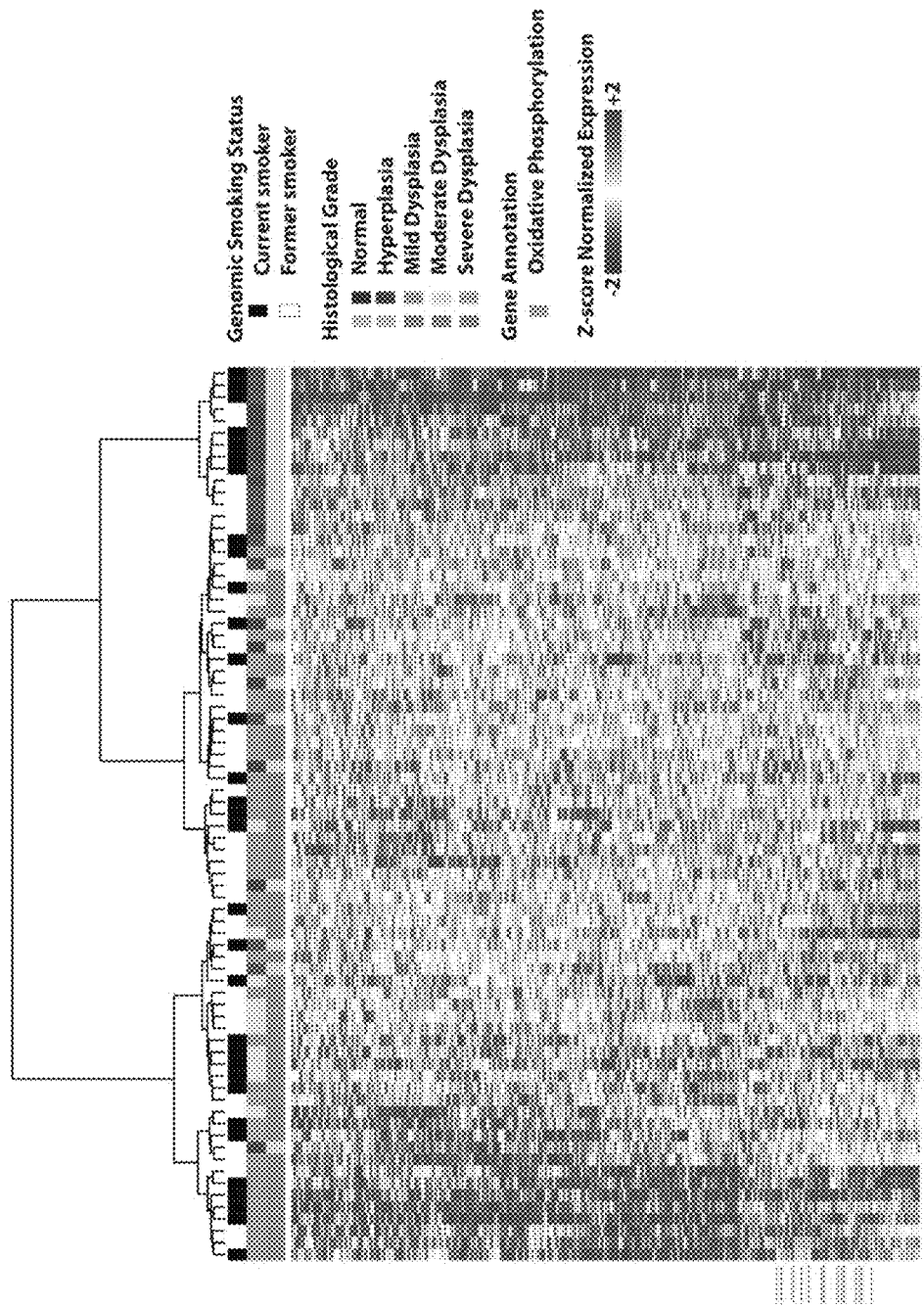
FIG. 2 shows an unsupervised hierarchal clustering of genes associated with the presence of premalignant lesions. Residual gene expression of the 280 genes differentially expressed between subjects with PMLs (red) and without PMLs (gray). Top color bars represent the worst biopsy histological grade observed during bronchoscopy and genomically-derived smoking status of the subjects. The 14 genes in the KEGG oxidative phosphorylation pathway are indicated in cyan. The residual values after adjusting for the 7 surrogate variables were z-score normalized prior to Ward hierarchal clustering.

Transcriptomic Alterations in the Airway Field of Injury Associated with the Presence of PMLs The present inventors identified 280 genes significantly differentially expressed between subjects with and without PMLs (FDR<0.002, FIG. 2). Utilizing the Molecular Signatures Database v4 (MSigDB) canonical pathways, the present inventors identified 170 pathways significantly enriched in genes up- or down-regulated in the presence of PMLs using ROAST (39) (FDR<0.05, Dataset 2). Pathways involved in oxidative phosphorylation (OXPHOS), the electron transport chain (ETC), and mitochondrial protein transport were strongly enriched among genes up-regulated in the airways of subjects with PMLs. Other up-regulated pathways included DNA repair and the HIF1A pathway. Down-regulated pathways included the STAT3 pathway, the JAK/STAT pathway, IL4 signaling, RAC1 regulatory pathway, NCAM1 interactions, collagen formation, and extracellular matrix organization.

OXPHOS is Increased in PML Cell Cultures and Biopsies of Increasing Severity

The ETC and OXPHOS pathways, which involve genes distributed between the complexes I-IV of the ETC and ATP synthase, were highly activated in the airway field in the presence of PMLs. The present inventors wanted to determine if the functional activity of these pathways was similarly altered in PMLs compared to normal tissue. Cellular bioenergetics were conducted by measuring oxygen consumption rate (OCR) as a measure of ETC/OXPHOS and extracellular acidification rate (ECAR) as a measure of glycolysis (anerobic respiration) and MitoTraker Green FM as a measure of mitochondrial content in primary cell cultures derived from bronchial biopsies. Additionally, the present inventors performed immunohistochemistry of select OXPHOS-related genes in mouse and human dysplastic lesions and normal tissue to measure protein levels.

Figures 3A, 3B, 3C, 3D, 3E:
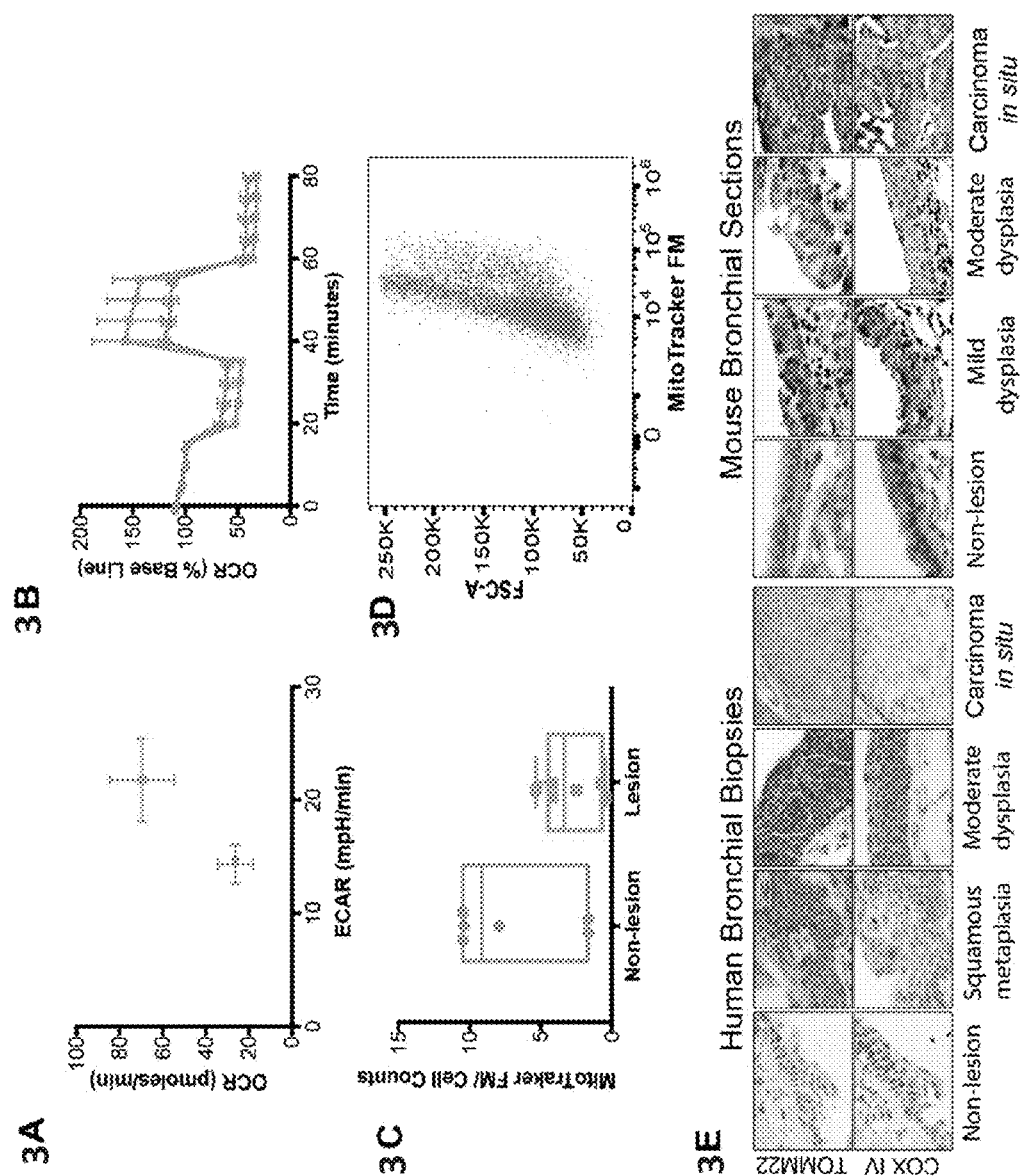
FIGS. 3A-3E illustrate OXPHOS up-regulation in premalignant lesion biopsies.

The present inventors established a significant concordance between ETC/OXPHOS gene expression and cellular bioenergetics in NSCLC cell lines (FIGS. 7A-7F). Next, using primary cell cultures derived from normal to severe dysplastic tissue (Table S2), the present inventors observed that the mean baseline OCR values were 2.5 fold higher in the cultures from PMLs compared to controls (p<0.001, FIG. 3A). Baseline ECAR values were also higher in PML cultures compared to controls, but to a lesser extent (1.5 fold, p<0.001), reflecting predictions based on mRNA-Seq field data (FIGS. 7G-7H). There was a greater reduction in OCR in PMLs immediately following oligomycin treatment (p<0.001) suggesting an increased dependence on OXPHOS for ATP production to meet energetic demands. In addition, the mean spare respiratory capacity following the release of the proton gradient was elevated by approximately 1.5 fold in the PML cultures compared to controls indicating increased ability to respond to energy demands (43). Lastly, treatment with antimycin A resulted in a greater reduction of OCR in PML cultures (p<0.001, FIG. 3B), suggesting that oxygen consumption in the lesions is dependent on increased ETC components in complex III. No significant changes to ECAR were detected in response to mitochondrial perturbations. Furthermore to examine if the increased OXPHOS was a result of increased mitochondrial biogenesis in PML cultures, cells were incubated with MitoTraker FM to stain for mitochondria content and fluorescence enumerated using flow cytometry revealed no significant difference between PML and controls (p=0.15, FIG. 3C-D).

Additionally, the present inventors found elevated protein levels of Translocase of the Outer Mitochondrial Membrane 22 (TOMM22) and Cytochrome C Oxidase subunit IV (COX4I1) in low/moderate grade dysplastic lesions compared to normal tissue (FIG. 3C) using tissues from human bronchial biopsy FFPE sections (Table S3) and whole lung sections from the NTCU mouse model of SCC. The results suggest that PMLs are more ETC- and OXPHOS-dependent and express OXPHOS-related proteins at higher levels compared to normal tissue.

PML-Associated Gene Expression Alterations in the Airway Field are Involved in Lung Squamous Cell Carcinogenesis To further extend the connection between the airway field and PMLs, the present inventors examined the relationship between PML-associated genes in the airway field and other lung cancer-related datasets. The present inventors identified genes differentially expressed between lung tumor tissue (primarily squamous) and normal lung tissue in three different datasets (TCGA, GSE19188, and GSE18842). Genes associated with lung cancer in all datasets were significantly (FDR<0.05) enriched by GSEA, concordantly with gene expression changes associated with the presence of PMLs in the field (FIG. 4A and Dataset 3). Extending beyond the lung tumor, similar enrichment (FDR<0.05) was found using early, stepwise, and late gene expression changes in SCC identified by Ooi et al. (44) (FIG. 4B and Dataset 3) and among genes associated with lung cancer in the airway field of injury (GSE4115, FIG. 4C and Dataset 3). These results support the concept that early events in lung carcinogenesis can be observed throughout the respiratory tract, even in cells that appear cytologically normal.

Development and Validation of a Biomarker for PML Detection and Monitoring

Figure 5A:
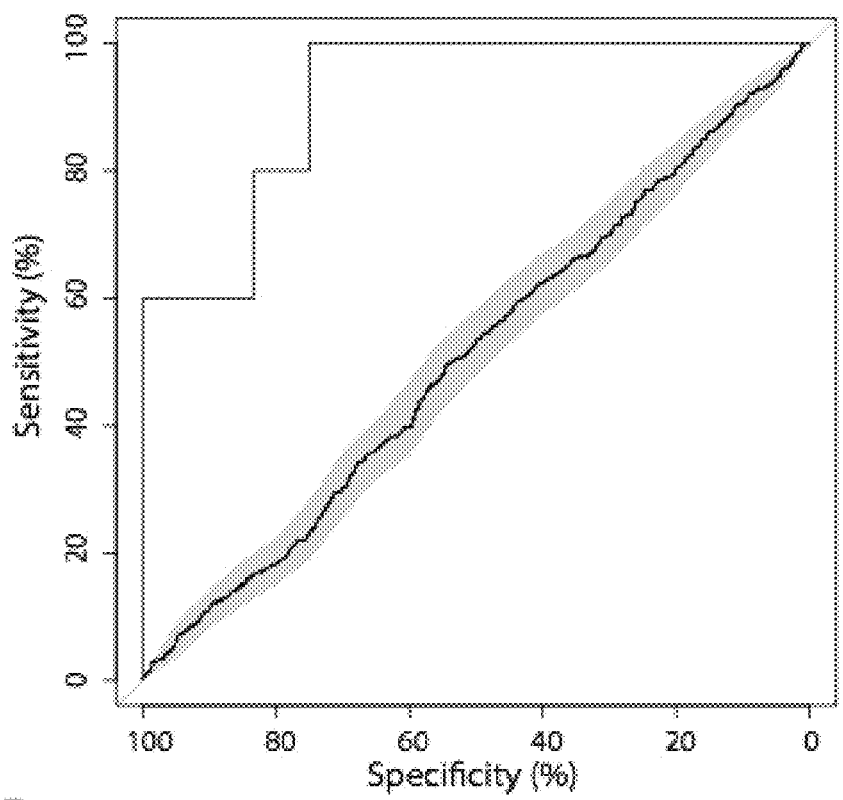
FIGS. 5A-5B show performance of an airway biomarker in detecting the presence and progression of premalignant lesions. The ROC curves demonstrate the biomarker performance.
Figure 5B:
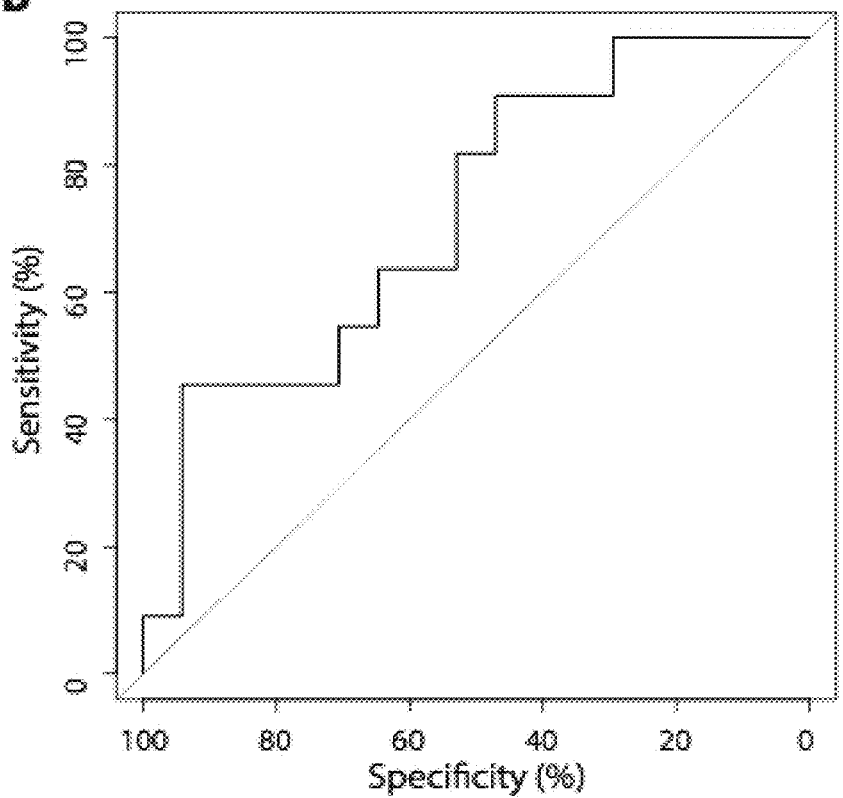

The airway brushings from BCCA subjects with and without PMLs were leveraged to build a biomarker predictive of the presence of PMLs. The biomarker consisted of 200 genes (of which 91 overlapped with the gene signature in FIG. 2) and achieved a ROC-curve AUC of 0.92, sensitivity of 0.75 (9/12 samples with PMLs predicted correctly), and specificity of 1.00 (5/5 samples without PMLs predicted correctly) in independent validation samples (n=17, FIG. 5A). In addition, the biomarker was used to score an independent set of longitudinally collected bronchial brushings from RPCI subjects (FIG. 1). Biomarker scores were calculated for each sample, and the difference in biomarker scores between sequential procedures (n=28 time point pairs, Supplemental Methods) was predictive of whether the worst PML histology observed during the baseline procedure regressed or whether it was stable or progressed with an AUC of 0.75 (FIG. 5B).

Biomarker Predicts Dysplasia Status in Bronchial Biopsies

Abnormal fluorescing areas were biopsied during autofluorescence bronchoscopy of 91 subjects. Biopsies from 47 of the subjects were determined to be premalignant legions (severe, moderate or mild dysplasia) via histology. Biopsies from 44 of the subjects were determined to be normal (normal or hyperplasia) via histology. The ability of the biomarker to predict dysplasia status was assessed. FIG. 9 shows an ROC curve demonstrating the performance of the biomarker in distinguishing between premalignant lesion biopsies (severe=8, moderate=25, and mild dysplasia=14) and biopsies with normal histology (normal=24 and hyperplasia=20). Biomarker achieved AUC of 72% (with a 62%-83% confidence interval), sensitivity of 81% (38 of 47 dysplastic biopsies predicted correctly), and specificity of 66% (29 of 44 normal biopsies predicted correctly).

Discussion

In the foregoing studies, the present inventors identified a PML-associated gene expression signature in cytologically normal bronchial brushings and characterized the biological pathways that are dysregulated in the airway field of injury. The present inventors established that the PML-associated airway field harbors alterations observed in PMLs and in SCC. This evidence motivated the development of a biomarker that reflects the presence of PMLs and their outcome over time. The findings presented herein provide novel insights into the earliest molecular events associated with lung carcinogenesis and have the potential to impact lung cancer prevention by providing novel targets (e.g., OXPHOS) and potential biomarkers for risk stratification and monitoring the efficacy of chemoprevention agents.

The first major finding of the foregoing studies was the identification of a PML-associated field of injury. The most significantly enriched pathways among up-regulated genes in subjects with PMLs were OXPHOS, ETC, and mitochondrial protein transport. These pathways efficiently generate energy in the form of ATP by utilizing the ETC in the mitochondria. During cancer development, energy metabolism alterations are described as an increase in glycolysis and suppression of OXPHOS, known as the Warburg effect (45); however, recent studies demonstrate that OXPHOS is maintained in many tumors and can be important for progression (46). The present inventors wanted to assay for OXPHOS activation in PMLs as it may support PML progression by generating reactive oxygen species (ROS) that can induce oxidative stress, increase DNA damage, and HIF-1a pathway activation (pathways observed in our analysis).

The present inventors observed increases in both the basal OCR and the spare respiratory capacity in the PML biopsies, suggesting that PML-derived cell cultures are more ETC and OXPHOS dependent that the non-PML cultures. The present inventors also demonstrated increases in the presence of mitochondria and ETC activity marked by positive TOMM22 and COX IV staining associated with increasing PML histological grade. Several members of the mitochondrial protein import machinery (46) were significantly up-regulated (FDR<0.05) in airways with PMLs including members of the TOM complex (TOMM22, TOMM7, and TOMM20) and TIM23 complex (TIMM23, TIMM21, and TIMM17A). We observed positive staining of TOMM22 with increasing PML grade, suggesting that increased import of precursor proteins from the endoplasmic reticulum may be required to meet the energy demands of PMLs. Measurements of mitochondrial content indicated no significant differences between the normal and PML-derived cultures, and transcriptional levels of PPARGC1A, associated with mitochondrial biogenesis, were not different between subjects with and without PML indicating that increases in OXPHOS are likely independent of mitochondrial number (47-49). Increases in OXPHOS have been demonstrated to be associated with PML progression in Barret's esophagus and esophageal dysplasia (47), cervical dysplasia (48), and the dysplastic lesions that precede oral SCC (49). Collectively, these data suggest that the OXPHOS pathway may be a target for early intervention. Pre-clinical studies in the NTCU mouse model of lung SCC demonstrate the potential for targeting mitochondrial respiration by using the natural product honokiol to inhibit tumor development (50). Further investigations into the role of cellular energy metabolism in the development and progression of PMLs are needed to fully understand how to best target it for intervention in lung cancer.

Additionally, the present inventors extended the connection between the PML-associated airway field and PMLs beyond the OXPHOS pathway to processes associated with squamous cell lung carcinogenesis. By examining gene sets from multiple external studies representative of lung cancer-related processes occurring in the tumor, adjacent to the tumor, and in the upper airway, significant concordant relationships were found between the PML-associated field and processes associated with SCC tumors. Genes are similarly altered in these varied cancer-associated contexts and thus tissues in the field both adjacent to and far away from the tumor may reflect basic processes and mechanisms of lung carcinogenesis such as DNA damage as hypothesized earlier.

These observations motivated the present inventors to pursue the most translational aspect of this study, a biomarker that can detect PMLs and monitor their progression over time. The 200-gene biomarker, measured in the cytologically normal bronchial airway, achieved high performance detecting the presence of PMLs in a small test set (AUC=0.92). This biomarker may increase the sensitivity of bronchoscopy in detecting the presence of PMLs (which can be difficult to observe under white light), and thus improve identification of high-risk smokers that should be targeted for aggressive lung cancer screening programs. Additionally, the biomarker may offer wider clinical utility in early intervention trials by serving as an intermediate endpoint of efficacy (beyond Ki-67 staining for proliferation, and changes in biopsy histology). Towards this goal, the present inventors demonstrated that the change in biomarker scores over time reflected contemporaneous regressive or progressive/stable disease (AUC=0.75). This result suggests that the airway field of injury in the presence of PMLs is dynamic and that capturing the gene expression longitudinally may allow for further stratification of high-risk subjects. The potential clinical utility of the biomarker is further supported by recent work demonstrating a significant association between the development of incident lung squamous cell carcinoma and the frequency of sites that persist or progress to high-grade dysplasia (24).

Further development and testing in a larger cohort is needed to confirm the biomarker's performance, utility, and ability to predict future PML progression or regression. Additionally, longitudinal and spatial sampling would provide a greater understanding of the dynamic relationship between the normal epithelium and the PMLs as they regress or progress to SCC. Longitudinal studies would allow for more accurate characterization of the time intervals needed to observe gene expression dynamics both in the PMLs and in the airway field of injury. Spatial sampling throughout the respiratory tract, including the more accessible nasal airway that shares the tobacco-related injury with the bronchial airways (51), would allow for evaluation of the impact of distance between the PMLs and the brushing site, the range of PML histologies, and the multiplicity of PMLs that can be present simultaneously in a patient and influence the PML-associated airway field.

Despite these challenges and opportunities for future work, the present inventors have comprehensively profiled gene expression changes in airway epithelial cells in the presence of PMLs that suggest great clinical utility. Moving therapeutics and detection strategies towards an earlier stage in the disease process via molecular characterization of premalignant disease holds great promise (52, 53), and this study represents an important step towards a precision medicine approach to lung cancer prevention.

Materials and Methods
Software Versions Referenced
Data Processing
Illumina CASAVA v1.8.2
TopHat v2.0.4
RSeQC v2.3.3
HTSeq-count v0.5.4
R v3.0.0
edgeR v3.4.2
RSEM v1.2.1
Bowtie v1.0.0
Data Analysis
Limma v3.18.13
edgeR v3.4.2
sva v3.6.0
GSVA v1.10.3
Gene Expression-Based Prediction of Smoking Status Microarray data from Beane et al. (3) Gene Expression Omnibus [GEO] (54) Accession Number GSE7895) was re-analyzed using Robust Multi-array Average (RMA) (54) and the Ensembl CDF file v16.0.0 file website (brainarray.mbni.med.umich.edu/Brainarray/Database/CustomCDF/16.0.0/ensg.asp). The R package (35) was used to identify genes differentially expressed between current (n=52) and never (n=21) smokers, using the linear model presented in the paper additionally correcting for quality covariates (NUSE and RLE). Ninety-four genes (FDR<0.001) were differentially expressed between current and never smokers. The weighted voting algorithm (55) was trained on z-score normalized microarray data (n=73) across the 94 genes and used to predict smoking status in z-scored log 2-transformed counts per million (cpm) from the 82 mRNA-Seq samples.
Processing of Publically Available Datasets Cancer Cell Line Compendium (CCLE). The Entrez ID gene expression file labeled 10/18/2012 and the sample information file were downloaded from CCLE website (broadinstitute.org/ccle/home). After matching the sample annotation to the expression file, we used ComBat (56) to adjust the data for batch effects (n=14 batches across 1019 samples). After batch correction, the lung cell lines (n=186) were selected and GSVA was used to calculate a pathway enrichment score for each lung cell line for the following pathways: KEGG oxidative phosphorylation, KEGG glycolysis gluconeogenesis, BioCarta glycolysis, and Reactome glycolysis. The GSVA scores for the glycolysis pathways were averaged per sample.

The Cancer Genome Atlas (TCGA). RSEM gene-level (Entrez IDs) counts derived from RNA-Seq data were downloaded from the TCGA data portal on Aug. 27, 2013, for lung squamous cell carcinomas and adjacent matched control tissue (n=100 samples from n=50 subjects). After applying the mixture model referenced in the paper, 14,178 out of 20,531 genes were expressed as signal in at least 15% of samples (n=15). Differential gene expression between tumor and adjacent normal tissue was determined using limma and voom-transformed data (38) via a linear model with cancer status as the main effect and a random patient effect modeled using the duplicateCorrelation function. Gene sets containing the top 200 up- and down-regulated differentially expressed genes associated with cancer status were used as input for GSEA.

Microarray Data. CEL files for GSE19188 and GSE18842 were downloaded from GEO and processed using Robust Multi-array Average (RMA) (54) and the Ensembl Gene CDF v16.0.0 file website (brainarray.mbni.med.umich.edu/Brainarray/Database/CustomCDF/16.0.0/ensg.asp).

Samples with a median RLE greater than 0.1 or a median NUSE greater than 1.05 were excluded, yielding n=146 samples for GSE19188 and n=82 samples for GSE18842. For GSE19188, differential gene expression between squamous cell tumors (n=23) and normal lung tissue (n=64) was conducted using limma and a linear model that included RLE and NUSE covariates. For GSE18842, paired normal and tumor tissue from the same subjects (n=37 subjects, n=74 samples) were selected, and differential gene expression was conducted in an analogous manner as described above for TCGA, additionally correcting for RLE and NUSE metrics.

CEL files for GSE4115 were processed using RMA and the CDF file above. The n=164 samples described in Spira et al. (9), were used to determine genes differentially expressed in airway brushings from subjects with and without lung cancer, using limma and a linear model with terms for cancer status, RLE, NUSE, smoking status, and pack-years. Gene sets containing the top 200 up- and down-regulated differentially expressed genes associated with cancer status were used as input for GSEA.
Immunohistochemistry Slides were de-paraffinized, rehydrated, and heated in citrate buffer for antigen retrieval. Slides were treated with 3% $H_2O_2$ (in methanol) to block endogenous peroxidases, incubated in 10% normal goat serum, and primary antibody (TOMM22: mouse tissue 1:300 and human 1:1,200 (Abcam), and COX IV: mouse tissue 1:500 and human 1:5,000 (Abcam)) diluted in 1% BSA. Signal was amplified using an ABC kit (Vector Labs). Slides were next incubated in a 3,3'-Diaminobenzidine (DAB) solution to reveal endogenous peroxidase activity, rinsed, counterstained with hematoxylin, dehydrated in graded alcohol followed by xylene, and cover slipped.
Biomarker Development Upstream gene filtering. In order to provide cross-platform compatibility, the present inventors ran the biomarker discovery and validation pipelines using 11,926 genes commonly present on the RNA-Seq platform (Illumina HiSeq 2500 used with Ensembl v64 GTF) and two microarray platforms (Affymetrix GeneChip Human Gene 1.0 ST Array used with custom ENSG *Homo sapiens* CDF from Brainarray v11 and Affymetrix Human Genome U133A Array used with custom ENSG *Homo sapiens* CDF from Brainarray v16).

Data generation and summarization. Samples (n=75) were run across 4 flow cells (4 batches), and samples run in batches 1, 2, and 3 (n=58) were assigned to a discovery set, while the remaining samples (n=17) were used as an independent validation set and not included in the biomarker development. Alignments and gene level summarization were conducted as described in the paper methods. Alignment and quality metrics were calculated using RSeQC (v2.3.3) (57). Using the gene body measure computed by RSeQC, a ratio between the average read coverage at 80% of the gene length and the average coverage at 20% of the gene length was derived as an additional quality metric (gb-ratio) to assess 3' bias per sample. The metric was highly correlated with a surrogate variable applied in the identification of differentially expressed genes, and was used as a quality control metric in the biomarker pipeline.

Biomarker discovery pipeline. The biomarker discovery pipeline has been outlined generally above. A graphical representation of data flow as well as processing and analysis steps is provided in FIG. 8. Each computational step outlined is detailed in the following sections.

Balancing signature. The present inventors tested gene signatures consisting either of an equal or unequal number of genes up- and down-regulated in subjects with dysplastic lesions.

Input data preprocessing. The present inventors tested 3 input data types. HTSeq-count (v0.5.4) (33) was used to derive gene count estimates (raw counts). In addition, Cufflinks (v2.0.2) (58) was used to derive reads per kilobase per million mapped reads (RPKM) using BAM files containing only properly paired reads. The present inventors also calculated log 2-transformed counts per million (CPM) by applying edgeR (v3.8.6) (36) to raw counts using the "TMM" method (weighted trimmed mean of M-values (59)).

Gene filtering. Signal-based gene filtering was conducted as described in detail above (Methods). In short, a gene was included in downstream analyses if the mixture model classified it as "on" in at least 1%, 5%, 10% or 15% of the samples. For CPM input data type, the present inventors recalculated CPM values using raw counts after filtering out genes.

Feature selection. To identify genes differentially expressed (DE) between samples with and without premalignant lesions (PMLs), the present inventors applied several algorithms to our filtered dataset. The algorithms used were as follows:

(1) edgeR: The present inventors applied the edgeR package (v3.8.6) (46) to raw counts only. After calculating normalization factors (calcNormFactors) and estimating common (estimateGLMCommonDisp) and tagwise (estimateGLMTagwiseDisp) dispersion factors, we identified DE genes associated with the presence of PMLs using a generalized linear model, correcting for sex, COPD status, and smoking status covariates. For balanced signatures, the sign of the log 2-fold change of expression between conditions determined gene directionality. For all models regardless of balancing, gene importance was defined by FDR-adjusted p-value from likelihood ratio tests (glmLRT).

(2) edgeRgb: The present inventors used the edgeR package as described in #1, additionally correcting for gb-ratio (described above in the Data generation and summarization section).

(3) lm: The present inventors applied the limma package (v3.22.7) (35) to CPMs, RPKMs, or voom-transformed raw counts (38). Voom transformation was applied using a linear model, adjusting for sex, COPD status, and smoking status covariates, after calculating normalization factors. The same model was used to identify DE genes associated with the presence of PMLs. For balanced signatures, the sign of the moderated t-statistic obtained via eBayes and topTable determined gene directionality. For all models regardless of balancing, gene importance was defined by the magnitude of the t-statistic.

(4) lmgb: The present inventors used the limma package as described in #3, additionally correcting for gb-ratio (described above in the Data generation and summarization section).

(5) glmnet: The inventors applied the glmnet package (v1.9-8) (60) to CPMs, RPKMs, or voom-transformed raw counts (as in #3) to identify DE genes associated with the presence of PMLs. For balanced signatures, gene directionality was determined by the sign of the t-statistic obtained via limma by running a linear model described in #3. The inventors carried out the following series of steps using all genes for unbalanced signatures and separately using up- and down-regulated genes for balanced signatures: First, RPKMs and CPMs were z-score normalized, while raw counts were voom-transformed. Then, due to the binary character of our response variable (dysplasia status), a logistic regression model was fit using the binomial distribution family and elastic net mixing parameter $\alpha=0.5$ (indicating a tradeoff between ridge and lasso regressions). The standardize option was set to FALSE, causing the coefficients to be returned on the original scale, thus allowing their magnitude to be interpreted as gene importance. Next, a range of regularization parameters $\lambda$ was generated via leave-one-out cross-validation (nfolds=46), and the giving the minimum mean cross-validated error (lambda.min) was chosen to estimate the coefficients. Finally, DE genes were defined as having non-zero coefficients and then sorted by importance based on the coefficients' magnitude.

(6) randomForest: The inventors applied the randomForest package (v4.6-12) (61) to CPMs, RPKMs, and voom-transformed raw counts (as in #3), setting the number of trees (ntree) to 100 and importance to TRUE. For balanced signatures, the sign of the t-statistic as described in #5 determined gene directionality. For all models regardless of balancing, gene importance was determined by the magnitude of the importance variable, defined as the mean decrease in accuracy over both conditions.

(7) DESeq: The inventors applied the DESeq package (v1.18.0) (62) to unmodified raw counts only. DE analysis to find genes associated with the presence of PMLs included data normalization (estimation of the effective library size), variance estimation, and inference for two experimental conditions, as outlined in the DESeq package vignette (bioconductor.org/packages/3.3/bioc/vignettes/DESeq/inst/doc/DESeq.pdf). For balanced signatures, the sign of the log 2-fold change of expression between the two conditions determined gene directionality. For all models regardless of balancing, gene importance was defined by FDR.

(8) SVA: The inventors applied the sva package (v3.12.0) (37) to CPMs, RPKMs, or voom-transformed raw counts. Raw counts were voom-transformed using a linear model including only dysplasia status as the predictor variable. The number of surrogate variables (SVs) not associated with dysplasia status was estimated using the default approach of Buja and Eyuboglu (63) ("be" method). SVs were then identified using the empirical estimation of control probes ("irw" method), and up to 5 were added as covariates in the linear model (limma package). The adjusted model was then used to once again voom-transform raw counts, and subsequently fitted to identify DE genes associated with the presence of PMLs. For balanced signatures, the sign of the moderated t-statistic obtained via topTable determined gene directionality. For all models regardless of balancing, gene importance was defined by the magnitude of the t-statistic.

(9) pAUC (partial AUC) (64): The present inventors applied the rowpAUCs function in the genefilter package (v1.48.1) (65) to CPMs, RPKMs, or voom-transformed raw counts (as in #3). The inventors used 10 class label permutations and a sensitivity cutoff of 0.1 for a specificity range of 0.9-1. For balanced signatures, the sign of the moderated t-statistic obtained via limma's topTable determined gene directionality. For all models regardless of balancing, gene importance was defined by the magnitude of the t-statistic.

Gene signature size. After the feature selection step, the inventors selected the top scoring 10, 20, 40, 60, 80, 100, or 200 genes, making sure that for balanced signatures, half originated from an ordered list of up-regulated genes, and half from an ordered list of down-regulated genes.

Figure 8:
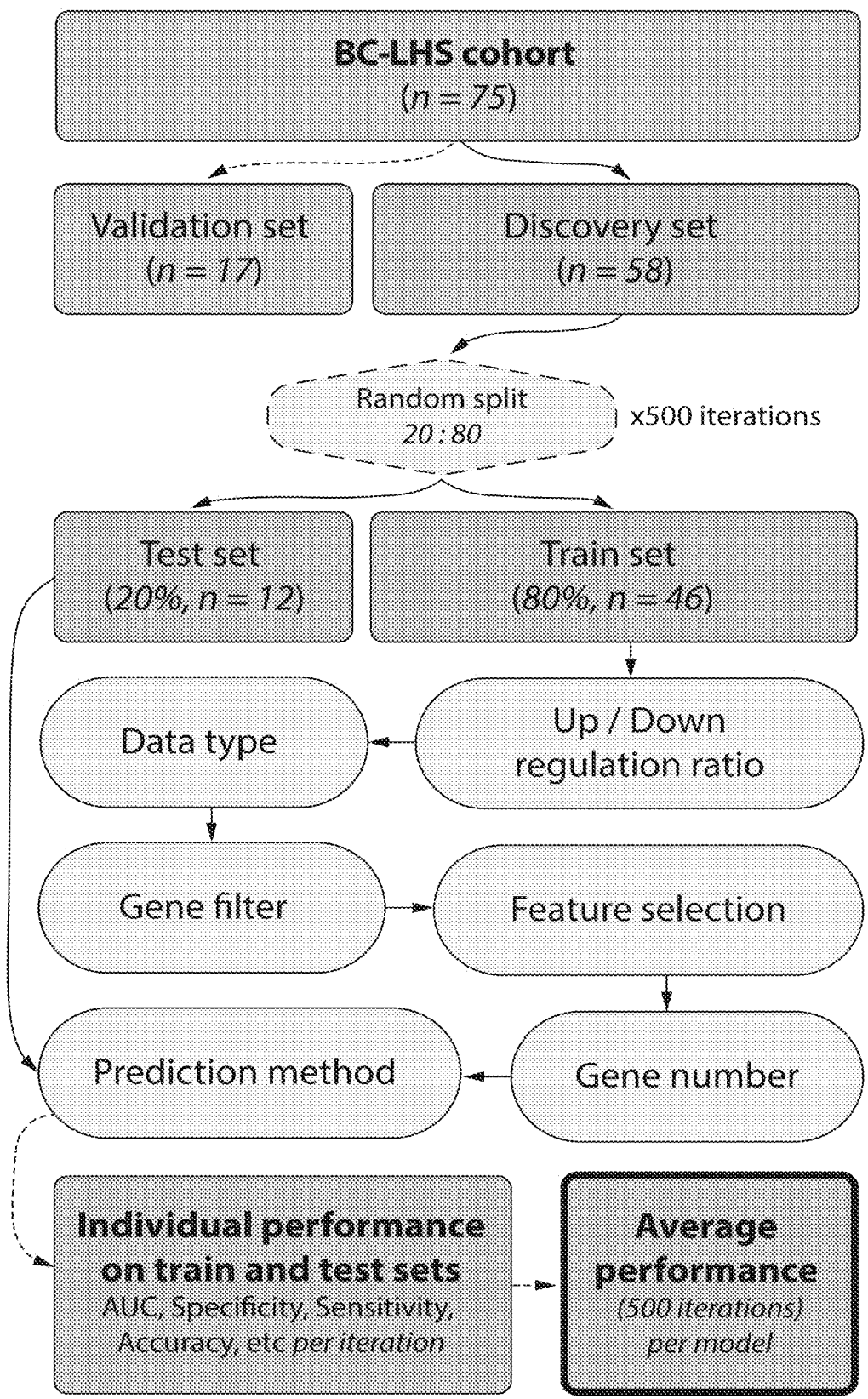
FIG. 8 shows a biomarker discovery flowchart. Samples (n=75) were split into a discovery set (n=58) and a validation set (n=17). The pipeline was run 500 times, and each time the discovery set was randomly split into training (80% of samples, n=46) and test (20% of samples, n=12) sets. The training set samples were used to train the biomarker using all combinations of pipeline parameters, including: 1. Up-/ down-regulation ratio: TRUE or FALSE; 2. Data type: raw counts, RPKM or CPM; 3. Gene filter: genes with signal in at least 1%, 5%, 10%, or 15% of samples; 4. Feature selection: edgeR, edgeR correcting for gb-ratio, limma, limma correcting for gb-ratio, glmnet, random forest, DESeq, SVA, or partial AUC; 5. Gene number: 10, 20, 40, 60, 80, 100, or 200 genes (see Biomarker size); and 6. Prediction method: weighted voting, random forest, SVM, naïve bayes, or glmnet.

Prediction method. For each set of genes, multiple prediction methods were applied to predict dysplasia status (presence of PMLs) in a training set of 46 samples and a test set of 12 samples. These training and test set samples differed in each iteration, which resulted from randomly splitting the 58 discovery set samples (FIG. 8). The following prediction methods were used:

1. glmnet: The inventors used glmnet (v1.9-8) (60) to first estimate a range of penalty parameters λ in 10-fold cross validation using the binomial distribution family parameter and α=0 to ensure all feature-selected genes were included in predictions. Dysplasia status was then predicted as a binary class, using lambda.min penalty.
2. wv (weighted voting) (55): Weighted voting algorithm was used to predict dysplasia status.
3. svm (Support Vector Machine) (66): The inventors used the svm function in the e1071 package (v1.6-7) (66) with linear kernel and 5-fold cross validation for class prediction.
4. rf (random forest): The randomForest package (v4.6-12) (61) was used with 1000 trees, requesting a matrix of class probabilities as output.
5. nb (Naïve Bayes): The naiveBayes function was used in the e1071 package (v1.6-7) with default parameters.

Each of the prediction algorithms generated a vector of predicted scores and a vector of predicted labels for all samples in the training and test sets.

Performance metrics. The present inventors considered 6,160 statistically and computationally viable combinations of the above parameters. The predicted class labels calculated for each model (i.e., a combination of parameters), coupled with true class labels were then used to calculate performance metrics for the biomarker as follows:

| | |
|---|---|
| Accuracy | $\frac{TP + TN}{TP + TN + FP + FN}$ |
| Sensitivity | $\frac{TP}{TP + FN}$ |
| Specificity | $\frac{TN}{FP + TN}$ |
| Positive Predictive Value | $\frac{TP}{TP + FP}$ |
| Negative Predictive Value | $\frac{TN}{TN + FN}$ |
| Matthew's Correlation Coefficient (MCC) | $\frac{(TP \times TN) - (FP \times FN)}{\sqrt{(TP + FP)(TP + FN)(TN + FP)(TN + FN)}}$ |
| AUC for ROC(Receiver Operating Characteristic) | |
| MAQCII metric | $0.5 \times AUC + 0.25 \times (MCC + 1)$, | where $TP$ = true positives;

$FP$ = false positives;

$TN$ = true negatives;

$FN$ = false negatives;

$MCC$ = Matthews's Correlation Coefficient; and $AUC$ = Area under the Curve.

For each model, we calculated these metrics for each of the 500 iterations (different training and test sets assembled from the discovery set samples) and then averaged over all iterations. In addition to the standard performance metrics, we calculated model overfitting and gene selection consistency. The overfitting metric was calculated as the difference between the train set AUC and the test set AUC. Specifically, a model performing well on the training set but poorly on the test set would achieve a high overfitting score. For each model, the gene selection consistency metric was calculated as the average ("normalized" to biomarker size in a given model) percentage of genes passing the gene filter, that were selected into the final gene committee in all 500 iterations:

$$\text{consistency} = 1 - \frac{\text{\# unique genes in all iterations} - \text{biomarker size}}{(\text{biomarker size} \times \text{\# iterations}) - \text{biomarker size}}$$

For example, a model requiring a 10-gene biomarker would have the highest consistency (1) if it selected the same 10 genes in all 500 iterations (10 unique genes selected altogether). The same model would have the lowest consistency (0) if it selected a different set of 10 genes in all iterations (10 genes×500 iterations=5000 unique genes altogether).

Selection of best model. In selecting the best model from among the 6,160 the inventors tested and considered the degree of model overfitting, model gene selection consistency and test set AUC. First, top 10% (n=616) least overfitting models were identified. Simultaneously, the inventors identified top 10% (n=616) most consistent models. Finally, the model with the highest test set AUC among models fulfilling both criteria (n=121) was chosen as the final model.

Selection of final gene signature. The biomarker genes selected may differ between iterations due to changes in the training set. Therefore, to generate a final gene signature, the inventors trained the biomarker using all 58 discovery set samples and best model parameters.

Positive and negative controls. The biomarker discovery pipeline was also used to develop control biomarkers. As positive controls, the inventors used smoking status and sex phenotypes to identify biomarkers that could successfully distinguish former from current smokers (AUC=0.99), and females from males (AUC=0.96). As negative controls, the inventors used randomly shuffled labels for dysplasia status (AUC=0.48), smoking status (AUC=0.52), and sex (AUC=0.51). Label shuffling was conducted preserving the association between gene expression profiles and remaining phenotypes; i.e., in the case of shuffled dysplasia status, only dysplasia status was shuffled while other phenotypes and the corresponding gene expression profile remained unchanged and linked to the same sample ID.

Validations. The performance of the final biomarker was tested using the biomarker discovery pipeline in validation mode. In this mode, the pipeline takes in the entire discovery set (n=58) as the training set, and an external validation set as the test set. The test set is first corrected for gb-ratio (RNA-Seq quality metric) using limma, and the residual data is used as input. Both training and test sets are then z-score normalized. The pipeline was run using only the final model to generate prediction labels and prediction scores for the test set samples. Finally, pROC package (v1.8) (67) was used to visualize and quantify biomarker performance by plotting a ROC curve using prediction scores as the response and the dichotomous phenotype as the predictor, and extracting the AUC value from the resulting ROC object.

Detecting PML Presence in Validation Set Samples

In order to validate the biomarker's ability to detect the presence of PMLs, the performance of the biomarker was tested in smokers with and without PMLs (n=17 samples) left out of the biomarker discovery process. To assess the robustness of the results, we randomly permuted dysplasia status labels 100 times, obtaining biomarker scores for all 17 samples in each of the iterations. The present inventors then concatenated the 100 newly generated biomarker score sets for randomized labels, creating a predictor vector consisting of 1700 scores. Similarly, the inventors concatenated 100 identical copies of biomarker score sets for true labels, creating a response vector of the same length. This allowed the inventors to visualize the performance of the biomarker on true and randomized labels in a single ROC curve (FIG. 5).

Predicting PML Progression in Longitudinally-Collected Samples

In order to validate the biomarker's ability to predict sample progression/regression, the present inventors first used the biomarker to score the longitudinally collected RPCI samples (n=51). Next, calculated the difference in scores between two consecutive time points were calculated for each patient (later time point biomarker score−earlier time point biomarker score). For example, a subject with 3 samples from 3 different time points would have 3 scores, and thus two score differences could be calculated; a subject with 2 samples from 2 time points would have 2 scores, and thus 1 score difference.

Each pair of samples was assigned a "progressing/stable" or "regressing" phenotype. A "progressing/stable" phenotype indicated that the worst histological grade of PMLs sampled during the baseline procedure increased in severity or remained unchanged at follow-up; while a "regressing" phenotype indicated that the worst histological grade of PMLs sampled at baseline decreased in severity at follow-up.

The ability of the score difference to predict the "progression/regression" phenotype was quantified by plotting a ROC curve, using the vector of score differences as the predictor variable, and the progression/regression phenotype as the response variable.

Implementation of the method. The framework and structure of this pipeline are based on principles outlined for microarray data applications. The pipeline outlined in this paper was substantially modified to accommodate RNA-Seq data as well as RNA-Seq-specific methods.

Subject Inclusion/Exclusion Criteria for Samples from the British Columbia Cancer Agency (BCCA)

The samples with normal/hyperplasia histology are part of the Pan-Canadian Study and included subjects between 50 and 75 years old, current or former smokers who have smoked cigarettes for 20 years or more, and that had an estimated 3-year lung cancer risk of greater than or equal to 2%. Exclusion criteria included medical conditions, such as severe heart disease, that would jeopardize the subject's safety during participation in the study, previously diagnosed lung cancer, ex-smokers of greater than or equal to 15 years, anti-coagulant treatment, and pregnancy. The subjects with airway dysplasia were participants in three different chemoprevention studies for green tea extract (n=27 samples), sulindac (n=4 samples), and myo-inositol (n=13 samples) or from the Pan-Canadian Study described above (n=6). All samples were collected at the BCCA at baseline prior to administration of therapeutic interventions. Inclusion criteria for these chemoprevention trials can be summarized as subjects between 40 and 79 years of age, current or former smokers with at least 30 pack-years, no lung cancer history or stage 0/I curatively treated NSCLC either at least 1 year or 6 months prior to the trial (depending on trial). Exclusion criteria varied by trial but included medical conditions that would jeopardize the subject's safety during participation of the study and pregnancy. See details below:

Green Tea:

Inclusion Criteria

Women or men age 45 to 74 years of age

Current or former smokers who have smoked at least 30 pack-years, e.g. 1 pack per day for 30 years or more (a former smoker is defined as one who has stopped smoking for one or more years)

ECOG performance status 0 or 1

C-Reactive Protein >1.2 mg/L

One or more areas of dysplasia with a surface diameter larger than 1.2 mm on autofluorescence bronchoscopy Willing to take Polyphenon E/placebo twice a day regularly Since it is unknown if Polyphenon E or EGCG will cause fetal harm when administered during pregnancy, women subjects must be postmenopausal (no menstrual periods >1 year or elevated FSH>40 mIU/ml), surgically sterile, or using birth control pill. Women of childbearing age must have normal β-HCG within 14 days to exclude pregnancy.

Normal renal and liver function defined as serum creatinine bilirubin, AST, ALT or alkaline phosphatase levels below the upper limit of normal Agreeing to sign, on initial interview, informed consent forms for screening procedures (sputum cytometry analysis, fluorescence bronchoscopy, and low dose spiral thoracic CT scan). Once eligibility has been determined for the chemoprevention trial participation, agreeing to sign a study-specific treatment informed consent form.

Exclusion Criteria

Consumption of more than 7 cups of tea a week

Use of other natural health products containing green tea compounds

Chronic active hepatitis/liver cirrhosis

Severe heart disease, e.g. unstable angina, chronic congestive heart failure, use of antiarrhythmic agents Ongoing gastric ulcer Have on-going rectal bleeding Have a history of chronic diverticulitis and/or colitis Experiencing symptoms of gastritis or hemorrhoids in which medical treatment is required Experiencing any symptomatic gastrointestinal condition that may predispose the individual to gastrointestinal bleeding Acute bronchitis or pneumonia within one month Carcinoma in-situ or invasive cancer on bronchoscopy or abnormal spiral chest CT suspicious of lung cancer Known reaction to Xylocaine salbutamol, midazolam, and alfentanil Known allergy to green tea and/or corn starch, gelatin, or other nonmedicinal ingredients Any medical condition, such as acute or chronic respiratory failure, or bleeding disorder, that in the opinion of the investigator could jeopardize the subject's safety during participation in the study On anti-coagulant treatment such as warfarin or heparin Breastfeeding Pregnancy Unwilling to have a bronchoscopy Unwilling to have a spiral chest CT Unwilling to sign a consent Sulindac:

Inclusion Criteria

Men and women 40 through 79 years of age

Current or former smokers with a ≥30 pack-year smoking history and (a) no prior lung cancer, (b) stage I NSCLC resected at least one year prior to Registration/Randomization, or (c) stage I Non-Small Cell Lung Cancer (NSCLC) with a >1 year interval since adjuvant chemotherapy conclusion Women of childbearing potential and men must agree to use adequate contraception (hormonal or barrier method of birth control; abstinence) prior to study entry and for the duration of study participation. Should a woman become pregnant or suspect she is pregnant while participating in this study, she should inform her treating physician immediately.

A negative (serum or urine) pregnancy test done ≤7 days prior to

Registration/Randomization, for women of childbearing potential only

Willingness to provide tissue blocks and sputum samples for research purposes

Participants must have normal organ and marrow function as defined below and obtained ≤45 days prior to Registration/Randomization:

Hemoglobin ≥lower limit of institutional normal (LLN)

Leukocytes ≥3,000/μL

Absolute neutrophil count ≥1,500/μL

Platelets ≥100,000/μL

Direct bilirubin ≤1.5× institutional upper limit of normal (ULN)

ALT (SGPT)≤1.5× institutional ULN

Creatinine ≤1.5× institutional ULN or calculated creatinine clearance ≥30 ml/min ≥1 site of histologically-confirmed bronchial dysplasia ECOG performance status ≤1

Negative chest x-ray

Negative electrocardiogram

Exclusion Criteria

Prior history of cancer (within the previous 3-years). Exception: Stage I NSCLC as outlined above, non-melanomatous skin cancer, localized prostate cancer, carcinoma in situ (CIS) of cervix, or superficial bladder cancer with conclusion of treatment >6 months prior to Registration/Randomization.

Prior pneumonectomy

Solid organ transplant recipients

History of GI ulceration, bleeding or perforation

Uncontrolled intercurrent illness including, but not limited to: ongoing or active infection, symptomatic congestive heart failure, unstable angina pectoris, cardiac arrhythmia, recent (≤6 months) history of MI, chronic renal disease, chronic liver disease, difficult to control hypertension or psychiatric illness/social situations that would limit compliance with study requirements.

Recent (≤6 months) participation in another chemoprevention trial

Participant currently receiving any other investigational agents

Any supplemental oxygen use (continuous or intermittent use) or documented

Room Air (RA) SaO2<90%

Pregnant women. Note: because there are no adequate, well-controlled studies in pregnant women and sulindac is absolutely contraindicated in the 3rd trimester.

Breastfeeding women. Note: because there is an unknown but potential risk for adverse events in nursing infants secondary to treatment of the mother with sulindac, women who are breast-feeding will be excluded.

Individuals who are known to be HIV positive. Note: HIV positive individuals are excluded for the following two reasons. First, HIV positive individuals are known to have altered immune function. Since one of the potential mechanisms of action of sulindac is proposed to be enhancement of immune function in preventing lung cancer progression, it is not known how the presence of HIV infection would alter this enhancement of immune function as compared to non-HIV infected individuals. Second, individuals with HIV are also known to be at higher risk for lung cancer then non-HIV infected individuals which would alter the risk/incidence of lung cancer in our study population.

Regular NSAID or corticosteroid use during the 6-month period prior to intervention (may be eligible after washout period of 12 weeks for NSAIDs and 6 weeks for corticosteroids)

Regular aspirin use. Exception: Aspirin can be used if prescribed by a physician for prevention. Maximum of one aspirin (81 mg) per day allowed.

History of allergic reactions or hypersensitivity to sulindac or other NSAIDS, including aspirin-sensitive asthma Women of childbearing potential who are unwilling to employ adequate contraception (hormonal or barrier method of birth control; abstinence) prior to study entry and for the duration of study participation. Note: Effects of sulindac on the developing human fetus at the recommended therapeutic dose are fetal harm early in pregnancy. However, there are known harmful adverse events in the third trimester of pregnancy. Should a woman become pregnant or suspect she is pregnant while participating in this study, she should inform her treating physician immediately.

Current use of methotrexate, corticosteroids, (anti-platelet agents) warfarin, ticlopidine, clopidogrel, aspirin, abciximab, dipyridamole, eptifibatide, tirofiban, lithium, cyclosporine, hydralazine, ACE inhibitors Myo-Inositol:
Inclusion Criteria
  Ability to understand and willingness to sign a written informed consent document
  Age ≥45 to ≤79
  ECOG performance status (PS) 0 or 1
  One or both of the following: Stage 0/1 curatively treated non-small cell lung cancer (NSCLC) with a ≥30 pack-year smoking history (surgery, adjuvant chemotherapy or radiotherapy must be completed ≥6 months prior to screening); OR Current or former smokers with a ≥30 pack-year smoking history without a history of lung cancer. Pack-years is determined by multiplying the number of packs smoked per day by the number of years smoked.
  Women of childbearing capacity who agree to use an acceptable form of birth control for the duration of the study (e.g. condom, oral contraceptives, etc.)
Exclusion Criteria
  Prior history of cancer, with the following exceptions:
  ≥3-year disease free interval (with the exception of stage I NSCLC as described above)
  Non-melanomatous skin cancer
  Localized prostate cancer with conclusion of treatment >6 months prior to screening
  Carcinoma in situ (CIS) of cervix with conclusion of treatment >6 months prior to screening
  Superficial bladder cancer with conclusion of treatment >6 months prior to screening
  Prior pneumonectomy
  Solid organ transplant recipients
  Uncontrolled intercurrent illness including, but not limited to: ongoing or active infection, symptomatic congestive heart failure, unstable angina pectoris, cardiac arrhythmia, severe chronic obstructive pulmonary disease requiring supplemental oxygen, difficult to control hypertension, or psychiatric illness/social situations that would limit compliance with study requirements.
  Schizophrenia
  Bipolar disorder
  Lithium treatment
  Carbamazepine treatment
  Valproate treatment
  Diabetes
  Currently using other natural health products containing inositol
  Anticoagulant use such as Coumadin or heparin. Exception: participant is off those drugs for ≥7 days prior to pre-registration.
  Recent (≤6 months) participation in another chemoprevention trial
  Participant currently receiving any other investigational agents
  Any supplemental oxygen use (continuous or intermittent use) or documented Room Air (RA) SaO$_2$<90%
  Pregnant women. (Excluded because the effects of high doses of myo-inositol on the fetus or newborn are not known.)
  Breastfeeding women. (Excluded because the risk for adverse events in nursing infants secondary to treatment of the mother with high doses of myo-inositol are not known.)
  History of allergic reactions attributed to myo-inositol
  History of allergies to any ingredient in the study product or placebo
Early Detection of Lung Cancer—A Pan-Canadian Study:
Inclusion Criteria
  Women or men age 50 to 75 years
  Current or former smokers who have smoked cigarettes for 20 years or more (a former smoker is defined as one who has stopped smoking for one or more years)
  An estimated 3-year lung cancer risk of ≥2% based on the risk prediction model.
  ECOG performance status 0 or 1
  Capable of providing, informed consent for screening procedures (low dose spiral CT, AFB, spirometry, blood biomarkers)
Exclusion Criteria
  Any medical condition, such as severe heart disease (e.g. unstable angina, chronic congestive heart failure), acute or chronic respiratory failure, bleeding disorder, that in the opinion of the investigator could jeopardize the subject's safety during participation in the study or unlikely to benefit from screening due to shortened life-expectancy from the co-morbidities
  Have been previously diagnosed with lung cancer
  Have had other cancer with the exception of the following cancers which can be included in the study: non-melanomatous skin cancer, localized prostate cancer, carcinoma in situ (CIS) of the cervix, or superficial bladder cancer. Treatment of the exceptions must have ended >6 months before registration into this study.
  Ex-smoker for ≥15 years
  On anti-coagulant treatment such as warfarin or heparin
  Known reaction to Xylocaine, salbutamol, midazolam, and alfentanil
  Pregnancy
  Unwilling to have a spiral chest CT
  Chest CT within 2 years
  Unwilling to sign a consent
Subject Inclusion/Exclusion Criteria for Samples from RPCI
  Subjects met the following high-risk lung screening criteria: 1) Personal cancer history of the lung, bronchus, head/neck, and/or esophagus and no evidence of disease at the time of enrollment, or 2) No personal history of upper aerodigestive cancer, age 50+, and a current smoker or a former smoker with 20+ pack years. In addition, subjects in the second group had to have one or more risk factors including chronic lung disease such as emphysema, chronic bronchitis, or chronic obstructive pulmonary disease, occupationally related asbestos disease, or a family history of lung cancer in a first degree relative.

TABLE 1

Demographic and clinical characteristics stratified by premalignant lesion status.

| Factor | Overall (n = 82) | No Lesions (n = 25) | Lesions (n = 50) | P* |
|---|---|---|---|---|
| Age | 62.9 (7.2) | 64.5 (5.8) | 62.2 (8.0) | 0.16 |
| Male | 54/82 (65.9) | 16/25 (64) | 35/50 (70) | 0.61 |
| Current smoker | 40/82 (48.8) | 11/25 (44) | 25/50 (50) | 0.81 |

TABLE 1-continued

Demographic and clinical characteristics stratified by premalignant lesion status.

| Factor | | Overall (n = 82) | No Lesions (n = 25) | Lesions (n = 50) | P* |
|---|---|---|---|---|---|
| Pack-years | | 47.3 (15.7) | 47.6 (17.9) | 47.2 (15.2) | 0.93 |
| FEV1% Predicted | | 82.5 (18.6) | 84.5 (17.9) | 81.7 (19.2) | 0.54 |
| FEV1/FVC Ratio | | 71.2 (7.9) | 73.4 (7.4) | 69.6 (8.1) | 0.05 |
| COPD (FEV1% < 80 & FEV1/FVC < 70) | | 24/82 (29.3) | 5/25 (20) | 17/50 (34) | 0.28 |
| Histology | Normal | 12/82 (14.6) | 12/25 (48) | | <0.001 |
| | Hyperplasia | 13/82 (15.9) | 13/25 (52) | | |
| | Metaplasia | 7/82 (8.5) | | | |
| | Mild Dysplasia | 35/82 (42.7) | | 35/50 (70) | |
| | Moderate Dysplasia | 12/82 (14.6) | | 12/50 (24) | |
| | Severe Dysplasia | 3/82 (3.7) | | 3/50 (6) | |

Data are means (SD) for continuous variables and proportions with percentages for dichotomous variables. P* values are for the comparison of subjects with and without premalignant lesions. Two sample t-tests were used for continuous variables; Fisher's exact test was used for categorical variables.

TABLE 2

Alignment statistics stratified by premalignant lesion status

| Factor | Overall (n = 82) | No Lesions (n = 25) | Lesions (n = 50) | P* |
|---|---|---|---|---|
| Total Alignments | 90M (17M) | 90M (15M) | 91M (19M) | 0.78 |
| Unique Alignments | 83M (16M) | 83M (14M) | 84M (17M) | 0.76 |
| Properly Paired Alignments | 66M (12M) | 66M (11M) | 67M (14M) | 0.75 |
| Genebody 80/20 Ratio | 1.3 (0.2) | 1.3 (0.1) | 1.3 (0.2) | 0.84 |
| Mean GC Content | 47.8 (3.4) | 47.4 (2.9) | 48.2 (3.7) | 0.34 |

Data are means (SD) for continuous variables and proportions with percentages for dichotomous variables. Reads are expressed in millions denoted by M. P* values are for the comparison of subjects with and without premalignant lesions. Two sample t-tests were used for continuous variables; Fisher's exact test was used for factors.

TABLE 3

280 genes differentially expressed between subjects with PMLs and without PMLs

| Ensembl | entrezgene | hgnc_symbol | gene_biotype | wikigene_description | Direction |
|---|---|---|---|---|---|
| ENSG00000223959 | 172 | AFG3L1P | pseudogene | AFG3 ATPase family gene 3-like 1 (*S. cerevisiae*), pseudogene | Down-regulated in the presence of dyplasia |
| ENSG00000115282 | 64427 | TTC31 | protein_coding | tetratricopeptide repeat domain 31 | Down-regulated in the presence of dyplasia |
| ENSG00000139631 | 51380 | CSAD | protein_coding | cysteine sulfinic acid decarboxylase | Down-regulated in the presence of dyplasia |
| ENSG00000198198 | 23334 | SZT2 | protein_coding | seizure threshold 2 homolog (mouse) | Down-regulated in the presence of dyplasia |
| ENSG00000167524 | 124923 | | protein_coding | uncharacterized serine/threonine-protein kinase SgK494 | Down-regulated in the presence of dyplasia |
| ENSG00000242028 | 25764 | C15orf63 | protein_coding | chromosome 15 open reading frame 63 | Down-regulated in the presence of dyplasia |
| ENSG00000235194 | NA | PPP1R3E | protein_coding | | Down-regulated in the presence of dyplasia |
| ENSG00000179979 | 285464 | CRIPAK | protein_coding | cysteine-rich PAK1 inhibitor | Down-regulated in the presence of dyplasia |
| ENSG00000164970 | 203259 | FAM219A | protein_coding | family with sequence similarity 219, member A | Down-regulated in the presence of dyplasia |
| ENSG00000162231 | 10482 | NXF1 | protein_coding | nuclear RNA export factor 1 | Down-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000010322 | 11188 | NISCH | protein_coding | nischarin | Down-regulated in the presence of dyplasia |
| ENSG00000121310 | 55268 | ECHDC2 | protein_coding | enoyl CoA hydratase domain containing 2 | Down-regulated in the presence of dyplasia |
| ENSG00000167978 | 23524 | SRRM2 | protein_coding | serine/arginine repetitive matrix 2 | Down-regulated in the presence of dyplasia |
| ENSG00000229180 | NA | | lincRNA | | Down-regulated in the presence of dyplasia |
| ENSG00000108799 | 2145 | EZH1 | protein_coding | enhancer of zeste homolog 1 (Drosophila) | Down-regulated in the presence of dyplasia |
| ENSG00000070476 | 79364 | ZXDC | protein_coding | ZXD family zinc finger C | Down-regulated in the presence of dyplasia |
| ENSG00000186088 | 54103 | PION | protein_coding | pigeon homolog (Drosophila) | Down-regulated in the presence of dyplasia |
| ENSG00000132680 | 22889 | KIAA0907 | protein_coding | KIAA0907 | Down-regulated in the presence of dyplasia |
| ENSG00000122965 | 9904 | RBM19 | protein_coding | RNA binding motif protein 19 | Down-regulated in the presence of dyplasia |
| ENSG00000130766 | 83667 | SESN2 | protein_coding | sestrin 2 | Down-regulated in the presence of dyplasia |
| ENSG00000064607 | 10147 | SUGP2 | protein_coding | SURP and G patch domain containing 2 | Down-regulated in the presence of dyplasia |
| ENSG00000184863 | 155435 | RBM33 | protein_coding | RNA binding motif protein 33 | Down-regulated in the presence of dyplasia |
| ENSG00000214021 | 26140 | TTLL3 | protein_coding | tubulin tyrosine ligase-like family, member 3 | Down-regulated in the presence of dyplasia |
| ENSG00000080603 | 10847 | SRCAP | protein_coding | Snf2-related CREBBP activator protein | Down-regulated in the presence of dyplasia |
| ENSG00000072121 | 23503 | ZFYVE26 | protein_coding | zinc finger, FYVE domain containing 26 | Down-regulated in the presence of dyplasia |
| ENSG00000182873 | NA | | antisense | | Down-regulated in the presence of dyplasia |
| ENSG00000104365 | 3551 | IKBKB | protein_coding | inhibitor of kappa light polypeptide gene enhancer in B-cells, kinase beta | Down-regulated in the presence of dyplasia |
| ENSG00000167522 | 29123 | ANKRD11 | protein_coding | ankyrin repeat domain 11 | Down-regulated in the presence of dyplasia |
| ENSG00000213190 | 10962 | MLLT11 | protein_coding | myeloid/lymphoid or mixed-lineage leukemia (trithorax homolog, Drosophila); translocated to, 11 | Down-regulated in the presence of dyplasia |
| ENSG00000135407 | 10677 | AVIL | protein_coding | advillin | Down-regulated in the presence of dyplasia |
| ENSG00000185219 | 353274 | ZNF445 | protein_coding | zinc finger protein 445 | Down-regulated in the presence of dyplasia |
| ENSG00000163486 | 23380 | SRGAP2 | protein_coding | SLIT-ROBO Rho GTPase activating protein 2 | Down-regulated in the presence of dyplasia |
| ENSG00000087266 | 6452 | SH3BP2 | protein_coding | SH3-domain binding protein 2 | Down-regulated in the presence of dyplasia |
| ENSG00000198563 | 692199 | DDX39B | protein_coding | DEAD (Asp-Glu-Ala-Asp) box polypeptide 39B | Down-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000142528 | 25888 | ZNF473 | protein_coding | zinc finger protein 473 | Down-regulated in the presence of dyplasia |
| ENSG00000123064 | 79039 | DDX54 | protein_coding | DEAD (Asp-Glu-Ala-Asp) box polypeptide 54 | Down-regulated in the presence of dyplasia |
| ENSG00000042062 | 140876 | FAM65C | protein_coding | family with sequence similarity 65, member C | Down-regulated in the presence of dyplasia |
| ENSG00000247484 | NA | NA | NA | NA | Down-regulated in the presence of dyplasia |
| ENSG00000100201 | 10521 | DDX17 | protein_coding | DEAD (Asp-Glu-Ala-Asp) box helicase 17 | Down-regulated in the presence of dyplasia |
| ENSG00000125633 | 54520 | CCDC93 | protein_coding | coiled-coil domain containing 93 | Down-regulated in the presence of dyplasia |
| ENSG00000257479 | NA |  | lincRNA |  | Down-regulated in the presence of dyplasia |
| ENSG00000076108 | 11176 | BAZ2A | protein_coding | bromodomain adjacent to zinc finger domain, 2A | Down-regulated in the presence of dyplasia |
| ENSG00000137221 | 93643 | TJAP1 | protein_coding | tight junction associated protein 1 (peripheral) | Down-regulated in the presence of dyplasia |
| ENSG00000215424 | 114044 | MCM3AP-AS1 | lincRNA | MCM3AP antisense RNA 1 (non-protein coding) | Down-regulated in the presence of dyplasia |
| ENSG00000100941 | 5411 | PNN | protein_coding | pinin, desmosome associated protein | Down-regulated in the presence of dyplasia |
| ENSG00000170949 | 90338 | ZNF160 | protein_coding | zinc finger protein 160 | Down-regulated in the presence of dyplasia |
| ENSG00000240053 | 58496 | LY6G5B | protein_coding | lymphocyte antigen 6 complex, locus G5B | Down-regulated in the presence of dyplasia |
| ENSG00000181523 | 6448 | SGSH | protein_coding | N-sulfoglucosamine sulfohydrolase | Down-regulated in the presence of dyplasia |
| ENSG00000131398 | 3748 | KCNC3 | protein_coding | potassium voltage-gated channel, Shaw-related subfamily, member 3 | Down-regulated in the presence of dyplasia |
| ENSG00000129933 | 23383 | MAU2 | protein_coding | MAU2 chromatid cohesion factor homolog (C. elegans) | Down-regulated in the presence of dyplasia |
| ENSG00000161010 | 51149 | C5orf45 | protein_coding | chromosome 5 open reading frame 45 | Down-regulated in the presence of dyplasia |
| ENSG00000110888 | 65981 | CAPRIN2 | protein_coding | caprin family member 2 | Down-regulated in the presence of dyplasia |
| ENSG00000130254 | 9667 | SAFB2 | protein_coding | scaffold attachment factor B2 | Down-regulated in the presence of dyplasia |
| ENSG00000184634 | 9968 | MED12 | protein_coding | mediator complex subunit 12 | Down-regulated in the presence of dyplasia |
| ENSG00000077157 | 4660 | PPP1R12B | protein_coding | protein phosphatase 1, regulatory subunit 12B | Down-regulated in the presence of dyplasia |
| ENSG00000133624 | 79970 | ZNF767 | pseudogene | zinc finger family member 767 | Down-regulated in the presence of dyplasia |
| ENSG00000227372 | 57212 | TP73-AS1 | lincRNA | TP73 antisense RNA 1 (non-protein coding) | Down-regulated in the presence of dyplasia |
| ENSG00000100813 | 22985 | ACIN1 | protein_coding | apoptotic chromatin condensation inducer 1 | Down-regulated in the presence of dyplasia |

TABLE 3-continued

280 genes differentially expressed between subjects with PMLs and without PMLs

| Ensembl | entrezgene | hgnc_symbol | gene_biotype | wikigene_description | Direction |
|---|---|---|---|---|---|
| ENSG00000127511 | 23309 | SIN3B | protein_coding | SIN3 transcription regulator homolog B (yeast) | Down-regulated in the presence of dyplasia |
| ENSG00000155363 | 4343 | MOV10 | protein_coding | Mov10, Moloney leukemia virus 10, homolog (mouse) | Down-regulated in the presence of dyplasia |
| ENSG00000124222 | 8675 | STX16 | protein_coding | syntaxin 16 | Down-regulated in the presence of dyplasia |
| ENSG00000099331 | 4650 | MYO9B | protein_coding | myosin IXB | Down-regulated in the presence of dyplasia |
| ENSG00000169246 | NA | NPIPL3 | protein_coding | | Down-regulated in the presence of dyplasia |
| ENSG00000137343 | 79969 | ATAT1 | protein_coding | alpha tubulin acetyltransferase 1 | Down-regulated in the presence of dyplasia |
| ENSG00000169045 | 3187 | HNRNPH1 | protein_coding | heterogeneous nuclear ribonucleoprotein H1 (H) | Down-regulated in the presence of dyplasia |
| ENSG00000205047 | NA | | protein_coding | | Down-regulated in the presence of dyplasia |
| ENSG00000198853 | 9853 | RUSC2 | protein_coding | RUN and SH3 domain containing 2 | Down-regulated in the presence of dyplasia |
| ENSG00000197375 | 6584 | SLC22A5 | protein_coding | solute carrier family 22 (organic cation/carnitine transporter), member 5 | Down-regulated in the presence of dyplasia |
| ENSG00000182796 | 440104 | TMEM198B | pseudogene | transmembrane protein 198B, pseudogene | Down-regulated in the presence of dyplasia |
| ENSG00000182944 | 2130 | EWSR1 | protein_coding | Ewing sarcoma breakpoint region 1 | Down-regulated in the presence of dyplasia |
| ENSG00000065526 | 23013 | SPEN | protein_coding | spen homolog, transcriptional regulator (*Drosophila*) | Down-regulated in the presence of dyplasia |
| ENSG00000137337 | 9656 | MDC1 | protein_coding | mediator of DNA-damage checkpoint 1 | Down-regulated in the presence of dyplasia |
| ENSG00000186174 | 283149 | BCL9L | protein_coding | B-cell CLL/lymphoma 9-like | Down-regulated in the presence of dyplasia |
| ENSG00000075568 | 23505 | TMEM131 | protein_coding | transmembrane protein 131 | Down-regulated in the presence of dyplasia |
| ENSG00000170322 | 4798 | NFRKB | protein_coding | nuclear factor related to kappaB binding protein | Down-regulated in the presence of dyplasia |
| ENSG00000171456 | 171023 | ASXL1 | protein_coding | additional sex like 1 (*Drosophila*) | Down-regulated in the presence of dyplasia |
| ENSG00000044446 | 5256 | PHKA2 | protein_coding | phosphorylase kinase, alpha 2 (liver) | Down-regulated in the presence of dyplasia |
| ENSG00000166436 | 9866 | TRIM66 | protein_coding | tripartite motif containing 66 | Down-regulated in the presence of dyplasia |
| ENSG00000255847 | NA | | antisense | | Down-regulated in the presence of dyplasia |
| ENSG00000245149 | 100507018 | | lincRNA | uncharacterized LOC100507018 | Down-regulated in the presence of dyplasia |
| ENSG00000253200 | NA | | protein_coding | | Down-regulated in the presence of dyplasia |
| ENSG00000100226 | 9567 | GTPBP1 | protein_coding | GTP binding protein 1 | Down-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000146828 | 56996 | SLC12A9 | protein_coding | solute carrier family 12 (potassium/chloride transporters), member 9 | Down-regulated in the presence of dyplasia |
| ENSG00000215769 | NA | | protein_coding | | Down-regulated in the presence of dyplasia |
| ENSG00000168297 | 54899 | PXK | protein_coding | PX domain containing serine/threonine kinase | Down-regulated in the presence of dyplasia |
| ENSG00000225828 | 100128071 | | protein_coding | uncharacterized LOC100128071 | Down-regulated in the presence of dyplasia |
| ENSG00000115459 | 84173 | ELMOD3 | protein_coding | ELMO/CED-12 domain containing 3 | Down-regulated in the presence of dyplasia |
| ENSG00000224660 | 100505696 | | lincRNA | uncharacterized LOC100505696 | Down-regulated in the presence of dyplasia |
| ENSG00000090905 | 27327 | TNRC6A | protein_coding | trinucleotide repeat containing 6A | Down-regulated in the presence of dyplasia |
| ENSG00000205885 | 283314 | | antisense | uncharacterized LOC283314 | Down-regulated in the presence of dyplasia |
| ENSG00000117616 | 57035 | C1orf63 | protein_coding | chromosome 1 open reading frame 63 | Down-regulated in the presence of dyplasia |
| ENSG00000114841 | 25981 | DNAH1 | protein_coding | dynein, axonemal, heavy chain 1 | Down-regulated in the presence of dyplasia |
| ENSG00000132382 | 10514 | MYBBP1A | protein_coding | MYB binding protein (P160) 1a | Down-regulated in the presence of dyplasia |
| ENSG00000061936 | 6433 | SFSWAP | protein_coding | splicing factor, suppressor of white-apricot homolog (*Drosophila*) | Down-regulated in the presence of dyplasia |
| ENSG00000168763 | 265053 | CNNM | protein_coding | cyclin M3 | the presence of dyplasia |
| ENSG00000214765 | 641977 | SEPT7P2 | pseudogene | septin 7 pseudogene 2 | Down-regulated in the presence of dyplasia |
| ENSG00000119321 | 23307 | FKBP15 | protein_coding | FK506 binding protein 15, 133 kDa | Down-regulated in the presence of dyplasia |
| ENSG00000047056 | 22884 | WDR37 | protein_coding | WD repeat domain 37 | Down-regulated in the presence of dyplasia |
| ENSG00000165699 | 7248 | TSC1 | protein_coding | tuberous sclerosis 1 | Down-regulated in the presence of dyplasia |
| ENSG00000168970 | 100137047 | JMJD7-PLA2G4B | protein_coding | JMJD7-PLA2G4B readthrough | Down-regulated in the presence of dyplasia |
| ENSG00000079277 | 8569 | MKNK1 | protein_coding | MAP kinase interacting serine/threonine kinase 1 | Down-regulated in the presence of dyplasia |
| ENSG00000115568 | 7701 | ZNF142 | protein_coding | zinc finger protein 142 | Down-regulated in the presence of dyplasia |
| ENSG00000167615 | 114823 | LENG8 | protein_coding | leukocyte receptor cluster (LRC) member 8 | Down-regulated in the presence of dyplasia |
| ENSG00000100083 | 26088 | GGA1 | protein_coding | golgi-associated, gamma adaptin ear containing, ARF binding protein 1 | Down-regulated in the presence of dyplasia |
| ENSG00000139436 | 9815 | GIT2 | protein_coding | G protein-coupled receptor kinase interacting ArfGAP 2 | Down-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000168066 | 7536 | SF1 | protein_coding | splicing factor 1 | Down-regulated in the presence of dyplasia |
| ENSG00000099917 | 51586 | MED15 | protein_coding | mediator complex subunit 15 | Down-regulated in the presence of dyplasia |
| ENSG00000091831 | 2099 | ESR1 | protein_coding | estrogen receptor 1 | Down-regulated in the presence of dyplasia |
| ENSG00000234420 | 100129482 | ZNF37BP | pseudogene | zinc finger protein 37B, pseudogene | Down-regulated in the presence of dyplasia |
| ENSG00000178971 | 80169 | CTC1 | protein_coding | CTS telomere maintenance complex component 1 | Down-regulated in the presence of dyplasia |
| ENSG00000114982 | 55683 | KANSL3 | protein_coding | KAT8 regulatory NSL complex subunit 3 | Down-regulated in the presence of dyplasia |
| ENSG00000148840 | 23082 | PPRC1 | protein_coding | peroxisome proliferator-activated receptor gamma, coactivator-related 1 | Down-regulated in the presence of dyplasia |
| ENSG00000112941 | 11044 | PAPD7 | protein_coding | PAP associated domain containing 7 | Down-regulated in the presence of dyplasia |
| ENSG00000143624 | 65123 | INTS3 | protein_coding | integrator complex subunit 3 | Down-regulated in the presence of dyplasia |
| ENSG00000139990 | 8816 | DCAF5 | protein_coding | DDB1 and CUL4 associated factor 5 | Down-regulated in the presence of dyplasia |
| ENSG00000100650 | 6430 | SRSF5 | protein_coding | serine/arginine-rich splicing factor 5 | Down-regulated in the presence of dyplasia |
| ENSG00000133460 | 66035 | SLC2A11 | protein_coding | solute carrier family 2 (facilitated glucose transporter), member 11 | Down-regulated in the presence of dyplasia |
| ENSG00000102125 | 6901 | TAZ | protein_coding | tafazzin | Down-regulated in the presence of dyplasia |
| ENSG00000136828 | 9649 | RALGPS1 | protein_coding | Ral GEF with PH domain and SH3 binding motif 1 | Down-regulated in the presence of dyplasia |
| ENSG00000235027 | NA | | antisense | | Down-regulated in the presence of dyplasia |
| ENSG00000235706 | 400242 | DICER1-AS1 | lincRNA | DICER1 antisense RNA 1 (non-protein coding) | Down-regulated in the presence of dyplasia |
| ENSG00000205890 | 100128770 | | antisense | uncharacterized LOC100128770 | Down-regulated in the presence of dyplasia |
| ENSG00000133943 | 80017 | C14orf159 | protein_coding | chromosome 14 open reading frame 159 | Down-regulated in the presence of dyplasia |
| ENSG00000100068 | 91355 | LRP5L | protein_coding | low density lipoprotein receptor-related protein 5-like | Down-regulated in the presence of dyplasia |
| ENSG00000234616 | NA | JRK | processed_transcript | | Down-regulated in the presence of dyplasia |
| ENSG00000115687 | 23178 | PASK | protein_coding | PAS domain containing serine/threonine kinase | Down-regulated in the presence of dyplasia |
| ENSG00000243335 | 154881 | KCTD7 | protein_coding | RAB guanine nucleotide exchange factor (GEF) 1 | Down-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000131149 | 23199 | KIAA0182 | protein_coding | KIAA0182 | Down-regulated in the presence of dyplasia |
| ENSG00000184677 | 9923 | ZBTB40 | protein_coding | zinc finger and BTB domain containing 40 | Down-regulated in the presence of dyplasia |
| ENSG00000116580 | 54856 | GON4L | protein_coding | gon-4-like (*C. elegans*) | Down-regulated in the presence of dyplasia |
| ENSG00000130684 | 26152 | ZNF337 | protein_coding | zinc finger protein 337 | Down-regulated in the presence of dyplasia |
| ENSG00000143442 | 23126 | POGZ | protein_coding | pogo transposable element with ZNF domain | Down-regulated in the presence of dyplasia |
| ENSG00000249093 | NA | NA | NA | NA | Down-regulated in the presence of dyplasia |
| ENSG00000173064 | 283450 | C12orf51 | protein_coding | chromosome 12 open reading frame 51 | Down-regulated in the presence of dyplasia |
| ENSG00000215039 | 678655 | | lincRNA | uncharacterized LOC678655 | Down-regulated in the presence of dyplasia |
| ENSG00000178038 | 259173 | ALS2CL | protein_coding | ALS2 C-terminal like | Down-regulated in the presence of dyplasia |
| ENSG00000258461 | NA | | processed_transcript | | Down-regulated in the presence of dyplasia |
| ENSG00000146830 | 64599 | GIGYF1 | protein_coding | GRB10 interacting GYF protein 1 | Down-regulated in the presence of dyplasia |
| ENSG00000234290 | NA | | antisense | | Down-regulated in the presence of dyplasia |
| ENSG00000120318 | 64411 | ARAP3 | protein_coding | ArfGAP with RhoGAP domain, ankyrin repeat and PH domain 3 | Down-regulated in the presence of dyplasia |
| ENSG00000162241 | 283130 | SLC25A45 | protein_coding | solute carrier family 25, member 45 | Down-regulated in the presence of dyplasia |
| ENSG00000205268 | 5150 | PDE7A | protein_coding | phosphodiesterase 7A | Down-regulated in the presence of dyplasia |
| ENSG00000160712 | 3570 | IL6R | protein_coding | interleukin 6 receptor | Down-regulated in the presence of dyplasia |
| ENSG00000119906 | 55719 | FAM178A | protein_coding | family with sequence similarity 178, member A | Down-regulated in the presence of dyplasia |
| ENSG00000166762 | 117155 | CATSPER2 | protein_coding | cation channel, sperm associated 2 | Down-regulated in the presence of dyplasia |
| ENSG00000203709 | NA | C1orf132 | protein_coding | | Down-regulated in the presence of dyplasia |
| ENSG00000167202 | 23102 | TBC1D2B | protein_coding | TBC1 domain family, member 2B | Down-regulated in the presence of dyplasia |
| ENSG00000140326 | 146059 | CDAN1 | protein_coding | congenital dyserythropoietic anemia, type I | Down-regulated in the presence of dyplasia |
| ENSG00000238105 | 55592 | | pseudogene | golgin A2 pseudogene 5 | Down-regulated in the presence of dyplasia |
| ENSG00000167395 | 9726 | ZNF646 | protein_coding | zinc finger protein 646 | Down-regulated in the presence of dyplasia |
| ENSG00000109063 | 4621 | MYH3 | protein_coding | myosin, heavy chain 3, skeletal muscle, embryonic | Down-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000196689 | 7442 | TRPV1 | protein_coding | transient receptor potential cation channel, subfamily V, member 1 | Down-regulated in the presence of dyplasia |
| ENSG00000168488 | 11273 | ATXN2L | protein_coding | ataxin 2-like | Down-regulated in the presence of dyplasia |
| ENSG00000230124 | 100527964 | | antisense | uncharacterized LOC100527964 | Down-regulated in the presence of dyplasia |
| ENSG00000184551 | NA | | pseudogene | | Down-regulated in the presence of dyplasia |
| ENSG00000198026 | 63925 | ZNF335 | protein_coding | zinc finger protein 335 | Down-regulated in the presence of dyplasia |
| ENSG00000166887 | 23339 | VPS39 | protein_coding | vacuolar protein sorting 39 homolog (S. cerevisiae) | Down-regulated in the presence of dyplasia |
| ENSG00000006530 | 55750 | AGK | protein_coding | acylglycerol kinase | Down-regulated in the presence of dyplasia |
| ENSG00000128191 | 100302197 | DGCR8 | protein_coding | DiGeorge syndrome critical region gene 8 | Down-regulated in the presence of dyplasia |
| ENSG00000109118 | 57649 | PHF12 | protein_coding | PHD finger protein 12 | Down-regulated in the presence of dyplasia |
| ENSG00000068400 | 56850 | GRIPAP1 | protein_coding | GRIP1 associated protein 1 | Down-regulated in the presence of dyplasia |
| ENSG00000228544 | 100131193 | | antisense | uncharacterized LOC100131193 | Down-regulated in the presence of dyplasia |
| ENSG00000204842 | 6311 | ATXN2 | protein_coding | ataxin 2 | Down-regulated in the presence of dyplasia |
| ENSG00000084774 | 790 | CAD | protein_coding | carbamoyl-phosphate synthetase 2, aspartate transcarbamylase, and dihydroorotase | Down-regulated in the presence of dyplasia |
| ENSG00000184787 | 7327 | UBE2G2 | protein_coding | ubiquitin-conjugating enzyme E2G 2 | Down-regulated in the presence of dyplasia |
| ENSG00000173120 | 22992 | KDM2A | protein_coding | lysine (K)-specific demethylase 2A | Down-regulated in the presence of dyplasia |
| ENSG00000215012 | 79680 | C22orf29 | protein_coding | chromosome 22 open reading frame 29 | Down-regulated in the presence of dyplasia |
| ENSG00000135365 | 51317 | PHF21A | protein_coding | PHD finger protein 21A | Down-regulated in the presence of dyplasia |
| ENSG00000157827 | 114793 | FMNL2 | protein_coding | formin-like 2 | Down-regulated in the presence of dyplasia |
| ENSG00000112659 | 23113 | CUL9 | protein_coding | cullin 9 | Down-regulated in the presence of dyplasia |
| ENSG00000108509 | 23125 | CAMTA2 | protein_coding | calmodulin binding transcription activator 2 | Down-regulated in the presence of dyplasia |
| ENSG00000170919 | 100190939 | TPT1-AS1 | lincRNA | TPT1 antisense RNA 1 (non-protein coding) | Down-regulated in the presence of dyplasia |
| ENSG00000197622 | 56882 | CDC42SE1 | protein_coding | CDC42 small effector 1 | Down-regulated in the presence of dyplasia |
| ENSG00000100888 | 57680 | CHD8 | protein_coding | chromodomain helicase DNA binding protein 8 | Down-regulated in the presence of dyplasia |
| ENSG00000213983 | 8906 | AP1G2 | protein_coding | adaptor-related protein complex 1, gamma 2 subunit | Down-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000130827 | 55558 | PLXNA3 | protein_coding | plexin A3 | Down-regulated in the presence of dyplasia |
| ENSG00000198169 | 90987 | ZNF251 | protein_coding | zinc finger protein 251 | Down-regulated in the presence of dyplasia |
| ENSG00000132424 | 25957 | PNISR | protein_coding | PNN-interacting serine/arginine-rich protein | Down-regulated in the presence of dyplasia |
| ENSG00000120709 | 51307 | FAM53C | protein_coding | family with sequence similarity 53, member C | Down-regulated in the presence of dyplasia |
| ENSG00000131067 | 2686 | GGT7 | protein_coding | gamma-glutamyltransferase 7 | Down-regulated in the presence of dyplasia |
| ENSG00000166888 | 6778 | STAT6 | protein_coding | signal transducer and activator of transcription 6, interleukin-4 induced | Down-regulated in the presence of dyplasia |
| ENSG00000258727 | NA | | antisense | | Down-regulated in the presence of dyplasia |
| ENSG00000141867 | 23476 | BRD4 | protein_coding | bromodomain containing 4 | Down-regulated in the presence of dyplasia |
| ENSG00000005339 | 1387 | CREBBP | protein_coding | CREB binding protein | Down-regulated in the presence of dyplasia |
| ENSG00000165275 | 158234 | RG9MTD3 | protein_coding | RNA (guanine-9-) methyltransferase domain containing 3 | Down-regulated in the presence of dyplasia |
| ENSG00000196535 | 399687 | MYO18A | protein_coding | myosin XVIIIA | Down-regulated in the presence of dyplasia |
| ENSG00000125814 | 63908 | NAPB | protein_coding | N-ethylmaleimide-sensitive factor attachment protein, beta | Down-regulated in the presence of dyplasia |
| ENSG00000092421 | 57556 | SEMA6A | protein_coding | sema domain, transmembrane domain (TM), and cytoplasmic domain, (semaphorin) 6A | Down-regulated in the presence of dyplasia |
| ENSG00000137497 | 4926 | NUMA1 | protein_coding | nuclear mitotic apparatus protein 1 | Down-regulated in the presence of dyplasia |
| ENSG00000100416 | 55687 | TRMU | protein_coding | tRNA 5-methylaminomethyl-2-thiouridylate methyltransferase | Down-regulated in the presence of dyplasia |
| ENSG00000110274 | 22897 | CEP164 | protein_coding | centrosomal protein 164 kDa | Down-regulated in the presence of dyplasia |
| ENSG00000104885 | 84444 | DOT1L | protein_coding | DOT1-like, histone H3 methyltransferase (S. cerevisiae) | Down-regulated in the presence of dyplasia |
| ENSG00000244161 | 100506906 | FLNB-AS1 | antisense | FLNB antisense RNA 1 (non-protein coding) | Down-regulated in the presence of dyplasia |
| ENSG00000218418 | NA | | pseudogene | | Down-regulated in the presence of dyplasia |
| ENSG00000171163 | 55657 | ZNF692 | protein_coding | zinc finger protein 692 | Down-regulated in the presence of dyplasia |
| ENSG00000184313 | 374977 | HEATR8 | protein_coding | HEAT repeat containing 8 | Down-regulated in the presence of dyplasia |
| ENSG00000156858 | 78994 | PRR14 | protein_coding | proline rich 14 | Down-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000247743 | NA | NA | NA | NA | Down-regulated in the presence of dyplasia |
| ENSG00000213015 | 51157 | ZNF580 | protein_coding | zinc finger protein 580 | Down-regulated in the presence of dyplasia |
| ENSG00000142937 | 94163 | RPS8 | protein_coding | ribosomal protein S8 | Up-regulated in the presence of dyplasia |
| ENSG00000129518 | 55837 | EAPP | protein_coding | E2F-associated phosphoprotein | Up-regulated in the presence of dyplasia |
| ENSG00000213326 | NA | RP S7P11 | pseudogene | | Up-regulated in the presence of dyplasia |
| ENSG00000177889 | 7334 | UBE2N | protein_coding | ubiquitin-conjugating enzyme E2N | Up-regulated in the presence of dyplasia |
| ENSG00000185834 | NA | RPL12P4 | pseudogene | | Up-regulated in the presence of dyplasia |
| ENSG00000166171 | 25911 | DPCD | protein_coding | deleted in primary ciliary dyskinesia homolog (mouse) | Up-regulated in the presence of dyplasia |
| ENSG00000235297 | NA | | pseudogene | | Up-regulated in the presence of dyplasia |
| ENSG00000181163 | 4869 | NPM1 | protein_coding | nucleophosmin (nucleolar phosphoprotein B23, numatrin) | Up-regulated in the presence of dyplasia |
| ENSG00000177600 | 619565 | RPLP2 | protein_coding | ribosomal protein, large, P2 | Up-regulated in the presence of dyplasia |
| ENSG00000082515 | 29093 | MRPL22 | protein_coding | mitochondrial ribosomal protein L22 | Up-regulated in the presence of dyplasia |
| ENSG00000185068 | 404672 | GTF2H5 | protein_coding | general transcription factor IIH, polypeptide 5 | Up-regulated in the presence of dyplasia |
| ENSG00000134248 | 10542 | HBXIP | protein_coding | hepatitis B virus x interacting protein | Up-regulated in the presence of dyplasia |
| ENSG00000186198 | 123264 | | protein_coding | organic solute transporter beta | Up-regulated in the presence of dyplasia |
| ENSG00000186132 | 130355 | C2orf76 | protein_coding | chromosome 2 open reading frame 76 | Up-regulated in the presence of dyplasia |
| ENSG00000185641 | NA | | pseudogene | | Up-regulated in the presence of dyplasia |
| ENSG00000168653 | 4725 | NDUFS5 | protein_coding | NADH dehydrogenase (ubiquinone) Fe—S protein 5, 15 kDa (NADH-coenzyme Q reductase) | Up-regulated in the presence of dyplasia |
| ENSG00000100554 | 51382 | ATP6V1D | protein_coding | ATPase, H+ transporting, lysosomal 34 kDa, V1 subunit D | Up-regulated in the presence of dyplasia |
| ENSG00000161016 | 6132 | RPL8 | protein_coding | ribosomal protein L8 | Up-regulated in the presence of dyplasia |
| ENSG00000111775 | 1337 | COX6A1 | protein_coding | cytochrome c oxidase subunit VIa polypeptide 1 | Up-regulated in the presence of dyplasia |
| ENSG00000183978 | 28958 | CCDC56 | protein_coding | coiled-coil domain containing 56 | Up-regulated in the presence of dyplasia |
| ENSG00000236552 | 728658 | RPL13AP5 | pseudogene | ribosomal protein L13a pseudogene 5 | Up-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000236801 | NA | | pseudogene | | Up-regulated in the presence of dyplasia |
| ENSG00000131100 | 529 | ATP6V1E1 | protein_coding | ATPase, H+ transporting, lysosomal 31 kDa, V1 subunit E1 | Up-regulated in the presence of dyplasia |
| ENSG00000235174 | NA | RPL39P3 | pseudogene | | Up-regulated in the presence of dyplasia |
| ENSG00000169740 | 7580 | ZNF32 | protein_coding | zinc finger protein 32 | Up-regulated in the presence of dyplasia |
| ENSG00000129562 | 1603 | DAD1 | protein_coding | defender against cell death 1 | Up-regulated in the presence of dyplasia |
| ENSG00000144713 | 6161 | RPL32 | protein_coding | ribosomal protein L32 | Up-regulated in the presence of dyplasia |
| ENSG00000197756 | 6168 | RPL37A | protein_coding | ribosomal protein L37a | Up-regulated in the presence of dyplasia |
| ENSG00000164751 | 5828 | PEX2 | protein_coding | peroxisomal biogenesis factor 2 | Up-regulated in the presence of dyplasia |
| ENSG00000010278 | 100652804 | CD9 | protein_coding | CD9 molecule | Up-regulated in the presence of dyplasia |
| ENSG00000140988 | 26784 | RPS2 | protein_coding | ribosomal protein S2 | Up-regulated in the presence of dyplasia |
| ENSG00000198618 | NA | PPIAP22 | pseudogene | | Up-regulated in the presence of dyplasia |
| ENSG00000151465 | 8872 | CDC123 | protein_coding | cell division cycle 123 homolog (*S. cerevisiae*) | Up-regulated in the presence of dyplasia |
| ENSG00000143543 | 10899 | JTB | protein_coding | jumping translocation breakpoint | Up-regulated in the presence of dyplasia |
| ENSG00000244398 | NA | | pseudogene | | Up-regulated in the presence of dyplasia |
| ENSG00000232856 | NA | | protein_coding | | Up-regulated in the presence of dyplasia |
| ENSG00000108100 | 219771 | CCNY | protein_coding | cyclin Y | Up-regulated in the presence of dyplasia |
| ENSG00000118939 | 7347 | UCHL3 | protein_coding | ubiquitin carboxyl-terminal esterase L3 (ubiquitin thiolesterase) | Up-regulated in the presence of dyplasia |
| ENSG00000169021 | 7386 | UQCRFS1 | protein_coding | ubiquinol-cytochrome c reductase, Rieske iron-sulfur polypeptide 1 | Up-regulated in the presence of dyplasia |
| ENSG00000172809 | 6169 | RPL38 | protein_coding | ribosomal protein L38 | Up-regulated in the presence of dyplasia |
| ENSG00000137154 | 6194 | RPS6 | protein_coding | ribosomal protein S6 | Up-regulated in the presence of dyplasia |
| ENSG00000164405 | 27089 | UQCRQ | protein_coding | ubiquinol-cytochrome c reductase, complex III subunit VII, 9.5 kDa | Up-regulated in the presence of dyplasia |
| ENSG00000143457 | 55204 | GOLPH3L | protein_coding | golgi phosphoprotein 3-like | Up-regulated in the presence of dyplasia |
| ENSG00000138297 | 100287932 | TIMM23 | protein_coding | translocase of inner mitochondrial membrane 23 homolog (yeast) | Up-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000228474 | 100128731 | OST4 | protein_coding | oligosaccharyltransferase 4 homolog (*S. cerevisiae*) | Up-regulated in the presence of dyplasia |
| ENSG00000112981 | 8382 | NME5 | protein_coding | non-metastatic cells 5, protein expressed in (nucleoside-diphosphate kinase) | Up-regulated in the presence of dyplasia |
| ENSG00000112667 | 10591 | C6orf108 | protein_coding | chromosome 6 open reading frame 108 | Up-regulated in the presence of dyplasia |
| ENSG00000183617 | 116541 | MRPL54 | protein_coding | mitochondrial ribosomal protein L54 | Up-regulated in the presence of dyplasia |
| ENSG00000188873 | NA | RPL10AP2 | pseudogene | | Up-regulated in the presence of dyplasia |
| ENSG00000131143 | 1327 | COX4I1 | protein_coding | cytochrome c oxidase subunit IV isoform 1 | Up-regulated in the presence of dyplasia |
| ENSG00000178741 | 9377 | COX5A | protein_coding | cytochrome c oxidase subunit Va | Up-regulated in the presence of dyplasia |
| ENSG00000232112 | 51372 | CCDC72 | protein_coding | coiled-coil domain containing 72 | Up-regulated in the presence of dyplasia |
| ENSG00000178449 | 84987 | COX14 | protein_coding | COX14 cytochrome c oxidase assembly homolog (*S. cerevisiae*) | Up-regulated in the presence of dyplasia |
| ENSG00000138663 | 51138 | COPS4 | protein_coding | COP9 constitutive photomorphogenic homolog subunit 4 (*Arabidopsis*) | Up-regulated in the presence of dyplasia |
| ENSG00000149547 | 9538 | EI24 | protein_coding | etoposide induced 2.4 mRNA | Up-regulated in the presence of dyplasia |
| ENSG00000173660 | 440567 | UQCRH | protein_coding | ubiquinol-cytochrome c reductase hinge protein | Up-regulated in the presence of dyplasia |
| ENSG00000125356 | 4694 | NDUFA1 | protein_coding | NADH dehydrogenase (ubiquinone) 1 alpha subcomplex, 1, 7.5 kDa | Up-regulated in the presence of dyplasia |
| ENSG00000162244 | 6159 | RPL29 | protein_coding | ribosomal protein L29 | Up-regulated in the presence of dyplasia |
| ENSG00000174444 | 595097 | RPL4 | protein_coding | ribosomal protein L4 | Up-regulated in the presence of dyplasia |
| ENSG00000145247 | 132299 | OCIAD2 | protein_coding | OCIA domain containing 2 | Up-regulated in the presence of dyplasia |
| ENSG00000178980 | 6415 | SEPW1 | protein_coding | selenoprotein W, 1 | Up-regulated in the presence of dyplasia |
| ENSG00000169020 | 521 | ATP5I | protein_coding | ATP synthase, H+ transporting, mitochondrial Fo complex, subunit E | Up-regulated in the presence of dyplasia |
| ENSG00000125743 | 6633 | SNRPD2 | protein_coding | small nuclear ribonucleoprotein D2 polypeptide 16.5 kDa | Up-regulated in the presence of dyplasia |
| ENSG00000101928 | 56180 | MOSPD1 | protein_coding | motile sperm domain containing 1 | Up-regulated in the presence of dyplasia |
| ENSG00000151366 | 100532726 | NDUFC2 | protein_coding | NADH dehydrogenase (ubiquinone) 1, subcomplex unknown, 2, 14.5 kDa | Up-regulated in the presence of dyplasia |

TABLE 3-continued 280 genes differentially expressed between subjects with PMLs and without PMLs

| Ensembl | entrezgene | hgnc_symbol | gene_biotype | wikigene_description | Direction |
|---|---|---|---|---|---|
| ENSG00000171421 | 64979 | MRPL36 | protein_coding | mitochondrial ribosomal protein L36 | Up-regulated in the presence of dyplasia |
| ENSG00000198755 | 4736 | RPL10A | protein_coding | ribosomal protein L10a | Up-regulated in the presence of dyplasia |
| ENSG00000232119 | 28985 | MCTS1 | protein_coding | malignant T cell amplified sequence 1 | Up-regulated in the presence of dyplasia |
| ENSG00000198643 | 131177 | FAM3D | protein_coding | family with sequence similarity 3, member D | Up-regulated in the presence of dyplasia |
| ENSG00000123144 | 79002 | C19orf43 | protein_coding | chromosome 19 open reading frame 43 | Up-regulated in the presence of dyplasia |
| ENSG00000111669 | 7167 | TPI1 | protein_coding | triosephosphate isomerase 1 | Up-regulated in the presence of dyplasia |
| ENSG00000089063 | 29058 | TMEM230 | protein_coding | chromosome 20 open reading frame 30 | Up-regulated in the presence of dyplasia |
| ENSG00000214026 | 6150 | MRPL23 | protein_coding | mitochondrial ribosomal protein L23 | Up-regulated in the presence of dyplasia |
| ENSG00000119421 | 4702 | NDUFA8 | protein_coding | NADH dehydrogenase (ubiquinone) 1 alpha subcomplex, 8, 19 kDa | Up-regulated in the presence of dyplasia |
| ENSG00000135940 | 1329 | COX5B | protein_coding | cytochrome c oxidase subunit Vb | Up-regulated in the presence of dyplasia |
| ENSG00000146066 | 192286 | HIGD2A | protein_coding | HIG1 hypoxia inducible domain family, member 2A | Up-regulated in the presence of dyplasia |
| ENSG00000170892 | 79042 | TSEN34 | protein_coding | tRNA splicing endonuclease 34 homolog (S. cerevisiae) | Up-regulated in the presence of dyplasia |
| ENSG00000166920 | 84419 | C15orf48 | protein_coding | chromosome 15 open reading frame 48 | Up-regulated in the presence of dyplasia |
| ENSG00000140307 | 2958 | GTF2A2 | protein_coding | general transcription factor IIA, 2, 12 kDa | Up-regulated in the presence of dyplasia |
| ENSG00000184831 | 79135 | APOO | protein_coding | apolipoprotein O | Up-regulated in the presence of dyplasia |
| ENSG00000205544 | 254863 | C17orf61 | protein_coding | chromosome 17 open reading frame 61 | Up-regulated in the presence of dyplasia |

SUPPLEMENTAL TABLE 1

ANOVA derived p-values for the association between the surrogate variables and demographic/phenotypic variables

| Variable | SV1 | SV2 | SV3 | SV4 | SV5 | SV6 | SV7 | SV8 | SV9 |
|---|---|---|---|---|---|---|---|---|---|
| Presence of premalignant lesion (2-level) | 0.549 | 0.376 | 0.964 | 0.500 | 0.118 | 0.481 | 0.046 | 0.166 | 0.652 |
| Smoking status | 0.000 | 0.655 | 0.191 | 0.084 | 0.689 | 0.804 | 0.308 | 0.719 | 0.761 |
| Smoking status by Gene Expression | 0.000 | 0.363 | 0.801 | 0.045 | 0.819 | 0.780 | 0.130 | 0.827 | 0.663 |
| Sex | 0.961 | 0.058 | 0.000 | 0.032 | 0.492 | 0.801 | 0.433 | 0.884 | 0.991 |
| COPD status | 0.612 | 0.866 | 0.047 | 0.161 | 0.973 | 0.129 | 0.083 | 0.007 | 0.592 |
| Pack-years | 0.398 | 0.293 | 0.523 | 0.576 | 0.845 | 0.399 | 0.875 | 0.428 | 0.178 |
| Age | 0.300 | 0.153 | 0.562 | 0.845 | 0.166 | 0.618 | 0.037 | 0.050 | 0.528 |
| FEV1 | 0.050 | 0.391 | 0.046 | 0.009 | 0.123 | 0.150 | 0.171 | 0.028 | 0.691 |
| FEV1/FVC ratio | 0.023 | 0.670 | 0.172 | 0.056 | 0.491 | 0.107 | 0.028 | 0.011 | 0.708 |
| Barcode | 0.870 | 0.605 | 0.006 | 0.500 | 0.745 | 0.444 | 0.695 | 0.119 | 0.187 |
| Lane | 0.335 | 0.748 | 0.682 | 0.351 | 0.037 | 0.792 | 0.402 | 0.996 | 0.549 |
| Batch | 0.676 | 0.730 | 0.474 | 0.426 | 0.861 | 0.037 | 0.145 | 0.688 | 0.261 |
| GC content | 0.599 | 0.886 | 0.057 | 0.902 | 0.257 | 0.157 | 0.001 | 0.416 | 0.210 |
| Genebody 80/20 ratio (gb-ratio) | 0.000 | 0.245 | 0.633 | 0.271 | 0.000 | 0.736 | 0.015 | 0.319 | 0.048 |
| Number of Uniquely Aligning Reads | 0.302 | 0.154 | 0.726 | 0.948 | 0.055 | 0.120 | 0.036 | 0.163 | 0.586 |

SUPPLEMENTAL TABLE 1-continued

ANOVA derived p-values for the association between the surrogate variables and demographic/phenotypic variables

| Variable | SV1 | SV2 | SV3 | SV4 | SV5 | SV6 | SV7 | SV8 | SV9 |
|---|---|---|---|---|---|---|---|---|---|
| Number of Reads Aligning to Splice Junctions | 0.545 | 0.605 | 0.498 | 0.442 | 0.000 | 0.383 | 0.170 | 0.745 | 0.942 |
| Z-score (sample mean of z-score normalized data by gene) | 0.514 | 0.371 | 0.238 | 0.595 | 0.024 | 0.031 | 0.005 | 0.353 | 0.021 |
| Relative Expression (sample median of ratios computed for each gene by dividing the expression by the median expression) | 0.814 | 0.615 | 0.996 | 0.740 | 0.918 | 0.887 | 0.214 | 0.274 | 0.111 |

SUPPLEMENTAL TABLE 2

Phenotypic information about the human biopsy cell cultures used in the bioenergetics experiments.

| Histology | Gender | Smoking Status | Bioenergetics | MitoTrackerFM |
|---|---|---|---|---|
| Normal | F | Current | X | |
| Normal | M | Current | X | |
| Normal | F | Former | X | |
| Normal | M | Former | X | |
| Normal | F | Current | X | X |
| Normal | F | Current | X | X |
| Moderate Dysplasia | M | Current | X | |
| Severe Dysplasia | M | Former | X | |
| Severe Dysplasia | M | Current | X | |
| Low grade dysplasia | M | Former | X | |
| Severe Dysplasia | M | Current | X | X |
| Low grade dysplasia | M | Former | X | X |

SUPPLEMENTAL TABLE 3

Phenotypic information about the human biopsies used in the IHC experiments.
(*CS refers to current smoker and FS to former smoker)

| Stain | PtID | Smoking Status | WorstHistology_Description |
|---|---|---|---|
| Tomm-22 | Pt 3 | FS | 0 Normal, Negative, Benign Mucosa |
| Cox-IV | Pt 3 | FS | 0 Normal, Negative, Benign Mucosa |
| Tomm-22 | Pt 4 | FS | 23 Squamous Metaplasia (non-specific), Mature Metaplasia, Squamous Hyperplasia |
| Cox-IV | Pt 4 | FS | 23 Squamous Metaplasia (non-specific), Mature Metaplasia, Squamous Hyperplasia |
| Tomm-22 | Pt 3 | FS | 25 Moderate Dysplasia, Squamous Pre-invasive |
| Cox-IV | Pt 3 | FS | 25 Moderate Dysplasia, Squamous Pre-invasive |
| Tomm-22 | Pt 1 | CS | 27 CIS Squamous Carcinoma In-Situ |
| Cox-IV | Pt 1 | CS | 27 CIS Squamous Carcinoma In-Situ |

SUPPLEMENTAL TABLE 4

Demographic and clinical characteristics of the British Columbia Lung Health Study stratified by premalignant lesions status

| | Discovery Set | | | | Validation Set | | | |
|---|---|---|---|---|---|---|---|---|
| Factor | Overall (n = 58) | No Lesions (n = 20) | Lesions (n = 38) | P* | Overall (n = 17) | No Lesions (n = 5) | Lesions (n = 12) | P* |
| Age | 62.7 (7.1) | 64.1 (5.8) | 61.9 (7.6) | 0.24 | 63.9 (8.6) | 66 (5.8) | 63 (9.7) | 0.45 |
| Male | 37/58 (63.8) | 12/20 (60) | 25/38 (65.8) | 0.78 | 14/17 (82.4) | 4/5 (80) | 10/12 (83.3) | 1 |
| Current smoker | 28/58 (48.3) | 9/20 (45) | 19/38 (50) | 0.79 | 8/17 (47.1) | 2/5 (40) | 6/12 (50) | 1 |
| Pack-years | 48.2 (16.9) | 49.4 (18.9) | 47.5 (15.9) | 0.71 | 44.6 (12.9) | 40.5 (11.6) | 46.3 (13.5) | 0.39 |
| FEV1% Predicted | 86.5 (17.7) | 87.8 (16.7) | 85.7 (18.5) | 0.66 | 69.5 (16.2) | 71 (17.7) | 68.9 (16.3) | 0.83 |
| FEV1/FVC Ratio | 72.1 (7.7) | 75.1 (6.3) | 70.4 (8) | 0.02 | 67 (8.1) | 66.8 (8.5) | 67.1 (8.3) | 0.95 |
| COPD (FEV1% < 80 & FEV1/FVC < 70) | 11/58 (19) | 2/20 (10) | 9/38 (23.7) | 0.3 | 11/17 (64.7) | 3/5 (60) | 8/12 (66.7) | 1 |
| Histology | | | | <0.001 | | | | <0.001 |
| Normal | 11/58 (19) | 11/20 (55) | | | 1/17 (5.9) | 1/5 (20) | | |
| Hyperplasia | 9/58 (15.5) | 9/20 (45) | | | 4/17 (23.5) | 4/5 (80) | | |
| Metaplasia | 0/58 (0) | | | | 0/17 (0) | | | |
| Mild Dysplasia | 29/58 (50) | | 29/38 (76.3) | | 6/17 (35.3) | | 6/12 (50) | |
| Moderate Dysplasia | 6/58 (10.3) | | 6/38 (15.8) | | 6/17 (35.3) | | 6/12 (50) | |
| Severe Dysplasia | 3/58 (5.2) | | 3/38 (7.9) | | | | 0/12 (0) | |

Data are means (SD) for continuous variables and proportions (%) dichotomous variables.
Reads are expressed in millions denoted by M.
P* values are for the comparison of subjects with and without premalignant lesions.
Two sample t-tests were used for continuous variables; Fisher's exact test was used for factors.

SUPPLEMENTAL TABLE 5

Alignment statistics of the British Columbia Lung Health Study Discovery and the Roswell Park Cancer Institute cohort

| Factor | BC-LHS Discovery Set | | | | BC-LHS Validation Set | | | | RPCI |
|---|---|---|---|---|---|---|---|---|---|
| | Overall (n = 58) | No Lesions (n = 20) | Lesions (n = 38) | P* | Overall (n = 17) | No Lesions (n = 5) | Lesions (n = 12) | P* | Overall (n = 51) |
| Total Alignments | 90M (16M) | 98M (15M) | 91M (17M) | 0.67 | 93M (22M) | 94M (18M) | 92M (24M) | 0.86 | 95M (15M) |
| Unique Alignments | 83M (15M) | 82M (13M) | 83M (16M) | 0.65 | 85M (20M) | 86M (16M) | 84M (22M) | 0.85 | |
| Properly Paired Alignments | 66M (1.2M) | 65M (11M) | 67M (12M) | 0.63 | 68M (16M) | 69M (13M) | 67M (17M) | 0.86 | 65M (9.6M) |
| Genebody 80/20 Ratio | 1.3 (0.2) | 1.3 (0.1) | 1.3 (0.2) | 0.39 | 1.3 (0.3) | 1.2 (0.1) | 1.4 (0.3) | 0.15 | 1.8 (0.2) |
| Mean GC Content | 48.1 (3.4) | 47.5 (2.7) | 48.4 (3.6) | 0.33 | 47.4 (3.8) | 46.9 (3.8) | 47.6 (3.9) | 0.74 | 49.2 (1.4) |

Data are means (SD).
Reads are expressed in millions denoted by M.
P* values are for two sample t-tests for comparison of subjects with and without premalignant lesions.

SUPPLEMENTAL TABLE 6

Demographic and clinical characteristics of the Roswell Park Cancer Institute Cohort (n = 51 samples from n = 23 subjects)

| Factor | Overall | Regressing | Progressing Stable | P* |
|---|---|---|---|---|
| No. Samples | 51 | 34 | 22 | |
| No. Sample Pairs | 28 | 17 | 11 | |
| No. Patients** | 23 | 16 | 10 | |
| Time between Procedures (Days) | 343.8 (171.9) | 350.9 (199.6) | 332.8 (125.9) | 0.77 |
| Histological Grade Change | −0.9 (1.7) | −1.9 (1.0) | 0.7 (1.3) | <0.001 |
| Worst Histological Lesion Observed | | | | |
| Normal | 5/51 (9.8) | 4/34 (11.8) | 2/22 (9.1) | 0.038 |
| Hyperplasia | 6/51 (11.8) | 5/34 (14.7) | 1/22 (4.5) | |
| Metaplasia | 9/51 (17.6) | 8/34 (23.5) | 1/22 (4.5) | |
| Mild Dysplasia | 3/51 (5.9) | 3/34 (8.8) | 0 (0) | |
| Moderate Dysplasia | 20/51 (39.2) | 9/34 (26.5) | 15/22 (68.2) | |
| Severe Dysplasia | 8/51 (15.7) | 5/34 (14.7) | 3/22 (13.6) | |
| Age at Baseline | 58.1 (6.5) | 58.4 (6.9) | 57.6 (6.1) | 1 |
| Male | 13/28 (46.4) | 7/17 (41.2) | 6/11 (54.5) | 0.7 |
| Ever smoker at Baseline | 27/28 (96.4) | 17/17 (100) | 10/11 (90.9) | 0.39 |
| Pack-years at Baseline | 48.1 (22) | 49.8 (24.8) | 45.4 (17.6) | 1 |

Data are means (SD) for continuous variables and proportions (%) for dichotomous variables. P* values are for the comparison of samples, sample pairs, or patients classified as having regressing or progressing/stable PMLs. Two sample t-tests were used for continuous variables; Fisher's exact test was used for factors. **Among the 23 patients, 3 patients had 2 sample pairs where one pair was classified as regressing and the other as progressing/stable. These patients are counted in both the regressing and progressing/stable columns

Dataset 1. Ensembl IDs for genes used to predict smoking status.

ENSG00000151632
ENSG00000125398
ENSG00000159228
ENSG00000109586
ENSG00000049089
ENSG00000198431
ENSG00000140961
ENSG00000117450
ENSG00000111058
ENSG00000198074
ENSG00000001084
ENSG00000168309
ENSG00000108602
ENSG00000065833
ENSG00000215182
ENSG00000079819
ENSG00000117983
ENSG00000163931
ENSG00000173376
ENSG00000197838
ENSG00000176153
ENSG00000136810
ENSG00000137642
ENSG00000134873
ENSG00000172765
ENSG00000154040
ENSG00000048707
ENSG00000123124
ENSG00000102359
ENSG00000197747
ENSG00000103222
ENSG00000103647
ENSG00000099968
ENSG00000196344
ENSG00000140939
ENSG00000167996
ENSG00000006125
ENSG00000149256
ENSG00000010404
ENSG00000023909

Dataset 1. Ensembl IDs for genes used to predict smoking status.

ENSG00000077147
ENSG00000134775
ENSG00000177156
ENSG00000123700
ENSG00000124664
ENSG00000197712
ENSG00000154822
ENSG00000086548
ENSG00000137573
ENSG00000100012
ENSG00000136205
ENSG00000138061
ENSG00000104341
ENSG00000151012
ENSG00000039537
ENSG00000181458
ENSG00000006210
ENSG00000078596
ENSG00000117394
ENSG00000106541
ENSG00000125798
ENSG00000109854
ENSG00000196139
ENSG00000162496
ENSG00000181019
ENSG00000140526
ENSG00000166670
ENSG00000198417
ENSG00000162804
ENSG00000105388
ENSG00000069764
ENSG00000108924
ENSG00000171903
EN5G00000085662
ENSG00000137648
ENSG00000125144
ENSG00000113924
ENSG00000134827
ENSG00000142655
ENSG00000139629
ENSG00000160180
ENSG00000124107
ENSG00000119514
ENSG00000227051
ENSG00000144711
ENSG00000101445
ENSG00000137337
ENSG00000114638
ENSG00000142657
ENSG00000130595
ENSG00000145147
ENSG00000087842
ENSG00000133985
ENSG00000125813

Dataset 2. Results of pathway enrichment using ROAST (FDR < 0.05). The column "Direction" refers to pathway enrichment among genes up-regulated (Up) or down-regulated (Down) in the presence of PMLs.

| Pathway | NGenes | PropDown | PropUp | Direction | PValue | FDR |
|---|---|---|---|---|---|---|
| REACTOME_METABOLISM_OF_PROTEINS | 382 | 0.091623 | 0.544503 | Up | 0.002 | 0.0128 |
| REACTOME_METABOLISM_OF_RNA | 251 | 0.139442 | 0.494024 | Up | 0.002 | 0.0128 |
| REACTOME_METABOLISM_OF_MRNA | 206 | 0.131068 | 0.533981 | Up | 0.002 | 0.0128 |
| KEGG_HUNTINGTONS_DISEASE | 158 | 0.126582 | 0.607595 | Up | 0.002 | 0.0128 |
| KEGG_ALZHEIMERS_DISEASE | 141 | 0.120567 | 0.631206 | Up | 0.002 | 0.0128 |
| REACTOME_TRANSLATION | 141 | 0.042553 | 0.780142 | Up | 0.002 | 0.0128 |
| REACTOME_INFLUENZA_LIFE_CYCLE | 133 | 0.075188 | 0.691729 | Up | 0.002 | 0.0128 |
| REACTOME_TCA_CYCLE_AND_RESPIRATORY_ELECTRON_TRANSPORT | 125 | 0.088 | 0.64 | Up | 0.002 | 0.0128 |
| KEGG_OXIDATIVE_PHOSPHORYLATION | 117 | 0.042735 | 0.692308 | Up | 0.002 | 0.0128 |
| KEGG_PARKINSONS_DISEASE | 113 | 0.079646 | 0.699115 | Up | 0.002 | 0.0128 |
| REACTOME_SRP_DEPENDENT_COTRANSLATIONAL_PROTEIN_TARGETING_TO_MEMBRANE | 105 | 0.019048 | 0.885714 | Up | 0.002 | 0.0128 |
| REACTOME_NONSENSE_MEDIATED_DECAY_ENHANCED_BY_THE_EXON_JUNCTION_COMPLEX | 103 | 0.07767 | 0.776699 | Up | 0.002 | 0.0128 |
| REACTOME_3_UTR_MEDIATED_TRANSLATIONAL_REGULATION | 102 | 0.029412 | 0.843137 | Up | 0.002 | 0.0128 |
| REACTOME_SIGNALING_BY_RHO_GTPASES | 93 | 0.387097 | 0.150538 | Down | 0.002 | 0.0128 |
| REACTOME_RESPIRATORY_ELECTRON_TRANSPORT_ATP_SYNTHESIS_BY_CHEMIOSMOTIC COUPLING AND HEAT_PRODUCTION_BY_UNCOUPLING_PROTEINS_ | 91 | 0.021978 | 0.758242 | Up | 0.002 | 0.0128 |
| KEGG_JAK_STAT_SIGNALING_PATHWAY | 87 | 0.321839 | 0.126437 | Down | 0.002 | 0.0128 |
| KEGG_PYRIMIDINE_METABOLISM | 84 | 0.154762 | 0.380952 | Up | 0.002 | 0.0128 |
| KEGG_RIBOSOME | 83 | 0.012048 | 0.939759 | Up | 0.002 | 0.0128 |
| REACTOME_PEPTIDE_CHAIN_ELONGATION | 82 | 0.012195 | 0.939024 | Up | 0.002 | 0.0128 |
| REACTOME_RESPIRATORY_ELECTRON_TRANSPORT | 74 | 0.013514 | 0.756757 | Up | 0.002 | 0.0128 |
| PID_HDAC_CLASSI_PATHWAY | 60 | 0.366667 | 0.15 | Down | 0.002 | 0.0128 |
| PID_MYC_REPRESSPATHWAY | 55 | 0.381818 | 0.127273 | Down | 0.002 | 0.0128 |
| REACTOME_ACTIVATION_OF_THE_MRNA_UPON_BINDING_OF_THE_CAP_BINDING_COMPLEX_AND_SUBSEQUENT_BINDING_TO_43S | 55 | 0.054545 | 0.745455 | Up | 0.002 | 0.0128 |
| PID_AVB3_INTEGRIN_PATHWAY | 53 | 0.320755 | 0.132075 | Down | 0.002 | 0.0128 |
| KEGG_ADIPOCYTOKINE_SIGNALING_PATHWAY | 51 | 0.411765 | 0.176471 | Down | 0.002 | 0.0128 |
| REACTOME_MITOCHONDRIAL_PROTEIN_IMPORT | 49 | 0.102041 | 0.530612 | Up | 0.002 | 0.0128 |
| REACTOME_FORMATION_OF_THE_TERNARY_COMPLEX_AND_SUBSEQUENTLY_THE_43S_COMPLEX | 47 | 0.042553 | 0.829787 | Up | 0.002 | 0.0128 |
| KEGG_CARDIAC_MUSCLE_CONTRACTION | 43 | 0.116279 | 0.55814 | Up | 0.002 | 0.0128 |
| KEGG_LYSINE_DEGRADATION | 42 | 0.428571 | 0.166667 | Down | 0.002 | 0.0128 |

-continued

Dataset 2. Results of pathway enrichment using ROAST (FDR < 0.05).
The column "Direction" refers to pathway enrichment among genes up-
regulated (Up) or down-regulated (Down) in the presence of PMLs.

| Pathway | NGenes | PropDown | PropUp | Direction | PValue | FDR |
|---|---|---|---|---|---|---|
| PID_IL4_2PATHWAY | 42 | 0.380952 | 0.119048 | Down | 0.002 | 0.0128 |
| REACTOME_FORMATION_OF_RNA_POL_II_ELONGATION_COMPLEX_ | 41 | 0.170732 | 0.439024 | Up | 0.002 | 0.0128 |
| KEGG_NOTCH_SIGNALING_PATHWAY | 40 | 0.425 | 0.125 | Down | 0.002 | 0.0128 |
| PID_RHOA_REG_PATHWAY | 40 | 0.475 | 0.125 | Down | 0.002 | 0.0128 |
| REACTOME_NRAGE_SIGNALS_DEATH_THROUGH_JNK | 39 | 0.358974 | 0.153846 | Down | 0.002 | 0.0128 |
| REACTOME_PRE_NOTCH_EXPRESSION_AND_PROCESSING | 38 | 0.342105 | 0.131579 | Down | 0.002 | 0.0128 |
| REACTOME_NCAM_SIGNALING_FOR_NEURITE_OUT_GROWTH | 37 | 0.459459 | 0.108108 | Down | 0.002 | 0.0128 |
| ST_GA13_PATHWAY | 33 | 0.424242 | 0.121212 | Down | 0.002 | 0.0128 |
| PID_RAC1_REG_PATHWAY | 33 | 0.454545 | 0.121212 | Down | 0.002 | 0.0128 |
| REACTOME_BMAL1_CLOCK_NPAS2_ACTIVATES_CIRCADIAN_EXPRESSION | 33 | 0.484848 | 0.090909 | Down | 0.002 | 0.0128 |
| BIOCARTA_CARM_ER_PATHWAY | 32 | 0.34375 | 0.125 | Down | 0.002 | 0.0128 |
| REACTOME_G1_PHASE | 32 | 0.09375 | 0.5 | Up | 0.002 | 0.0128 |
| REACTOME_FORMATION_OF_THE_HIV1_EARLY_ELONGATION_COMPLEX | 31 | 0.129032 | 0.483871 | Up | 0.002 | 0.0128 |
| KEGG_PROPANOATE_METABOLISM | 30 | 0.1 | 0.433333 | Up | 0.002 | 0.0128 |
| PID_FRA_PATHWAY | 28 | 0.428571 | 0.071429 | Down | 0.002 | 0.0128 |
| REACTOME_PURINE_METABOLISM | 28 | 0.178571 | 0.392857 | Up | 0.002 | 0.0128 |
| KEGG_BUTANOATE_METABOLISM | 27 | 0.037037 | 0.481481 | Up | 0.002 | 0.0128 |
| BIOCARTA_MYOSIN_PATHWAY | 27 | 0.296296 | 0.111111 | Down | 0.002 | 0.0128 |
| REACTOME_MRNA_CAPPING | 27 | 0.111111 | 0.481481 | Up | 0.002 | 0.0128 |
| REACTOME_FORMATION_OF_TRANSCRIPTION_COUPLED_NER_TC_NER_REPAIR_COMPLEX | 27 | 0.074074 | 0.518519 | Up | 0.002 | 0.0128 |
| REACTOME_PRE_NOTCH_TRANSCRIPTION_AND_TRANSLATION | 25 | 0.48 | 0.12 | Down | 0.002 | 0.0128 |
| ST_GAQ_PATHWAY | 24 | 0.5 | 0.166667 | Down | 0.002 | 0.0128 |
| REACTOME_RORA_ACTIVATES_CIRCADIAN_EXPRESSION | 24 | 0.5 | 0.041667 | Down | 0.002 | 0.0128 |
| REACTOME_ENDOSOMAL_SORTING_COMPLEX_REQUIRED_FOR_TRANSPORT_ESCRT | 24 | 0.083333 | 0.541667 | Up | 0.002 | 0.0128 |
| BIOCARTA_HDAC_PATHWAY | 23 | 0.478261 | 0.130435 | Down | 0.002 | 0.0128 |
| PID_HDAC_CLASSIII_PATHWAY | 22 | 0.454545 | 0.136364 | Down | 0.002 | 0.0128 |
| PID_RXR_VDR_PATHWAY | 22 | 0.409091 | 0.045455 | Down | 0.002 | 0.0128 |
| REACTOME_PREFOLDIN_MEDIATED_TRANSFER_OF_SUBSTRATE_TO_CCT_TRIC | 21 | 0.047619 | 0.571429 | Up | 0.002 | 0.0128 |
| REACTOME_SIGNALING_BY_FGFR1_MUTANTS | 19 | 0.421053 | 0.157895 | Down | 0.002 | 0.0128 |
| REACTOME_SIGNALING_BY_FGFR1_FUSION_MUTANTS | 18 | 0.444444 | 0.111111 | Down | 0.002 | 0.0128 |
| BIOCARTA_TNFR2_PATHWAY | 17 | 0.529412 | 0.117647 | Down | 0.002 | 0.0128 |
| BIOCARTA_RELA_PATHWAY | 15 | 0.533333 | 0.2 | Down | 0.002 | 0.0128 |
| REACTOME_FORMATION_OF_ATP_BY_CHEMIOSMOTIC_COUPLING | 15 | 0 | 0.866667 | Up | 0.002 | 0.0128 |
| REACTOME_EARLY_PHASE_OF_HIV_LIFE_CYCLE | 13 | 0 | 0.538462 | Up | 0.002 | 0.0128 |
| BIOCARTA_VDR_PATHWAY | 12 | 0.583333 | 0 | Down | 0.002 | 0.0128 |
| BIOCARTA_CARM1_PATHWAY | 12 | 0.416667 | 0.166667 | Down | 0.002 | 0.0128 |
| REACTOME_SEMA3A_PLEXIN_REPULSION_SIGNALING_BY_INHIBITING_INTEGRIN_ADHESION | 12 | 0.5 | 0.166667 | Down | 0.002 | 0.0128 |
| BIOCARTA_ETC_PATHWAY | 11 | 0 | 0.727273 | Up | 0.002 | 0.0128 |
| BIOCARTA_EGFR_SMRTE_PATHWAY | 11 | 0.454545 | 0 | Down | 0.002 | 0.0128 |
| BIOCARTA_P27_PATHWAY | 11 | 0.090909 | 0.454545 | Up | 0.002 | 0.0128 |
| PID_LPA4_PATHWAY | 11 | 0.545455 | 0 | Down | 0.002 | 0.0128 |
| REACTOME_PURINE_SALVAGE | 11 | 0.181818 | 0.727273 | Up | 0.002 | 0.0128 |
| BIOCARTA_RAB_PATHWAY | 10 | 0 | 0.9 | Up | 0.002 | 0.0128 |
| REACTOME_ASSOCIATION_OF_LICENSING_FACTORS_WITH_THE_PRE_REPLICATIVE_COMPLEX | 9 | 0.111111 | 0.555556 | Up | 0.002 | 0.0128 |
| REACTOME_GLUTAMATE_NEUROTRANSMITTER_RELEASE_CYCLE | 9 | 0.555556 | 0 | Down | 0.002 | 0.0128 |
| REACTOME_INTEGRATION_OF_PROVIRUS | 8 | 0 | 0.625 | Up | 0.002 | 0.0128 |
| BIOCARTA_NUCLEARRS_PATHWAY | 6 | 0.5 | 0 | Down | 0.002 | 0.0128 |
| REACTOME_ACYL_CHAIN_REMODELLING_OF_PI | 6 | 0 | 0.666667 | Up | 0.002 | 0.0128 |
| REACTOME_ENDOGENOUS_STEROLS | 6 | 0.5 | 0.166667 | Down | 0.002 | 0.0128 |
| REACTOME_SYNTHESIS_SECRETION_AND_DEACYLATION_OF_GHRELIN | 6 | 0 | 0.833333 | Up | 0.002 | 0.0128 |
| REACTOME_INTERACTION_BETWEEN_L1_AND_ANKYRINS | 6 | 1 | 0 | Down | 0.002 | 0.0128 |
| KEGG_TAURINE_AND_HYPOTAURINE_METABOLISM | 5 | 0.4 | 0.2 | Down | 0.002 | 0.0128 |
| REACTOME_DOPAMINE_NEUROTRANSMITTER_RELEASE_CYCLE | 5 | 0.6 | 0.2 | Down | 0.002 | 0.0128 |
| REACTOME_ACETYLCHOLINE_NEUROTRANSMITTER_RELEASE_CYCLE | 4 | 0.75 | 0 | Down | 0.002 | 0.0128 |
| REACTOME_NUCLEAR_RECEPTOR_TRANSCRIPTION_PATHWAY | 34 | 0.294118 | 0.058824 | Down | 0.002 | 0.0128 |
| KEGG_PROTEIN_EXPORT | 23 | 0.043478 | 0.652174 | Up | 0.002 | 0.0128 |
| ST_INTERLEUKIN_4_PATHWAY | 23 | 0.391304 | 0.086957 | Down | 0.002 | 0.0128 |
| REACTOME_TRAF6_MEDIATED_IRF7_ACTIVATION | 17 | 0.529412 | 0 | Down | 0.002 | 0.0128 |
| PID_CIRCADIANPATHWAY | 15 | 0.533333 | 0.066667 | Down | 0.002 | 0.0128 |
| REACTOME_VIRAL_MESSENGER_RNA_SYNTHESIS | 14 | 0.071429 | 0.642857 | Up | 0.002 | 0.0128 |

Dataset 2. Results of pathway enrichment using ROAST (FDR < 0.05).
The column "Direction" refers to pathway enrichment among genes up-
regulated (Up) or down-regulated (Down) in the presence of PMLs.

| Pathway | NGenes | PropDown | PropUp | Direction | PValue | FDR |
|---|---|---|---|---|---|---|
| REACTOME_METABOLISM_OF_POLYAMINES | 13 | 0.076923 | 0.538462 | Up | 0.002 | 0.0128 |
| REACTOME_NOTCH_HLH_TRANSCRIPTION_PATHWAY | 11 | 0.454545 | 0.090909 | Down | 0.002 | 0.0128 |
| REACTOME_ADENYLATE_CYCLASE_ACTIVATING_PATHWAY | 7 | 0.571429 | 0 | Down | 0.002 | 0.0128 |
| ST_STAT3_PATHWAY | 9 | 0.555556 | 0 | Down | 0.002 | 0.0128 |
| REACTOME_BINDING_AND_ENTRY_OF_HIV_VIRION | 4 | 0 | 0.5 | Up | 0.002 | 0.0128 |
| PID_CD40_PATHWAY | 27 | 0.333333 | 0.037037 | Down | 0.002 | 0.0128 |
| REACTOME_CD28_DEPENDENT_PI3K_AKT_SIGNALING | 19 | 0.473684 | 0.052632 | Down | 0.002 | 0.0128 |
| BIOCARTA_RARRXR_PATHWAY | 15 | 0.4 | 0.066667 | Down | 0.002 | 0.0128 |
| BIOCARTA_PITX2_PATHWAY | 13 | 0.384615 | 0 | Down | 0.002 | 0.0128 |
| REACTOME_INCRETIN_SYNTHESIS_SECRE-TION_AND_INACTIVATION | 9 | 0 | 0.444444 | Up | 0.002 | 0.0128 |
| REACTOME_CLASS_C_3_METABOTROPIC_GLUTA-MATE_PHEROMONE_RECEPTORS | 2 | 0.5 | 0 | Down | 0.002 | 0.0128 |
| BIOCARTA_EGF_PATHWAY | 31 | 0.258065 | 0.032258 | Down | 0.002 | 0.0128 |
| REACTOME_HDL_MEDIATED_LIPID_TRANSPORT | 11 | 0.454545 | 0 | Down | 0.002 | 0.0128 |
| REACTOME_GENERIC_TRANSCRIPTION_PATHWAY | 292 | 0.349315 | 0.10274 | Down | 0.004 | 0.0283 |
| REACTOME_DEVELOPMENTAL_BIOLOGY | 270 | 0.333333 | 0.188889 | Down | 0.004 | 0.0283 |
| REACTOME_SIGNALING_BY_PDGF | 94 | 0.361702 | 0.148936 | Down | 0.004 | 0.0283 |
| PID_SMAD2_3NUCLEARPATHWAY | 68 | 0.411765 | 0.102941 | Down | 0.004 | 0.0283 |
| PID_REG_GR_PATHWAY | 60 | 0.366667 | 0.15 | Down | 0.004 | 0.0283 |
| KEGG_ECM_RECEPTOR_INTERACTION | 51 | 0.352941 | 0.117647 | Down | 0.004 | 0.0283 |
| REACTOME_CIRCADIAN_CLOCK | 48 | 0.416667 | 0.125 | Down | 0.004 | 0.0283 |
| KEGG_PPAR_SIGNALING_PATHWAY | 43 | 0.348837 | 0.162791 | Down | 0.004 | 0.0283 |
| SIG_BCR_SIGNALING_PATHWAY | 41 | 0.317073 | 0.04878 | Down | 0.004 | 0.0283 |
| REACTOME_TRANSCRIPTION_COUPLED_NER_TC_NER | 41 | 0.097561 | 0.439024 | Up | 0.004 | 0.0283 |
| REACTOME_RNA_POL_II_TRANSCRIPTION_PRE_INITI-ATION_AND_PROMOTER_OPENING | 38 | 0.131579 | 0.447368 | Up | 0.004 | 0.0283 |
| KEGG_AMYOTROPHIC_LATERAL_SCLEROSIS_ALS | 37 | 0.189189 | 0.324324 | Up | 0.004 | 0.0283 |
| KEGG_ABC_TRANSPORTERS | 31 | 0.516129 | 0.129032 | Down | 0.004 | 0.0283 |
| BIOCARTA_PAR1_PATHWAY | 31 | 0.290323 | 0.16129 | Down | 0.004 | 0.0283 |
| REACTOME_COLLAGEN_FORMATION | 31 | 0.451613 | 0.096774 | Down | 0.004 | 0.0283 |
| PID_RETINOIC_ACID_PATHWAY | 28 | 0.392857 | 0.178571 | Down | 0.004 | 0.0283 |
| REACTOME_CIRCADIAN_REPRESSION_OF_EX-PRESSION_BY_REV_ERBA | 22 | 0.5 | 0.045455 | Down | 0.004 | 0.0283 |
| KEGG_O_GLYCAN_BIOSYNTHESIS | 21 | 0.047619 | 0.619048 | Up | 0.004 | 0.0283 |
| REACTOME_YAP1_AND_WWTR1_TAZ_STIM-ULATED_GENE_EXPRESSION | 20 | 0.4 | 0.1 | Down | 0.004 | 0.0283 |
| BIOCARTA_AKT_PATHWAY | 18 | 0.444444 | 0.166667 | Down | 0.004 | 0.0283 |
| BIOCARTA_IL7_PATHWAY | 16 | 0.4375 | 0.125 | Down | 0.004 | 0.0283 |
| REACTOME_OXYGEN_DEPENDENT_PROLINE_HYDROX-YLATION_OF_HYPOXIA_INDUCIBLE_FACTOR_ALPHA | 15 | 0.066667 | 0.533333 | Up | 0.004 | 0.0283 |
| BIOCARTA_IL22BP_PATHWAY | 14 | 0.5 | 0 | Down | 0.004 | 0.0283 |
| REACTOME_NCAM1_INTERACTIONS | 14 | 0.571429 | 0 | Down | 0.004 | 0.0283 |
| REACTOME_EFFECTS_OF_PIP2_HYDROLYSIS | 14 | 0.428571 | 0.071429 | Down | 0.004 | 0.0283 |
| KEGG_RIBOFLAVIN_METABOLISM | 13 | 0.076923 | 0.461538 | Up | 0.004 | 0.0283 |
| REACTOME_TRAF3_DEPENDENT_IRF_ACTIVATION_PATHWAY | 13 | 0.461538 | 0 | Down | 0.004 | 0.0283 |
| BIOCARTA_EPONFKB_PATHWAY | 9 | 0.666667 | 0 | Down | 0.004 | 0.0283 |
| REACTOME_IL_6_SIGNALING | 9 | 0.444444 | 0 | Down | 0.004 | 0.0283 |
| REACTOME_SYNTHESIS_SECRETION_AND_IN-ACTIVATION_OF_GIP | 7 | 0 | 0.571429 | Up | 0.004 | 0.0283 |
| BIOCARTA_GABA_PATHWAY | 3 | 0 | 0.666667 | Up | 0.004 | 0.0283 |
| REACTOME_INFLUENZA_VIRAL_RNA_TRAN-SCRIPTION_AND_REPLICATION | 98 | 0.020408 | 0.867347 | Up | 0.004 | 0.0283 |
| REACTOME_LIPOPROTEIN_METABOLISM | 19 | 0.315789 | 0.052632 | Down | 0.004 | 0.0283 |
| REACTOME_ACYL_CHAIN_REMODELLING_OF_PG | 7 | 0 | 0.571429 | Up | 0.004 | 0.0283 |
| BIOCARTA_PDGF_PATHWAY | 30 | 0.266667 | 0.033333 | Down | 0.004 | 0.0283 |
| REACTOME_SYNTHESIS_SECRETION_AND_IN-ACTIVATION_OF_GLP1 | 8 | 0 | 0.5 | Up | 0.004 | 0.0283 |
| BIOCARTA_SALMONELLA_PATHWAY | 11 | 0 | 0.636364 | Up | 0.004 | 0.0283 |
| REACTOME_AXON_GUIDANCE | 173 | 0.34104 | 0.179191 | Down | 0.006 | 0.0386 |
| REACTOME_SIGNALING_BY_NOTCH | 90 | 0.311111 | 0.2 | Down | 0.006 | 0.0386 |
| KEGG_PEROXISOME | 71 | 0.098592 | 0.352113 | Up | 0.006 | 0.0386 |
| ST_INTEGRIN_SIGNALING_PATHWAY | 71 | 0.323944 | 0.126761 | Down | 0.006 | 0.0386 |
| REACTOME_SEMAPHORIN_INTERACTIONS | 58 | 0.310345 | 0.224138 | Down | 0.006 | 0.0386 |
| REACTOME_RNA_POL_II_PRE_TRANSCRIPTION_EVENTS | 57 | 0.175439 | 0.385965 | Up | 0.006 | 0.0386 |
| KEGG_ACUTE_MYELOID_LEUKEMIA | 53 | 0.320755 | 0.132075 | Down | 0.006 | 0.0386 |
| REACTOME_NUCLEOTIDE_EXCISION_REPAIR | 46 | 0.108696 | 0.391304 | Up | 0.006 | 0.0386 |
| REACTOME_EXTRACELLULAR_MATRIX_ORGANIZATION | 43 | 0.372093 | 0.093023 | Down | 0.006 | 0.0386 |
| KEGG_VALINE_LEUCINE_AND_ISOLEUCINE_DEGRADATION | 40 | 0.075 | 0.45 | Up | 0.006 | 0.0386 |
| PID_HDAC_CLASSII_PATHWAY | 31 | 0.419355 | 0.16129 | Down | 0.006 | 0.0386 |
| REACTOME_ELONGATION_ARREST_AND_RECOVERY | 31 | 0.193548 | 0.451613 | Up | 0.006 | 0.0386 |
| KEGG_RNA_POLYMERASE | 27 | 0.074074 | 0.481481 | Up | 0.006 | 0.0386 |
| SIG_IL4RECEPTOR_IN_B_LYPHOCYTES | 25 | 0.32 | 0.04 | Down | 0.006 | 0.0386 |

Dataset 2. Results of pathway enrichment using ROAST (FDR < 0.05).
The column "Direction" refers to pathway enrichment among genes up-
regulated (Up) or down-regulated (Down) in the presence of PMLs.

| Pathway | NGenes | PropDown | PropUp | Direction | PValue | FDR |
|---|---|---|---|---|---|---|
| PID_REELINPATHWAY | 24 | 0.416667 | 0.166667 | Down | 0.006 | 0.0386 |
| REACTOME_ABC_FAMILY_PROTEINS_MEDIATED_TRANSPORT | 23 | 0.521739 | 0.217391 | Down | 0.006 | 0.0386 |
| REACTOME_ABORTIVE_ELONGATION_OF_HIV1_TRAN-SCRIPT_IN_THE_ABSENCE_OF_TAT | 23 | 0.130435 | 0.478261 | Up | 0.006 | 0.0386 |
| BIOCARTA_GH_PATHWAY | 22 | 0.363636 | 0.045455 | Down | 0.006 | 0.0386 |
| REACTOME_RNA_POL_III_CHAIN_ELONGATION | 16 | 0.0625 | 0.4375 | Up | 0.006 | 0.0386 |
| BIOCARTA_CD40_PATHWAY | 14 | 0.5 | 0.071429 | Down | 0.006 | 0.0386 |
| REACTOME_ACYL_CHAIN_REMODELLING_OF_PC | 12 | 0.166667 | 0.5 | Up | 0.006 | 0.0386 |
| REACTOME_CASPASE_MEDIATED_CLEAV-AGE_OF_CYTOSKELETAL_PROTEINS | 11 | 0.545455 | 0.272727 | Down | 0.006 | 0.0386 |
| REACTOME_ORGANIC_CATION_ANION_ZWIT-TERION_TRANSPORT | 5 | 0.6 | 0 | Down | 0.006 | 0.0386 |
| KEGG_FOCAL_ADHESION | 145 | 0.296552 | 0.151724 | Down | 0.006 | 0.0386 |
| PID_TNFPATHWAY | 43 | 0.395349 | 0.093023 | Down | 0.006 | 0.0386 |
| REACTOME_APC_CDC20_MEDIATED_DEGRADATION_OF_NEK2A | 18 | 0.111111 | 0.388889 | Up | 0.006 | 0.0386 |
| BIOCARTA_ETS_PATHWAY | 17 | 0.352941 | 0.117647 | Down | 0.006 | 0.0386 |
| PID_HIF1APATHWAY | 18 | 0.166667 | 0.333333 | Up | 0.006 | 0.0386 |
| KEGG_TRYPTOPHAN_METABOLISM | 25 | 0.08 | 0.28 | Up | 0.006 | 0.0386 |
| REACTOME_N_GLYCAN_ANTENNAE_ELONGATION | 10 | 0.1 | 0.5 | Up | 0.006 | 0.0386 |
| REACTOME_AMINO_ACID_TRANS-PORT_ACROSS_THE_PLASMA_MEMBRANE | 18 | 0.388889 | 0 | Down | 0.006 | 0.0386 |

Dataset 3. GSEA results detailing lung cancer associated dataset enrichment
among genes differentially expressed in the airway field associated with PMLs

| Gene Set | SIZE | ES | NES | NOM p-val | FDR q-val | FWER p-val | RANK AT MAX | LEADING EDGE |
|---|---|---|---|---|---|---|---|---|
| OOI ET AL. EARLY, DN-REG, PVN P < 0.05, TVN P < 0.05 | 26 | −0.56 | −1.87 | 0.002 | 0.005 | 0.017 | 2634 | tags = 46%, list = 19%, signal = 57% |
| OOI ET AL. EARLY, UP-REG, PVN P < 0.05, TVN P < 0.05 | 487 | 0.36 | 2.11 | 0 | 0 | 0.001 | 3850 | tags = 43%, list = 28%, signal = 58% |
| OOI ET AL. STEPWISE, DN-REG, PVN P < 0.05, TVP P < 0.05, TVN P < 0.05 | 111 | −0.31 | −1.4 | 0.028 | 0.064 | 0.794 | 3041 | tags = 27%, list = 22%, signal = 34% |
| OOI ET AL. STEPWISE, UP-REG, PVN P < 0.05, TVP P < 0.05, TVN P < 0.05 | 518 | 0.29 | 1.73 | 0 | 0.005 | 0.076 | 2858 | tags = 29%, list = 21%, signal = 35% |
| OOI ET AL. LATE, DN-REG, TVP P < 0.05, TVN P < 0.05 | 12 | −0.64 | −1.74 | 0.012 | 0.009 | 0.082 | 1784 | tags = 58%, list = 13%, signal = 67% |
| OOI ET AL. LATE, UP-REG, TVP P < 0.05, TVN P < 0.05 | 54 | 0.53 | 2.24 | 0 | 0 | 0 | 3052 | tags = 46%, list = 22%, signal = 59 |
| TCGA, SCCVN, DN-REG, 200 | 119 | −0.37 | −1.67 | 0.001 | 0.014 | 0.152 | 3526 | tags = 36%, list = 25%, signal = 48% |
| TCGA, SCCVN, UP-REG, 200 | 146 | 0.28 | 1.41 | 0.013 | 0.048 | 0.6 | 3950 | tags = 40%, list = 28%, signal = 55% |
| GSE18842, TVN, DN-REG, 200 | 111 | −0.42 | −1.87 | 0 | 0.007 | 0.016 | 3526 | tags = 41%, list = 25%, signal = 54% |
| GSE18842, TVN, UP-REG, 200 | 149 | 0.43 | 2.14 | 0 | 0 | 0.001 | 4601 | tags = 52%, list = 33%, signal = 77% |
| GSE19188, SCCVN, DN-REG, 200 | 115 | −0.35 | −1.55 | 0.006 | 0.027 | 0.371 | 4837 | tags = 50%, list = 35%, signal = 75% |
| GSE19188,SCCVN, UP-REG, 200 | 147 | 0.42 | 2.14 | 0 | 0 | 0.001 | 3596 | tags = 41%, list = 26%, signal = 55% |
| GSE4115, CAVN, DN-REG, 200 | 108 | −0.35 | −1.56 | 0.005 | 0.031 | 0.365 | 3066 | tags = 31%, list = 22%, signal = 39% |
| GSE4115, CAVN, UP-REG, 200 | 197 | 0.45 | 2.36 | 0 | 0 | 0 | 3781 | tags = 55%, list = 27%, signal = 74% |

REFERENCES

1. Hackett N R, Heguy A, Harvey B G, et al. (2003) Variability of antioxidant-related gene expression in the airway epithelium of cigarette smokers. *American journal of respiratory cell and molecular biology* 29(3 Pt 1):331-343.
2. Harvey B G, Heguy A, Leopold P L, et al. (2007) Modification of gene expression of the small airway epithelium in response to cigarette smoking. *J Mol Med (Berl)* 85(1):39-53.
3. Beane J, Sebastiani P, Liu G, et al. (2007) Reversible and permanent effects of tobacco smoke exposure on airway epithelial gene expression. *Genome biology* 8(9):1-17.
4. Spira A, Beane J, Shah V, et al. (2004) Effects of cigarette smoke on the human airway epithelial cell transcriptome. *Proceedings of the National Academy of Sciences of the United States of America* 101(27):10143-10148.
5. Beane J, Vick J, Schembri F, et al. (2011) Characterizing the impact of smoking and lung cancer on the airway transcriptome using RNA-Seq. *Cancer Prev Res* (Phila) 4(6):803-817.
6. Sridhar S, Schembri F, Zeskind J, et al. (2008) Smoking-induced gene expression changes in the bronchial airway are reflected in nasal and buccal epithelium. *BMC genomics* 9:259.
7. Schembri F, Sridhar S, Perdomo C, et al. (2009) MicroRNAs as modulators of smoking-induced gene expression changes in human airway epithelium. *Proceedings of the National Academy of Sciences of the United States of America* 106(7):2319-2324.
8. Chari R, Lonergan K M, Ng R T, et al. (2007) Effect of active smoking on the human bronchial epithelium transcriptome. *BMC genomics* 8:297.
9. Spira A, Beane J E, Shah V, et al. (2007) Airway epithelial gene expression in the diagnostic evaluation of smokers with suspect lung cancer. *Nature medicine* 13(3):361-366.
10. Beane J, Sebastiani P, Whitfield T H, et al. (2008) A prediction model for lung cancer diagnosis that integrates genomic and clinical features. *Cancer Prev Res* (Phila) 1(1):56-64.
11. Whitney D H, Elashoff M R, Porta-Smith K, et al. (2015) Derivation of a bronchial genomic classifier for lung cancer in a prospective study of patients undergoing diagnostic bronchoscopy. *BMC medical genomics* 8:18.
12. Silvestri G A, Vachani A, Whitney D, et al. (2015) A Bronchial Genomic Classifier for the Diagnostic Evaluation of Lung Cancer. *The New England journal of medicine* 373(3):243-251.
13. Gustafson A M, Soldi R, Anderlind C, et al. (2010) Airway PI3K pathway activation is an early and reversible event in lung cancer development. *Science translational medicine* 2(26):26ra25.
14. Wistuba, I I & Gazdar A F (2006) Lung cancer preneoplasia. *Annual review of pathology* 1:331-348.
15. Wistuba, I I, Lam S, Behrens C, et al. (1997) Molecular damage in the bronchial epithelium of current and former smokers. *Journal of the National Cancer Institute* 89(18): 1366-1373.
16. Wistuba, I I, Behrens C, Virmani A K, et al. (2000) High resolution chromosome 3p allelotyping of human lung cancer and preneoplastic/preinvasive bronchial epithelium reveals multiple, discontinuous sites of 3p allele loss and three regions of frequent breakpoints. *Cancer research* 60(7):1949-1960.
17. Wistuba, I I, Behrens C, Milchgrub S, et al. (1999) Sequential molecular abnormalities are involved in the multistage development of squamous cell lung carcinoma. *Oncogene* 18(3):643-650.
18. Belinsky S A, Palmisano W A, Gilliland F D, et al. (2002) Aberrant promoter methylation in bronchial epithelium and sputum from current and former smokers. *Cancer research* 62(8):2370-2377.
19. Lamy A, Sesboue R, Bourguignon J, et al. (2002) Aberrant methylation of the CDKN2a/p16INK4a gene promoter region in preinvasive bronchial lesions: a prospective study in high-risk patients without invasive cancer. *International journal of cancer* 100(2):189-193.
20. Nakachi I, Rice J L, Coldren C D, et al. (2014) Application of SNP microarrays to the genome-wide analysis of chromosomal instability in premalignant airway lesions. *Cancer Prev Res* (Phila) 7(2):255-265.
21. Rahman S M, Gonzalez A L, Li M, et al. (2011) Lung cancer diagnosis from proteomic analysis of preinvasive lesions. *Cancer research* 71(8):3009-3017.
22. Massion P P, Zou Y, Uner H, et al. (2009) Recurrent genomic gains in preinvasive lesions as a biomarker of risk for lung cancer. *PloS one* 4(6):e5611.
23. van Boerdonk R A, Sutedja T G, Snijders P J, et al. (2011) DNA copy number alterations in endobronchial squamous metaplastic lesions predict lung cancer. *American journal of respiratory and critical care medicine* 184(8):948-956.
24. Ishizumi T, McWilliams A, MacAulay C, Gazdar A, & Lam S (2010) Natural history of bronchial preinvasive lesions. *Cancer metastasis reviews* 29(1):5-14.
25. Lam S, Kennedy T, Unger M, et al. (1998) Localization of bronchial intraepithelial neoplastic lesions by fluorescence bronchoscopy. *Chest* 113(3):696-702.
26. Edell E, Lam S, Pass H, et al. (2009) Detection and localization of intraepithelial neoplasia and invasive carcinoma using fluorescence-reflectance bronchoscopy: an international, multicenter clinical trial. *Journal of thoracic oncology: official publication of the International Association for the Study of Lung Cancer* 4(1):49-54.
27. van Boerdonk R A, Smesseim I, Heideman D A, et al. (2015) Close Surveillance with Long-Term Follow-up of Subjects with Preinvasive Endobronchial Lesions. *American journal of respiratory and critical care medicine* 192(12):1483-1489.
28. Jeremy George P, Banerjee A K, Read C A, et al. (2007) Surveillance for the detection of early lung cancer in patients with bronchial dysplasia. *Thorax* 62(1):43-50.
29. Tammemagi M C, Lam S C, McWilliams A M, & Sin D D (2011) Incremental value of pulmonary function and sputum DNA image cytometry in lung cancer risk prediction. *Cancer Prev Res* (Phila) 4(4):552-561.
30. Li B & Dewey C N (2011) RSEM: accurate transcript quantification from RNA-Seq data with or without a reference genome. *BMC bioinformatics* 12:323.
31. Langmead B, Trapnell C, Pop M, & Salzberg S L (2009) Ultrafast and memory-efficient alignment of short DNA sequences to the human genome. *Genome Biol* 10(3):R25.
32. Katz Y, Wang E T, Airoldi E M, & Burge C B (2010) Analysis and design of RNA sequencing experiments for identifying isoform regulation. *Nature methods* 7(12): 1009-1015.
33. Anders S, Pyl P T, & Huber W (2014) HTSeq-A Python framework to work with high-throughput sequencing data. *bioRxiv*.
34. Piccolo S R, Sun Y, Campbell J D, et al. (2012) A single-sample microarray normalization method to facilitate personalized-medicine workflows. *Genomics* 100(6): 337-344.
35. Ritchie M E, Phipson B, Wu D, et al. (2015) limma powers differential expression analyses for RNA-sequencing and microarray studies. *Nucleic Acids Research* 43(7):gkv007-e047.
36. Robinson M D, McCarthy D J, & Smyth G K (2010) edgeR: a Bioconductor package for differential expression analysis of digital gene expression data. *Journal of Gerontology* 26(1):139-140.
37. Leek J T, Johnson W E, Parker H S, Jaffe A E, & Storey J D (2012) The sva package for removing batch effects and other unwanted variation in high-throughput experiments. *Bioinformatics* (Oxford, England) 28(6):882-883.
38. Law C W, Chen Y, Shi W, & Smyth G K (2014) Voom: precision weights unlock linear model analysis tools for RNA-seq read counts. *Genome biology*.
39. Wu D, Lim E, Vaillant F, et al. (2010) ROAST: rotation gene set tests for complex microarray experiments. *Bioinformatics* 26(17):2176-2182.
40. Subramanian A, Tamayo P, Mootha V K, et al. (2005) Gene set enrichment analysis: a knowledge-based approach for interpreting genome-wide expression profiles. *Proceedings of the National Academy of Sciences of the United States of America* 102(43):15545-15550.
41. Hanzelmann S, Castelo R, & Guinney J (2013) GSVA: gene set variation analysis for microarray and RNA-seq data. *BMC bioinformatics* 14:7.

42. Mazzilli S A, Hershberger P A, Reid M E, et al. (2015) Vitamin D Repletion Reduces the Progression of Premalignant Squamous Lesions in the NTCU Lung Squamous Cell Carcinoma Mouse Model. *Cancer Prev Res* (Phila) 8(10):895-904.
43. Chacko B K, Kramer P A, Ravi S, et al. (2014) The Bioenergetic Health Index: a new concept in mitochondrial translational research. *Clin Sci* (Lond) 127(6):367-373.
44. Ooi A T, Gower A C, Zhang K X, et al. (2014) Molecular profiling of premalignant lesions in lung squamous cell carcinomas identifies mechanisms involved in stepwise carcinogenesis. *Cancer Prev Res* (Phila) 7(5):487-495.
45. Dang C V (2012) Links between metabolism and cancer. *Genes & development* 26(9):877-890.
46. Chen X, Qian Y, & Wu S (2015) The Warburg effect: evolving interpretations of an established concept. *Free radical biology & medicine* 79:253-263.
47. Phelan J J, MacCarthy F, Feighery R, et al. (2014) Differential expression of mitochondrial energy metabolism profiles across the metaplasia-dysplasia-adenocarcinoma disease sequence in Barrett's oesophagus. *Cancer letters* 354(1):122-131.
48. Xylas J, Varone A, Quinn K P, et al. (2015) Noninvasive assessment of mitochondrial organization in three-dimensional tissues reveals changes associated with cancer development. *International journal of cancer* 136(2):322-332.
49. Grimm M, Cetindis M, Lehmann M, et al. (2014) Association of cancer metabolism-related proteins with oral carcinogenesis—indications for chemoprevention and metabolic sensitizing of oral squamous cell carcinoma? *Journal of translational medicine* 12:208.
50. Pan J, Zhang Q, Liu Q, et al. (2014) Honokiol inhibits lung tumorigenesis through inhibition of mitochondrial function. *Cancer Prev Res* (Phila) 7(11):1149-1159.
51. Zhang X, Sebastiani P, Liu G, et al. (2010) Similarities and differences between smoking-related gene expression in nasal and bronchial epithelium. *Physiological genomics* 41(1):1-8.
52. Campbell J D, Mazzilli S A, Reid M E, et al. (2016) The Case for a Pre-Cancer Genome Atlas (PCGA). *Cancer Prev Res* (Phila) 9(2):119-124.
53. Kensler T W, Spira A, Garber J E, et al. (2016) Transforming Cancer Prevention through Precision Medicine and Immune-oncology. *Cancer Prev Res* (Phila) 9(1):2-10.
54. Edgar R, Domrachev M, & Lash A E (2002) Gene Expression Omnibus: NCBI gene expression and hybridization array data repository. *Nucleic Acids Research* 30(1):207-210.
55. Irizarry R A, Hobbs B, Collin F, et al. (2003) Exploration, normalization, and summaries of high density oligonucleotide array probe level data. *Biostatistics* (Oxford, England) 4(2):249-264.
56. Golub T R, Slonim D K, Tamayo P, et al. (1999) Molecular classification of cancer: class discovery and class prediction by gene expression monitoring. *Science* 286(5439):531-537.
57. Johnson W E, Li C, & Rabinovic A (2006) Adjusting batch effects in microarray expression data using empirical Bayes methods. *Biostatistics* (Oxford, England) 8(1):118-127.
58. Wang L, Wang S, & Li W (2012) RSeQC: quality control of RNA-seq experiments. *Bioinformatics* (Oxford, England) 28(16):2184-2185.
59. Trapnell C, Williams B A, Pertea G, et al. (2010) Transcript assembly and quantification by RNA-Seq reveals unannotated transcripts and isoform switching during cell differentiation. *Nature biotechnology* 28(5):511-515.
60. Robinson M D & Oshlack A (2010) A scaling normalization method for differential expression analysis of RNA-seq data. *Genome biology* 11(3):R25.
61. Friedman J, Hastie T, & Tibshirani R (2010) Regularization Paths for Generalized Linear Models via Coordinate Descent. *Journal of statistical software* 33(1):1-968.
62. Liaw A & Wiener M (2002) Classification and regression by randomForest. *R news*.
63. Anders S & Huber W (2010) Differential expression analysis for sequence count data. *Genome biology* 11(10):1.
64. Buja A & Eyuboglu N (1992) Remarks on Parallel Analysis. *Multivariate behavioral research* 27(4):509-540.
65. McClish D K (1989) Analyzing a portion of the ROC curve. *Medical decision making: an international journal of the Society for Medical Decision Making* 9(3):190-195.
66. Gentleman R, Carey V, Huber W, & Hahne F (2015) *Genefilter: methods for filtering genes from high-throughput experiments* (R package version).
67. Meyer D, Dimitriadou E, Hornik K, Weingessel A, & Leisch F (2015) e1071: Misc Functions of the Department of Statistics, Probability Theory Group (Formerly: E1071), T U Wien [R package e1071 version 1.6-7]. (Comprehensive R Archive Network (CRAN)).
68. Robin X, Turck N, Hainard A, et al. (2011) pROC: an open-source package for R and S+ to analyze and compare ROC curves. *BMC bioinformatics* 12(1):77.

What is claimed is:

1. A method of processing a sample from a subject suspected of having a premalignant bronchial lesion comprising the steps of: (a) providing a biological sample from the mouth or nose of the subject or from a brushing of the bronchi walls of the subject; and (b) measuring the expression of five or more genes in the sample by northern-blot hybridization, a ribonuclease protection assay, or a reverse transcriptase polymerase chain reaction (RT-PCR) method, wherein the five or more genes comprise ZXDC, ESR1, MYH3, RBM19, and TIMM23.

2. The method of claim 1, wherein the five or more genes further comprise at least one gene selected from AFG3L1P, TTC31, CSAD, SZT2, C15orf63, PPP1R3E, CRIPAK, FAM219A, NXF1, NISCH, ECHDC2, SRRM2, EZH1, PION, KIAA0907, SESN2, SUGP2, RBM33, TTLL3, SRCAP, ZFYVE26, IKBKB, ANKRD11, MLLT11, AVIL, ZNF445, SRGAP2, SH3BP2, DDX39B, ZNF473, DDX54, FAM65C, DDX17, CCDC193, BAZ2A, TJAP1, MCM3AP-AS1, PNN, ZNF160, LY6G5B, SGSH, KCNC3, MAU2, C5orf45, CAPRIN2, SAFB2, MED12, PPP1R12B, ZNF767, TP73-AS1, ACIN1, SIN3B, MOV10, STX16, MYO9B, NPIPL3, ATAT1, HNRNPH1, RUSC2, SLC22A5, TMEM198B, EWSR1, SPEN, MDC1, BCL9L, TMEM131, NFRKB, ASXL1, PHKA2, TRIM66, GTPBP1, SLC12A9, PXK, ELMOD3, TNRC6A, C1orf63, DNAH1, MYBBP1A, SFSWAP, CNNM3, SEPT7P2, FKBP15, WDR37, TSC1, JMJD7-PLA2G4B, MKNK1, ZNF142, LENG8, GGA1, GIT2, SF1, MED15, ZNF37BP, CTC1, KANSL3, PPRC1, PAPD7, INTS3, DCAF5, SRSF5, SLC2A11, TAZ, RAL-GPS1, DICER1-AS1, C14orf159, LRP5L, JRK, PASK, KCTD7, KIAA0182, ZBTB40, GON4L, ZNF337, POGZ, C12orf51, ALS2CL, GIGYF1, ARAP3, SLC25A45, PDE7A, IL6R, FAM178A, CATSPER2, C1orf132, TBC1D2B, CDAN1, ZNF646, TRPV1, ATXN2L, ZNF335, VPS39, AGK, DGCR8, PHF12, GRIPAP1, ATXN2, CAD, UBE2G2, KDM2A, C22orf29, PHF21A, FMNL2, CUL9, CAMTA2, TPT1-AS1, CDC142SE1, CHD8, AP1G2, PLXNA3, ZNF251, PNISR, FAM53C, GGT7, STAT6, BRD4, CREBBP, RG9MTD3, MYO18A, NAPB, SEMA6A, NUMA1, TRMU, CEP164, DOT1L, FLNB-AS1, ZNF692, HEATR8, PRR14, ZNF580, RPS8, EAPP, RPS7P11, UBE2N, RPL12P4, DPCD, NPM1, RPLP2, MRPL22, GTF2H5, HBXIP, C2orf76, NDUFS5, ATP6V1D, RPL8, COX6A1, CCDC156, RPL13AP5, ATP6V1E1, RPL39P3, ZNF32, DAD1, RPL32, RPL37A, PEX2, CD9, RPS2, PPIAP22, CDC123, JTB, CONY, UCHL3, UQCRFS1, RPL38, RPS6, UQCRQ, GOLPH3L, OST4, NME5, C6orf108, MRPL54, RPL10AP2, COX4I1, COX5A, CCDC172, COX14, COPS4, EI24, UQCRH, NDUFA1, RPL29, RPL4, OCIAD2, SEPW1, ATP5I, SNRPD2, MOSPD1, NDUFC2, MRPL36, RPL10A, MCTS1, FAM3D, C19orf43, TPI1, TMEM230, MRPL23, NDUFA8, COX5B, HIGD2A, TSEN34, C15orf48, GTF2A2, APOO, C17orf61, ENSG00000167524, ENSG00000229180, ENSG00000182873, ENSG00000247484, ENSG00000257479, ENSG00000205047, ENSG00000255847, ENSG00000245149, ENSG00000253200, ENSG00000215769, ENSG00000225828, ENSG00000224660, ENSG00000205885, ENSG00000235027, ENSG00000205890, ENSG00000249093, ENSG00000215039, ENSG00000258461, ENSG00000234290, ENSG00000238105, ENSG00000230124, ENSG00000184551, ENSG00000228544, ENSG00000258727, ENSG00000218418, ENSG00000247743, ENSG00000235297, ENSG00000186198, ENSG00000185641, ENSG00000236801, ENSG00000244398, and ENSG00000232856.

3. The method of claim 1, wherein the five or more genes comprise cDNA.

4. The method of claim 1, wherein the expression of five or more genes in the sample is measured by an RT-PCR method.

5. The method of claim 1, wherein the biological sample is obtained from the mouth of the subject.

6. The method of claim 1, wherein the subject has a positive result in an imaging study of a premalignant bronchial lesion.

* * * * *

UNITED STATES PATENT AND TRADEMARK OFFICE
CERTIFICATE OF CORRECTION

PATENT NO. : 10,927,417 B2
APPLICATION NO. : 15/644721
DATED : February 23, 2021
INVENTOR(S) : Jennifer E. Beane-Ebel et al.

Page 1 of 2

It is certified that error appears in the above-identified patent and that said Letters Patent is hereby corrected as shown below:

In the Claims

Claim 2, Column 76, Line 52, to Column 77, Line 16, the phrase "FAM65C, DDX17, CCDCI93, BAZ2A, TJAP1, MCM3AP-AS1, PNN, ZNF160, LY6G5B, SGSH, KCNC3, MAU2, C5orf45, CAPRIN2, SAFB2, MED12, PPP1R12B, ZNF767, TP73-AS1, ACIN1, SIN3B, MOV10, STX16, MYO9B, NPIPL3, ATAT1, HNRNPH1, RUSC2, SLC22A5, TMEM198B, EWSR1, SPEN, MDC1, BCL9L, TMEM131, NFRKB, ASXL1, PHKA2, TRIM66, GTPBP1, SLC12A9, PXK, ELMOD3, TNRC6A, C1orf63, DNAH1, MYBBP1A, SFSWAP, CNNM3, SEPT7P2, FKBP15, WDR37, TSC1, JMJD7-PLA2G4B, MKNK1, ZNF142, LENG8, GGA1, GIT2, SF1, MED15, ZNF37BP, CTC1, KANSL3, PPRC1, PAPD7, INTS3, DCAF5, SRSF5, SLC2A11, TAZ, RALGPS1, DICER1-AS1, C14orf159, LRP5L, JRK, PASK, KCTD7, KIAA0182, ZBTB40, GON4L, ZNF337, POGZ, C12orf51, ALS2CL, GIGYF1, ARAP3, SLC25A45, PDE7A, IL6R, FAM178A, CATSPER2, C1orf132, TBC1D2B, CDAN1, ZNF646, TRPV1, ATXN2L, ZNF335, VPS39, AGK, DGCR8, PHF12, GRIPAP1, ATXN2, CAD, UBE2G2, KDM2A, C22orf29, PHF21A, FMNL2, CUL9, CAMTA2, TPT1-AS1, CDCI42SE1, CHD8, AP1G2, PLXNA3, ZNF251, PNISR, FAM53C, GGT7, STAT6, BRD4, CREBBP, RG9MTD3, MYO18A, NAPB, SEMA6A, NUMA1, TRMU, CEP164, DOT1L, FLNB-AS1, ZNF692, HEATR8, PRR14, ZNF580, RPS8, EAPP, RPS7P11, UBE2N, RPL12P4, DPCD, NPM1, RPLP2, MRPL22, GTF2H5, HBXIP, C2orf76, NDUFS5, ATP6V1D, RPL8, COX6A1, CCDCI56, RPL13AP5, ATP6V1E1, RPL39P3, ZNF32, DAD1, RPL32, RPL37A, PEX2, CD9, RPS2, PPIAP22, CDC123, JTB, CONY, UCHL3, UQCRFS1, RPL38, RPS6, UQCRQ, GOLPH3L, OST4, NME5, C6orf108, MRPL54, RPL10AP2, COX4I1, COX5A, CCDCI72, COX14, COPS4, EI24, UQCRH,"
Should read "FAM65C, DDX17, CCDC93, BAZ2A, TJAP1, MCM3AP-AS1, PNN, ZNF160, LY6G5B, SGSH, KCNC3, MAU2, C5orf45, CAPRIN2, SAFB2, MED12, PPP1R12B, ZNF767, TP73-AS1, ACIN1, SIN3B, MOV10, STX16, MYO9B, NPIPL3, ATAT1, HNRNPH1, RUSC2, SLC22A5, TMEM198B, EWSR1, SPEN, MDC1, BCL9L, TMEM131, NFRKB, ASXL1, PHKA2, TRIM66, GTPBP1, SLC12A9, PXK, ELMOD3, TNRC6A, C1orf63, DNAH1,
MYBBP1A, SFSWAP, CNNM3, SEPT7P2, FKBP15, WDR37, TSC1, JMJD7-PLA2G4B, MKNK1, ZNF142, LENG8, GGA1, GIT2, SF1, MED15, ZNF37BP, CTC1, KANSL3, PPRC1, PAPD7, INTS3, DCAF5, SRSF5, SLC2A11, TAZ, RALGPS1, DICER1-AS1, C14orf159, LRP5L, Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,927,417 B2

JRK, PASK, KCTD7, KIAA0182, ZBTB40, GON4L, ZNF337, POGZ, C12orf51, ALS2CL, GIGYF1, ARAP3, SLC25A45, PDE7A, IL6R, FAM178A, CATSPER2, C1orf132, TBC1D2B, CDAN1, ZNF646, TRPV1, ATXN2L, ZNF335, VPS39, AGK, DGCR8, PHF12, GRIPAP1, ATXN2, CAD, UBE2G2, KDM2A, C22orf29, PHF21A, FMNL2, CUL9, CAMTA2, TPT1-AS1, CDC42SE1, CHD8, AP1G2, PLXNA3, ZNF251, PNISR, FAM53C, GGT7, STAT6, BRD4, CREBBP, RG9MTD3, MYO18A, NAPB, SEMA6A, NUMA1, TRMU, CEP164, DOT1L, FLNB-AS1, ZNF692, HEATR8, PRR14, ZNF580, RPS8, EAPP, RPS7P11, UBE2N, RPL12P4, DPCD, NPM1, RPLP2, MRPL22, GTF2H5, HBXIP, C2orf76, NDUFS5, ATP6V1D, RPL8, COX6A1, CCDC56, RPL13AP5, ATP6V1E1, RPL39P3, ZNF32, DAD1, RPL32, RPL37A, PEX2, CD9, RPS2, PPIAP22, CDC123, JTB, CCNY, UCHL3, UQCRFS1, RPL38, RPS6, UQCRQ, GOLPH3L, OST4, NME5, C6orf108, MRPL54, RPL10AP2, COX4I1, COX5A, CCDC72, COX14, COPS4, EI24, UQCRH,"